US007906544B2

(12) United States Patent
Melander et al.

(10) Patent No.: US 7,906,544 B2
(45) Date of Patent: Mar. 15, 2011

(54) INHIBITION OF BACTERIAL BIOFILMS WITH IMIDAZOLE DERIVATIVES

(75) Inventors: Christian Melander, Raleigh, NC (US); John Cavanagh, Cary, NC (US); Robert W. Huigens, III, Cary, NC (US); T. Eric Ballard, Raleigh, NC (US); Justin J. Richards, Durham, NC (US)

(73) Assignee: North Carolina State University, Raleigh, NC (US)

( * ) Notice: Subject to any disclaimer, the term of this patent is extended or adjusted under 35 U.S.C. 154(b) by 226 days.

(21) Appl. No.: 12/020,112

(22) Filed: Jan. 25, 2008

(65) Prior Publication Data

US 2008/0181923 A1 Jul. 31, 2008

Related U.S. Application Data

(60) Provisional application No. 60/886,789, filed on Jan. 26, 2007.

(51) Int. Cl.
*A61K 31/4168* (2006.01)
*C07D 233/64* (2006.01)
(52) U.S. Cl. .................................. 514/398; 548/331.1
(58) Field of Classification Search ............... 548/331.1; 514/398
See application file for complete search history.

(56) References Cited

U.S. PATENT DOCUMENTS

| 3,575,929 | A | 4/1971 | Jones |
| 4,514,382 | A | 4/1985 | Gaffar et al. |
| 5,358,960 | A | 10/1994 | Ulrich et al. |
| 5,670,055 | A | 9/1997 | Yu et al. |
| 5,814,668 | A | 9/1998 | Whittemore et al. |
| 5,834,411 | A | 11/1998 | Bolkan et al. |
| 6,143,774 | A | 11/2000 | Heckmann et al. |
| 7,087,661 | B1 | 8/2006 | Alberte et al. |
| 7,132,567 | B2 | 11/2006 | Alberte et al. |
| 7,160,879 | B2 | 1/2007 | DeSimone et al. |
| 2003/0171421 | A1 | 9/2003 | Davies et al. |
| 2003/0229000 | A1 | 12/2003 | Merritt et al. |
| 2004/0024037 | A1 | 2/2004 | Ryu et al. |
| 2004/0249441 | A1 | 12/2004 | Miller et al. |
| 2005/0161859 | A1 | 7/2005 | Miller et al. |
| 2006/0018945 | A1 | 1/2006 | Britigan et al. |
| 2006/0228384 | A1 | 10/2006 | Eldridge |
| 2006/0276468 | A1 | 12/2006 | Blow |
| 2007/0231291 | A1 | 10/2007 | Huang et al. |
| 2009/0143230 | A1 | 6/2009 | Melander et al. |
| 2009/0263438 | A1 | 10/2009 | Melander et al. |
| 2009/0270475 | A1 | 10/2009 | Melander et al. |

FOREIGN PATENT DOCUMENTS

WO    WO 2005/012263 A1    2/2005

OTHER PUBLICATIONS

Document No. 139:164905 retrieved from CAPLUS on Jan. 3, 2010.*
Document No. 80:15172 retrieved from CAPLUS on Jan. 3, 2010.*
Document No. 62:66837 retrieved from CAPLUS on Jan. 3, 2010.*
Salvatori, et al. J Org Chem, 2005, 70, pp. 8208-8211.*
Ginsburg, I. APMIS 2002, 110, pp. 753-770.*
Rice, L. Biochemical Pharmacology 2006, 71, pp. 991-995.*
Antimicrobial products in the home: The evolving problem of antibiotic resistance [online]; [retrieved on Jun. 16, 2008] [URL; http://www.cps.ca/english/statements/ID/ID06-02.htm.*
Foley L. and Büchi G. Biomimetic synthesis of dibromophakellin. J. Am. Chem. Soc. (1982), vol. 104, pp. 1776-1777.
Yamada A. et al. Development of chemical substances regulating biofilm formation. Bull. Chem. Soc. Jpn. (1997), No. 70, pp. 3061-3069.
Mourabit A. A. and Potier P. Sponge's molecular diversity through the ambivalent reactivity of 2-aminoimidazole: a universal chemical pathway to the oroidin-based pyrrole-imidazole alkaloids and their palau'amine congeners. Eur. J. Org. Chem. (2001), pp. 237-243.
Musk Jr. D.J. and Hergenrother P.J. Chemical countermeasures for the control of bacterial biofilms: effective compounds and promising targets. Current Medicinal Chemistry (2006), vol. 13, pp. 2163-2177.
Huigens III R.W., et al. Inhibition of pseudomonas aeruginosa biofilm formation with bromoageliferin analogues. J. Am. Chem. Soc. (2007), vol. 129, pp. 6966-6967.
International Search Report and Written Opinion for PCT/US08/01045, dated May 9, 2008.
Shore D. College Profile: Dr. John Cavanagh shows that in scientific collaboration—as in a community of molecules—the product is more powerful than the sum of its parts. Perspectives Online. North Carolina State University. Summer 2007: 4 pp.
Fishing for seafood safety. Scope. North Carolina State University College of Physical and Mathematical Sciences. Fall 2007: 11.
Galvin F. Marine inspiration for biofilm break up. Chemical Biology. RCS Publishing. Mar. 5, 2008: 2 pp.
Melander C et al. Evaluation of dihydrooroidin as an antifouling additive in marine paint. International Biodeterioration & Biodegradation. 2009; 53: 529-532.
Stokstad E. Sponging away antibiotic resistance. Findings. The Science Magazine News Blog. Feb. 14, 2009: 1 p.
Lydersen K. Scientists learning to target bacteria where they live. washingtonpost.com. The Washington Post. Mar. 9, 2009; A05: 3 pp.
Taking the Resistance out of drug-resistant infections. PhysOrg.com. Apr. 10, 2009: 2 pp.
Avery S. Slime-fighting molecule may rearm antibiotics. newsobserver.com. The News and Observer. Raleigh, NC. Apr. 22, 2009: 2 pp.
International Search Report and Written Opinion, PCT/US09/02101, mailed Jul. 13, 2009.
International Search Report and Written Opinion, PCT/US09/02446, mailed Aug. 31, 2009.
Casalinuovo IA et al. Fluconazole resistance in *Candida albicans*: a review of mechanisms. European Review for Medical and Pharmacological Sciences. 2004; 8(2): 69-77.
Rogers SA et al. A 2-aminobenzimidazole that inhibits and disperses gram-positive biofilms through a zinc-dependent mechanism. J. Am. Chem. Soc. 2009; 131(29): 9868-9869.

(Continued)

*Primary Examiner* — Shawquia Young
(74) *Attorney, Agent, or Firm* — Myers Bigel Sibley & Sajovec, P.A.

(57) ABSTRACT

Disclosure is provided for imidazole derivative compounds that prevent, remove and/or inhibit the formation of biofilms, compositions comprising these compounds, devices comprising these compounds, and methods of using the same.

15 Claims, 15 Drawing Sheets

OTHER PUBLICATIONS

Richards JJ et al. Amide isosteres of oroidin: assessment of antibiofilm activity and *C. elegans* toxicity. Journal of Medicinal Chemistry. 2009; 52(15): 4582-4585.

Richards JJ and Melander C. Controlling bacterial biofilms. ChemBioChem. Epub ahead of print: Aug. 13, 2009; 9 pp.

Hoffmann H and Lindel T. Synthesis of the pyrrole-imidazolealkaloids. Synthesis. 2003; 12: 1753-1783.

Kelly SR et al. Effects of Caribbean sponge extracts on bacterial attachment. Aquatic Microbial Ecology. Mar. 13, 2003; 31: 175-182.

Kelly SR et al. Effects of Caribbean sponge secondary metabolites on bacterial colonization. Aquatic Microbial Ecology. Sep. 6, 2005; 40: 191-203.

Ballard TE et al. Synthesis and antibiofilm activity of a second—generation reverse-amide oroidin library: a structure-activity relationship study. Chemistry. 2008; 14(34): 10745-61. Abstract only.

Huigens RW 3rd et al. Control of bacterial biofilms with marine alkaloid derivatives. Molecular BioSystems. 2008; 4: 614-621.

Richards JJ et al. Inhibition and dispersion of Pseudomonas aeruginosa biofilms with reverse amide 2-aminoimidazole oroidin analogues. Organic & Biomolecular Chemistry. Apr. 21, 2008; 6(8): 1301-1512.

Richards JJ et al. Effects of N-pyrrole substitution on the anti-biofilm activities of oroidin derivatives against Acinetobacter baumannii. Bioorganic & Medicinal Chemistry Letters. 2008; 18: 4325-4327.

Richards JJ and Melander C. Synthesis of a 2-aminoimidazole library for antibiofilm screening utilizing the Sonogashira reaction. J. Org. Chem. 2008; 73(13): 5191-5193.

Richards JJ et al. Inhibition and dispersion of proteobacterial biofilms. Chem. Comm. 2008; 1698-1700.

Richards JJ et al. Synthesis and screening of an oroidin library against *Pseudomonas aeruginosa* biofilms. ChemBioChem. 2008; 9: 1267-1279.

Rogers SA and Melander C. Construction and screening of a 2-aminoimidazole library identifies a small molecule capable of inhibiting and dispersing bacterial biofilms across order, class, and phylum. Angew. Chem. Int. Ed. 2008; 47: 5229-5231.

Ballard TE et al. Antibiofilm activity of a diverse oroidin library generated through reductive acylation. J. Org. Chem. 2009; 74(4): 1755-1758.

Huigens RW 3rd et al. Inhibition of *Acinetobacter baumannii*, *Staphylococcus aureus* and *Pseudomonas aeruginosa* biofilm formation with a class of Tage-triazole conjugates. Org. Biomol. Chem. 2009; 7: 794-802.

Rogers SA et al. Tandem dispersion and killing of bacteria from a biofilm. Organic & Biomolecular Chemistry. 2009; 7: 603-606.

Wang B et al. Drug delivery: principles and applications. 2005 John Wiley & Sons, Inc. Publication. Section 8.3, pp. 136-137.

Smith DA. Do prodrugs deliver? Current Opinion in Drug Discovery & Development. 2007; 10(5): 550-559.

Rautio J et al. Prodrugs: design and clinical applications. Nature Reviews. Mar. 2008; 7: 255-270.

Testa B. Prodrugs: bridging pharmacodynamic/pharmacokinetic gaps. Current Opinion in Chemical Biology. 2009; 13: 338-344.

Rogers SA et al. Chemical synthesis and biological screening of 2-aminoimidazole-based bacterial and fungal antibiofilm agents. Chembiochem. Feb. 2010; 11: 396-410.

Rogers SA et al. Synergistic effects between conventional antibiotics and 2-aminoimidazole-derived antibiofilm agents. Antimicrob. Agents Chemother. Mar. 8, 2010: 1-34.

* cited by examiner

| COMPOUND | % INHIBITION vs. PAO1 | % INHIBITION vs. PA14 |
| --- | --- | --- |
| OROIDIN (4) | >95 | >95 |
| 5 | 14 ± 3 | 10 ± 2 |
| 32 | 20 ± 2 | 15 ± 1 |
| 19 | 9 ± 4 | 12 ± 1 |
| 8 | 31 ± 2 | 50 ± 3 |
| 9 | >95 | >95 |
| 10 | >95 | >95 |
| 11 | >95 | >95 |
| 12 | >95 | >95 |
| 13 | 64 ± 5 | 70 ± 6 |
| 14 | 53 ± 3 | 67 ± 5 |
| 15 | 49 ± 6 | 63 ± 4 |
| 16 | 31 ± 4 | 55 ± 5 |

31 R = H (DISPACAMIDE)
32 R = CH$_3$ (*N*-METHYL-DISPACAMIDE)

R=NH$_2$ (27)
IC$_{50}$ = 165 ± 23 µM vs PAO1
IC$_{50}$ = 224 ± 22 µM vs PA14

R=H (40)
IC$_{50}$ = 277 ± 35 µM vs PAO1
IC$_{50}$ = 203 ± 25 µM vs PA14

INHIBITION OF BACTERIAL BIOFILMS WITH IMIDAZOLE DERIVATIVES

RELATED APPLICATIONS

This application claims the benefit under 35 U.S.C. §119 (e) of U.S. Provisional Patent Application Ser. No. 60/886,789, filed Jan. 26, 2007, the disclosure of which is incorporated herein by reference in its entirety.

FIELD OF THE INVENTION

This invention relates to compositions and methods useful for controlling biofilms.

BACKGROUND OF THE INVENTION

Biofilms are complex communities of microorganisms that are commonly found on a variety of substrates or surfaces that are moist or submerged (Musk et al., *Curr. Med. Chem.*, 2006, 13, 2163; Donlan et al., *Clin. Microbiol. Rev.*, 2002, 15, 167). Though primarily populated by bacteria, biofilms can also contain many different individual types of microorganisms, e.g., bacteria, archaea, protozoa and algae. The formation of biofilms can be thought of as a developmental process in which a few free-swimming (planktonic) bacteria adhere to a solid surface and, in response to appropriate signals, initiate the formation of a complex sessile microcolony existing as a community of bacteria and other organisms. Bacteria within biofilms are usually embedded within a matrix, which can consist of protein, polysaccharide, nucleic acids, or combinations of these macromolecules. The matrix is a critical feature of the biofilm that protects the inhabiting organisms from antiseptics, microbicides, and host cells. It has been estimated that bacteria within biofilms are upwards of 1,000-fold more resistant to conventional antibiotics (Rasmussen et al., *Int. J. Med. Microbiol.*, 2006, 296, 149).

Biofilms play a significant role in infectious disease. It is estimated that biofilms account for between 50-80% of microbial infections in the body, and that the cost of these infections exceeds $1 billion annually. For example, persistent infections of indwelling medical devices remain a serious problem for patients, because eradication of these infections is virtually impossible. A few diseases in which biofilms have been implicated include endocarditis, otitis media, chronic prostatitis, periodontal disease, chronic urinary tract infections, and cystic fibrosis. The persistence of biofilm populations is linked to their inherent insensitivity to antiseptics, antibiotics, and other antimicrobial compounds or host cells.

Cystic fibrosis (CF), with 7 million asymptomatic heterozygous carriers, is one of the most common genetic diseases in the United States. Despite significant progress in the management of the symptoms of CF, virtually all CF patients succumb to chronic pulmonary infections. For reasons that are not entirely clear, the airways of CF patients are particularly susceptible to bacterial colonization. CF patients typically become infected with *Staphylococcus aureus, Streptococcus pneumoniae, Haemophilus influenzae, Burkholderia cepacia* complex, and nonmucoid *Pseudomonas aeruginosa*. However, as the patients age, *Pseudomona aeruginosa* becomes the predominant pulmonary pathogen, present in up to 85% of cultures from patients with advanced disease. Once colonized by *Pseudomonas aeruginosa*, the organism persists for many years or decades and is never eradicated. This persistence of *Pseudomonas aeruginosa* has been linked to its ability to form biofilms. Complications arising from *Pseudomonas aeruginosa* infections are the leading cause of death among CF patents.

Deleterious effects of biofilms are also found in non-medical settings. For example, biofilms are a major problem in the shipping industry. Biofilms form on and promote the corrosion of ship hulls and also increase the roughness of the hulls, increasing the drag on the ships and thereby increasing fuel costs. The biofilms can also promote the attachment of larger living structures, such as barnacles, to the hull. Fuel can account for half of the cost of marine shipping, and the loss in fuel efficiency due to biofilm formation is substantial. One method of controlling biofilms is to simply scrape the films off of the hulls. However, this method is costly and time-consuming, and can promote the spread of troublesome non-native species in shipping waters. Another method involves the use of antifouling coatings containing tin. However, tin-based coatings are now disfavored due to toxicity concerns.

Given the breadth of detrimental effects caused by bacterial biofilms, there has been an effort to develop small molecules that will inhibit their formation (Musk et al., *Curr. Med. Chem.*, 2006, 13, 2163). The underlying principle is that if bacteria can be maintained in the planktonic state, they will either not attach to a target surface and/or they can be killed by a lower dose of microbicide.

Despite the extent of biofilm driven problems, examples of structural scaffolds that inhibit biofilm formation are rare (Musk et al., *Curr. Med. Chem.*, 2006, 13, 2163). The few known examples include the homoserine lactones (Geske et al., *J. Am. Chem. Soc.*, 2005, 127, 12762), which are naturally-occurring bacterial signaling molecules that bacteria use in quorum sensing (Dong et al., *J. Microbiol.*, 2005, 43, 101; Nealson et al., *J. Bacteriol.*, 1970, 104, 313), brominated furanones isolated from the macroalga *Delisea pulchra* (Hentzer et al., *Microbiology-Sgm*, 2002, 148, 87), and ursene triterpenes from the plant *Diospyros dendo* (Hu et al., *J. Nat. Prod.*, 2006, 69, 118). While the focus has predominantly been on designing small molecules that inhibit the formation of biofilms, one of the more significant challenges is the development of a small molecule that disperses pre-formed biofilms. None of the small molecules noted above have been previously reported to disperse an existing biofilm.

In addition, bacteria have an unparalleled ability to overcome foreign chemical insult. For example, resistance to vancomycin, "the antibiotic of last resort," has become more prevalent, and strains of vancomycin-resistant *Staphylococcus aureus* have become a serious health risk. It has been predicted that it is simply a matter of time before different bacterial strains develop vancomycin resistance, and the safety net that vancomycin has provided for decades in antibiotic therapy will no longer be available. Therefore, the identification of chemical architectures useful to inhibit biofilm development is needed.

Because of their natural resistance to antibiotics, phagocytic cells, and other biocides, biofilms are difficult, if not impossible, to eradicate. Therefore, the identification of compounds that control biofilm formation is of critical need.

SUMMARY OF THE INVENTION

Provided herein are compounds of Formula (I):

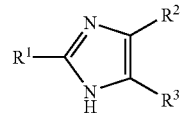

(I)

wherein:

$R^1$ and $R^2$ and $R^3$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof. Each group can be optionally substituted.

Also provided are compounds of Formula (I)(a):

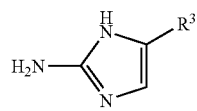

(I)(a)

wherein:

$R^3$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

or a pharmaceutically acceptable salt or prodrug thereof. Each group can be optionally substituted.

Further provided are compounds of Formula (II):

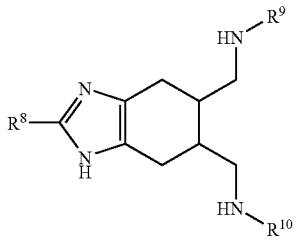

(II)

wherein:

$R^8$ is selected from the group consisting of: H, amino, hydroxy, and thiol; and $R^9$ and $R^{10}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof. Each group can be optionally substituted.

Also provided are compounds of Formula (II)(b):

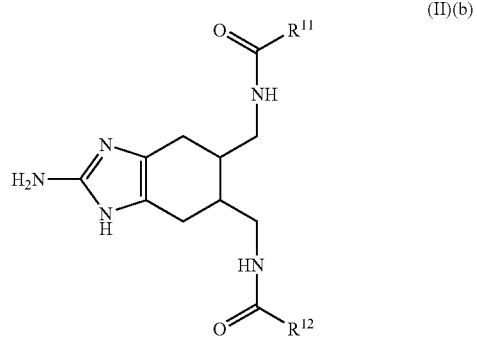

(II)(b)

wherein:

$R^{11}$ and $R^{12}$ are each independently selected from the group consisting of: H, hydroxy, acyl, alkyl alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof Each group can be optionally substituted.

Also provided are compounds of Formula (II)(c):

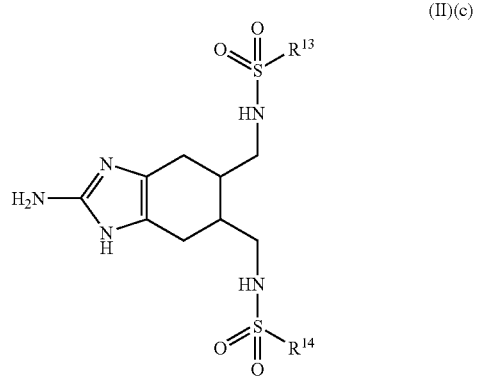

(II)(c)

wherein:

$R^{13}$ and $R^{14}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof Each group can be optionally substituted.

Further provided are compounds of Formula (III):

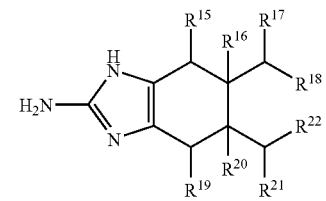

(III)

wherein:

$R^{15}, R^{16}, R^{17}, R^{18}, R^{19}, R^{20}, R^{21}$ and $R^{22}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof. Each group can be optionally substituted.

Provided are compounds of Formula (IV):

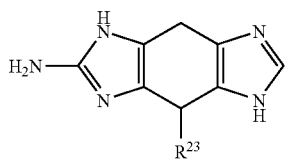

(IV)

wherein:

$R^{23}$ is selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof. Each group can be optionally substituted.

Also provided are compounds of Formula (V) and Formula (VI):

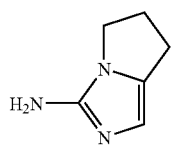

(V)

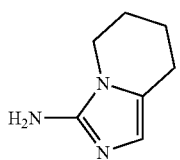

(VI)

These formulas are also optionally substituted.

Also provided are compounds of Formula (X):

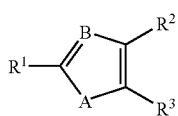

Formula (X)

wherein:

$R^1$ and $R^2$ and $R^3$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and A and B are each independently selected from N, S and O.

Further provided are compounds of Formula (X)(I)(a):

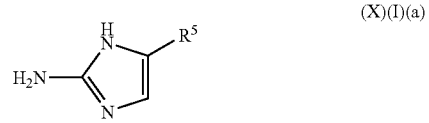

(X)(I)(a)

wherein $R^5$ is an alkyl, alkenyl or alkynyl having an amide group substituted thereon;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Also provided are compounds of Formula (X)(I)(a)(1):

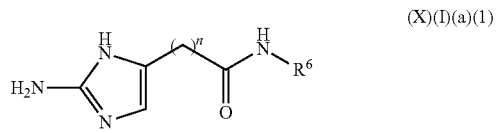

(X)(I)(a)(1)

wherein:

n is 1 to 10 carbons, saturated or unsaturated; and $R^6$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Provided are compounds of Formula (X)(I)(a)(2):

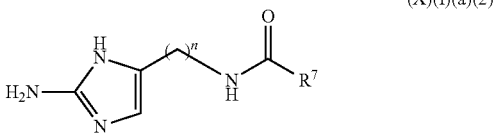

(X)(I)(a)(2)

wherein:

n is 1 to 10 carbons, saturated or unsaturated, substituted or unsubstituted; and $R^7$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Also provided are compounds of Formula (X)(I)(a)(2)(A):

(X)(I)(a)(2)(A)

wherein:
n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
or a pharmaceutically acceptable salt or prodrug thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Provided are compounds of Formula (X)(I)(b):

(X)(I)(b)

wherein $R^8$ is an alkyl, alkenyl or alkynyl having an amide group substituted thereon;
or a pharmaceutically acceptable salt or prodrug thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Also provided are compounds of Formula (X)(I)(b)(1):

(X)(I)(b)(1)

wherein:
n is 1 to 10 carbons, saturated or unsaturated; and
$R^9$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
or a pharmaceutically acceptable salt or prodrug thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Further provided are compounds of Formula (X)(I)(b)(2):

(X)(I)(b)(2)

wherein:
n is 1 to 10 carbons, saturated or unsaturated, substituted or unsubstituted; and
$R^{10}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
or a pharmaceutically acceptable salt or prodrug thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Also provided are compounds of Formula (X)(I)(b)(2)(A):

(X)(I)(b)(2)(A)

wherein:
n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
or a pharmaceutically acceptable salt or prodrug thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Provided are compounds of Formula (X)(I)(c):

(X)(I)(c)

wherein $R^{11}$ is an alkyl, alkenyl or alkynyl having an amide group substituted thereon;
or a pharmaceutically acceptable salt or prodrug thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Also provided are compounds of Formula (X)(I)(c)(1):

(X)(I)(c)(1)

wherein:

n is 1 to 10 carbons, saturated or unsaturated; and $R^{12}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Further provided are compounds of Formula (X)(I)(a)(2):

(X)(I)(c)(2)

wherein:

n is 1 to 10 carbons, saturated or unsaturated, substituted or unsubstituted; and $R^{13}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Also provided are compounds of Formula (X)(I)(c)(2)(A):

(X)(I)(c)(2)(A)

wherein:

n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Biofilm preventing, removing or inhibiting compositions are provided, which include a carrier and an effective amount of a compound disclosed herein. In some embodiments, the composition is a dentifrice composition that promotes dental hygiene by preventing, reducing, inhibiting or removing a biofilm. In some embodiments, the dentifrice composition comprises a toothpaste, mouthwash, chewing gum, dental floss, or dental cream.

Compositions are also provided that include a compound disclosed herein in a pharmaceutically acceptable carrier.

Compositions are further provided that include a compound disclosed herein covalently coupled to a substrate. In some embodiments, the substrate includes a polymeric material. In some embodiments, the substrate includes a solid support. In some embodiments, the substrate includes a drainpipe, glaze ceramic, porcelain, glass, metal, wood, chrome, plastic, vinyl, and Formica® brand laminate (The Diller Corporation, Cincinnati, Ohio). In some embodiments, the substrate includes shower curtains or liners, upholstery, laundry, and carpeting. In some embodiments, the substrate includes a ship hull or a portion thereof. In some embodiments, the substrate includes a food contact surface.

Biofilm preventing, removing or inhibiting coating compositions are provided, including: (a) a film-forming resin; (b) a solvent that disperses said resin; (c) an effective amount of the compounds or compositions disclosed herein, wherein said effective amount prevents or inhibits the growth of a biofilm thereon; and (d) optionally, at least one pigment. In some embodiments, the compound is covalently coupled to the resin. In some embodiments, the resin includes a polymeric material.

Substrates coated with coating composition disclosed herein are also provided. In some embodiments, the substrate includes a polymeric material. In some embodiments, the substrate includes a solid support. In some embodiments, the substrate includes a drainpipe, glaze ceramic, porcelain, glass, metal, wood, chrome, plastic, vinyl, and Formica® brand laminate. In some embodiments, the substrate includes shower curtains or liners, upholstery, laundry, and carpeting. In some embodiments, the substrate includes a ship hull or a portion thereof. In some embodiments, the substrate includes a food contact surface.

Methods of controlling biofilm formation on a substrate are provided, including the step of contacting the substrate with a compound and/or composition disclosed herein in an amount effective to inhibit biofilm formation. In some embodiments, controlling biofilm formation includes clearing a preformed biofilm from said substrate by administering an effective amount of the compound and/or composition disclosed herein to said substrate, wherein said effective amount will reduce the amount of said biofilm on said substrate. In some embodiments, the substrate may include a drainpipe, glaze ceramic, porcelain, glass, metal, wood, chrome, plastic, vinyl, and Formica® brand laminate. In some embodiments, the substrate may include a food product (e.g., seafood). In some embodiments, the biofilm includes Gram-negative bacteria.

Methods for treating and/or preventing a bacterial infection (e.g., chronic bacterial infection) in a subject in need thereof are provided, including administering to said subject a compound and/or composition disclosed herein in an amount effective to inhibit, reduce, or remove a biofilm component of said bacterial infection. The bacterial infection may include urinary tract infection, gastritis, respiratory infection, cystitis, pyelonephritis, osteomyelitis, bacteremia, skin infection, rosacea, acne, chronic wound infection, infectious kidney stones, bacterial endocarditis, and sinus infection.

Also provided are medical devices, including (a) a medical device substrate; and (b) an effective amount of a compound disclosed herein, either coating the substrate, or incorporated into the substrate, wherein said effective amount prevents or inhibits the growth of a biofilm thereon. In some embodiments, the medical device substrate may include stents, fasteners, ports, catheters, scaffolds and grafts. In some embodiments, the compound is covalently coupled to said substrate.

Compounds and/or compositions for use in a method to control a biofilm are further provided. Also provided is the use of compounds and/or compositions disclosed herein for the preparation of a medicament for the treatment and/or prevention of a bacterial infection (e.g., chronic bacterial infection).

DETAILED DESCRIPTION OF THE PREFERRED EMBODIMENTS

Figure 1:
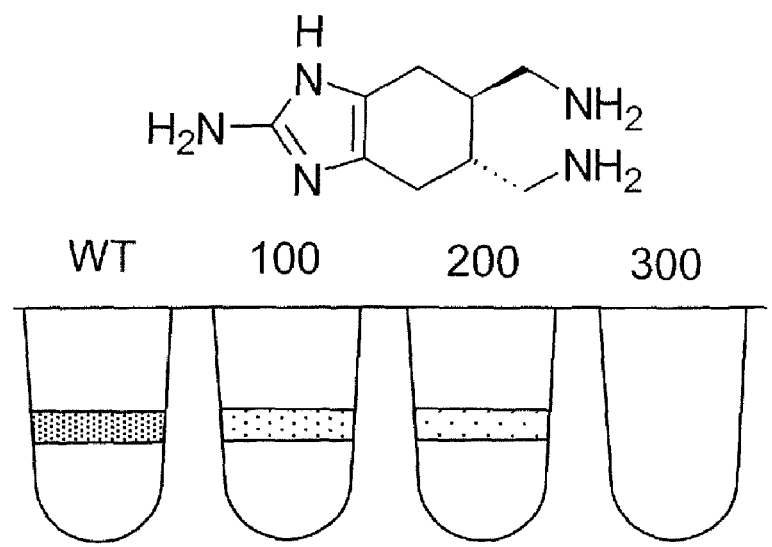
FIG. 1. Biofilm development analysis by crystal violet staining (4-h biofilm attachment assay). WT=no compound; 100=100 µg/mL; WT=no compound; 200=200 µg/mL; WT=no compound; 300=300 µg/mL.
Figure 1:
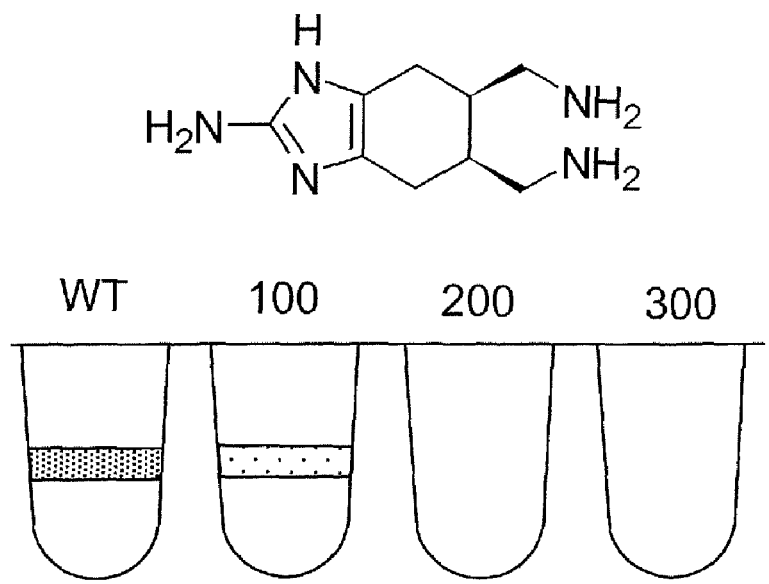

The present invention is further described below. All patent references referred to in this patent application are hereby incorporated by reference in their entirety as if set forth fully herein.

A. Definitions

"Imidazole" refers to the commonly known stricture:

"H" refers to a hydrogen atom. "C" refers to a carbon atom. "N" refers to a nitrogen atom. "O" refers to an oxygen atom. "Halo" refers to F, Cl, Br or I. The term "hydroxy," as used herein, refers to an —OH moiety. "Br" refers to a bromine atom. "Cl" refers to a chlorine atom. "I" refers to an iodine atom. "F" refers to a fluorine atom.

An "acyl group" is intended to mean a —C(O)—R radical, where R is a suitable substituent (for example, an acetyl group, a propionyl group, a butyroyl group, a benzoyl group, or an alkylbenzoyl group).

"Alkyl," as used herein, refers to a straight or branched chain hydrocarbon containing from 1 or 2 to 10 or 20 or more carbon atoms (e.g., C2, C3, C4, C5, C6, C7, C8, C9, C10, C11, C12, C13, C14, C15, etc.). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2, 3-dimethylpentyl, n-heptyl, n-octyl, n-nonyl, n-decyl, and the like. In some embodiments, alkyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

The term "optionally substituted" indicates that the specified group is either unsubstituted, or substituted by one or more suitable substituents. A "substituent" is an atom or atoms substituted in place of a hydrogen atom on the parent chain or cycle of an organic molecule, for example, H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Alkenyl," as used herein, refers to a straight or branched chain hydrocarbon containing from 1 or 2 to 10 or 20 or more carbons, and containing at least one carbon-carbon double bond, formed structurally, for example, by the replacement of two hydrogens. Representative examples of "alkenyl" include, but are not limited to, ethenyl, 2-propenyl, 2-methyl- 2-propenyl, 3-butenyl, 4-pentenyl, 5-hexenyl, 2-heptenyl, 2-methyl-1-heptenyl, 3-decenyl and the like. In some embodiments, alkenyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Alkynyl," as used herein, refers to a straight or branched chain hydrocarbon group containing from 1 or 2 to 10 or 20 or more carbon atoms, and containing at least one carbon-carbon triple bond. Representative examples of alkynyl include, but are not limited, to acetylenyl, 1-propynyl, 2-propynyl, 3-butynyl, 2-pentynyl, 1-butynyl and the like. In some embodiments, alkynyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

The term "cycloalkyl," as used herein, refers to a saturated cyclic hydrocarbon group containing from 3 to 8 carbons or more. Representative examples of cycloalkyl include, cyclopropyl, cyclobutyl, cyclopentyl, cyclohexyl, cycloheptyl, and cyclooctyl. In some embodiments, cycloalkyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Heterocyclo," as used herein, refers to a monocyclic or a bicyclic ring system. Monocyclic heterocycle ring systems are exemplified by any 5 or 6 member ring containing 1, 2, 3, or 4 heteroatoms independently selected from the group consisting of O, N, and S. The 5 member ring has from 0 to 2 double bonds, and the 6 member ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, sulfoxide, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like.

"Aryl" as used herein refers to a fused ring system having one or more aromatic rings. Representative examples of aryl include, azulenyl, indanyl, indenyl, naphthyl, phenyl, tetrahydronaphthyl, and the like. The aryl groups of this invention can be substituted with 1, 2, 3, 4, or 5 substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, —NR'R" (wherein, R' and R" are independently selected from hydrogen, alkyl, alkylcarbonyl, aryl, arylalkyl and formyl), and —C(O)NR'R" (wherein R' and R" are independently selected from hydrogen, alkyl, alkylcarbonyl, aryl, arylalkyl, and formyl).

"Heteroaryl" means a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from the group consisting of: O, N, and S. The heteroaryl group, including each heteroatom, can be unsubstituted or substituted with from 1 to 4 suitable substituents, as chemically feasible. For example, the heteroatom S may be substituted with one or two oxo groups, which may be shown as =O.

"Alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like. In some embodiments, alkoxy groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

An "amine" or "amino" group is intended to mean the radical —$NH_2$. "Optionally substituted" amines refers to —$NH_2$ groups wherein none, one or two of the hydrogens is replaced by a suitable substituent as described herein, such as alkyl, alkenyl, alkynyl, cycloalkyl, heterocyclo, aryl, heteroaryl, alkoxy, carbonyl, carboxy, etc. In some embodiments, one or two of the hydrogens are optionally substituted with independently selected, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide. Disubstituted amines may have substituents that are bridging, i.e., form a heterocyclic ring structure that includes the amine nitrogen.

An "amide" as used herein refers to an organic functional group having a carbonyl group (C=O) linked to a nitrogen atom (N), or a compound that contains this group, generally depicted as:

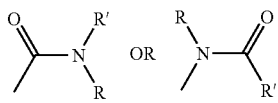

wherein, R and R' can independently be any covalently-linked atom or atoms, for example, H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

A "thiol" or "mercapto" refers to an —SH group or to its tautomer =S.

A "sulfone" as used herein refers to a sulfonyl functional group, generally depicted as:

wherein, R can be any covalently-linked atom or atoms, for example, H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

A "sulfoxide" as used herein refers to a sulfinyl functional group, generally depicted as:

wherein, R can be any covalently-linked atom or atoms, for example, H, halohydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

The term "oxo," as used herein, refers to a =O moiety. The term "oxy," as used herein, refers to a —O— moiety.

"Nitro" refers to the organic compound functional group —NO$_2$.

"Carbonyl" is a functional group having a carbon atom double-bonded to an oxygen atom (—C=O). "Carboxy" as used herein refers to a —COOH functional group, also written as —(C=O)—OH.

"Amino acid sidechain" as used herein refers to any of the 20 commonly known groups associated with naturally-occurring amino acids, or any natural or synthetic homologue thereof. An "amino acid" includes the sidechain group and the amino group, alpha-carbon atom, and carboxy groups, as commonly described in the art. Examples of amino acids include glycine, and glycine that is substituted with a suitable substituent as described herein, such as alkyl, alkenyl, alky-nyl, cycloalkyl, heterocyclo, aryl, heteroaryl, alkoxy, carbonyl, carboxy, etc., or a pharmaceutically acceptable salt or prodrug thereof. For example, "Histidine" is one of the 20 most commonly known amino acids found naturally in proteins. It contains an imidazole side chain substituent. Other examples of naturally-occurring amino acids include lysine, arginine, aspartic acid, glutamic acid, asparagine, glutamine, serine, threonine, tyrosine, alanine, valine, leucine, isoleucine, phenylalanine, methionine, cryptophan, and cysteine. Also included in the definitions of "amino acid sidechain" and "amino acid" is proline, which is commonly included in the definition of an amino acid, but is technically an imino acid. As used in this application, both the naturally-occurring L-, and the non-natural D-amino acid enantiomers are included. A "peptide" is a linear chain of amino acids covalently linked together, typically through an amide linkage, and contains from 1 or 2 to 10 or 20 or more amino acids, and is also optionally substituted and/or branched.

A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1, 4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

A "prodrug" is intended to mean a compound that is converted under physiological conditions or by solvolysis or metabolically to a specified compound that is pharmaceutically active. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein in their entirety.

B. Active Compounds

In some of the embodiments provided in the present invention, active compounds are provided. These active compounds are derivatives of imidazole. Active compounds as described herein can be prepared as detailed below or in accordance with known procedures or variations thereof that will be apparent to those skilled in the art.

As will be appreciated by those of skill in the art, the active compounds of the various formulas disclosed herein may contain chiral centers, e.g. asymmetric carbon atoms. Thus, the present invention is concerned with the synthesis of both: (i) racemic mixtures of the active compounds, and (ii) enantiomeric forms of the active compounds. The resolution of racemates into enantiomeric forms can be done in accordance with known procedures in the art. For example, the racemate may be converted with an optically active reagent into a diastereomeric pair, and the diastereomeric pair subsequently separated into the enantiomeric forms.

Geometric isomers of double bonds and the like may also be present in the compounds disclosed herein, and all such stable isomers are included within the present invention unless otherwise specified. Also included in active compounds of the invention are tautomers (e.g., tautomers of imidazole) and rotamers.

Active compounds for carrying out the present invention include compounds of Formula (I):

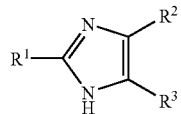
(I)

wherein:

R¹ and R² and R³ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof. Each group can be optionally substituted.

In some embodiments of Formula (I), R¹ is an amino and R² is H, depicted as Formula (I)(a):

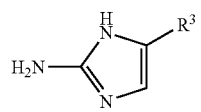
(I)(a)

wherein:

R³ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

or a pharmaceutically acceptable salt or prodrug thereof. Each group can be optionally substituted.

In some embodiments of Formula (I)(a), R³ comprises amino acid sidechains. Examples of these embodiments are depicted in Formulas (I)(a)(i)-(I)(a)(ix):

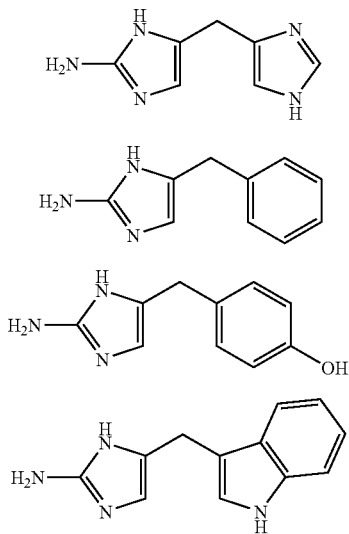
(I)(a)(i)

(I)(a)(ii)

(I)(a)(iii)

(I)(a)(iv)

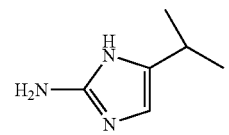
(I)(a)(v)

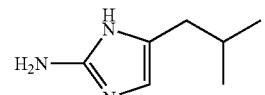
(I)(a)(vi)

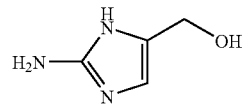
(I)(a)(vii)

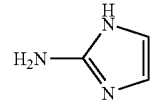
(I)(a)(viii)

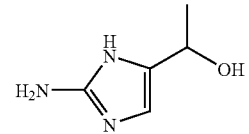
(I)(a)(ix)

In some embodiments of Formula (I)(a), R³ comprises amino alkanes or amino alkenes. Examples of these embodiments are depicted in (I)(a)(xi)-(I)(a)(xiv):

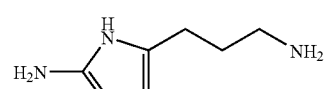
(I)(a)(xi)

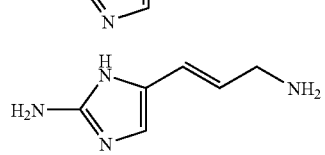
(I)(a)(xii)

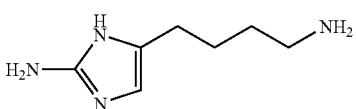
(I)(a)(xiii)

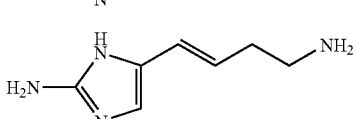
(I)(a)(xiv)

In some embodiments of Formula (I)(a), R³ comprises an alkyl or alkenyl with disubstituted amides. Examples of these embodiments are depicted in Formulas (I)(a) (xv)-(I)(a) (xviii):

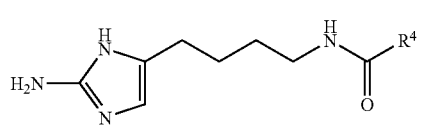
(I)(a)(xv)

-continued

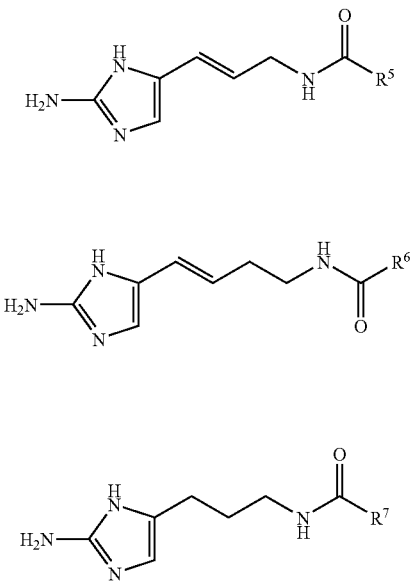

wherein:

R⁴ R⁵, R⁶, and R⁷ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

or a pharmaceutically acceptable salt or prodrug thereof. Each group can be optionally substituted.

In some embodiments of Formulas (I)(a)(xv)-(I)(a)(xviii), R⁴, R⁵, R⁶, and R⁷ comprise aryls or heteroaryls. Examples of these embodiments include those aryls and heteroaryls depicted in Formulas (II)(b)(i)-(II)(b)(ix) below for constituents R¹¹ and R¹².

In some embodiments of Formula (I)(a), R³ comprises alkyls with heterocycloalkyls, optionally substituted with further alkyls or alkenyls. Examples of these embodiments are depicted in Formulas (I)(a)(xix)-(I)(a)(xx):

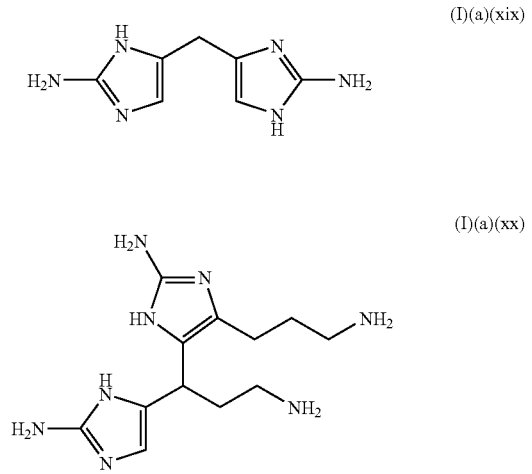

Active compounds for carrying out the present invention include compounds of Formula (II):

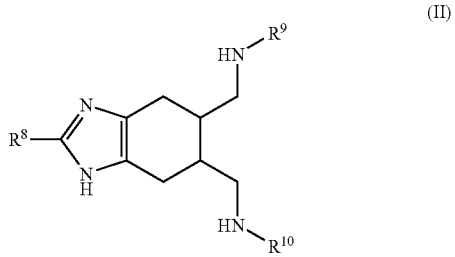

wherein:

R⁸ is selected from the group consisting of: H, amino, hydroxy, and thiol; and

R⁹ and R¹⁰ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof. Each group can be optionally substituted.

Some embodiments of the active compounds comprise derivatives of 2-aminoimidazole. For example, in some embodiments of Formula (II), R⁸ comprises an amino, R⁹ and R¹⁰ are the same, and R⁹ and R¹⁰ comprise H. Examples of these embodiments are depicted in Formula (II)(a):

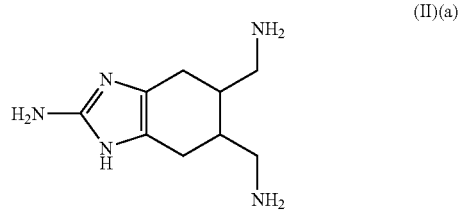

Examples of certain stereoisomers of Formula (II)(a) include those depicted in Formulas (II)(a)(i)-(II)(a)(ii):

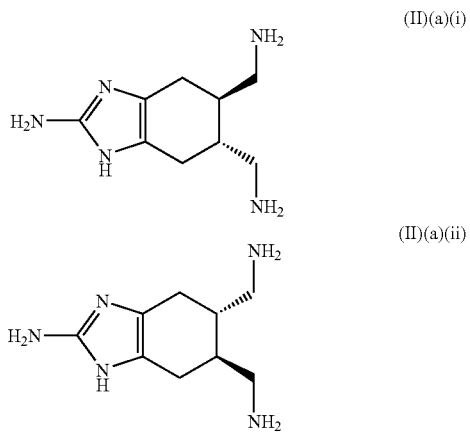

The discussion herein is, for simplicity, given without further reference to stereoisomerism. However, as noted above, the active compounds of the various formulas disclosed herein contain chiral centers, e.g. asymmetric carbon atoms. Thus, the present invention is concerned with the synthesis of both: (i) racemic mixtures of the active compounds, and (ii) enantiomeric forms of the active compounds. The resolution of racemates into enantiomeric forms can be done in accordance with known procedures in the art. For example, the racemate may be converted with an optically active reagent into a diastereomeric pair, and the diastereomeric pair subsequently separated into the enantiomeric forms.

In some embodiments of Formula (II), $R^8$ comprises an amino, and $R^9$ and $R^{10}$ comprise carbonyls, generally depicted in Formula (II)(b):

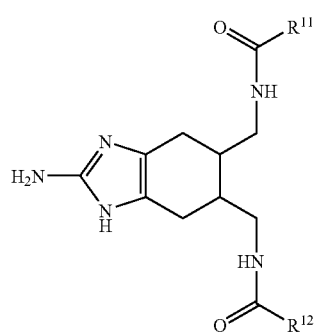
(II)(b)

wherein:

$R^{11}$ and $R^{12}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof. Each group can be optionally substituted.

In some embodiments of Formula (II)(b), $R^{11}$ and $R^{12}$ are the same, and $R^{11}$ and $R^{12}$ comprise aryls or heteroaryls Examples of these embodiments are depicted in Formulas (II)(b)(i)-(II)(b)(ix):

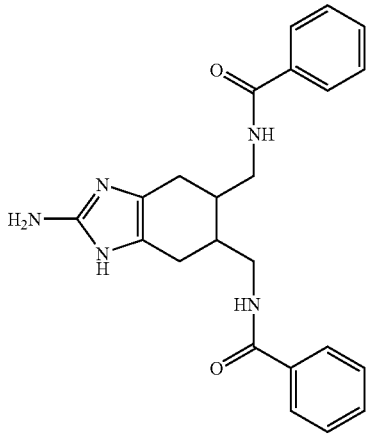
(II)(b)(i)

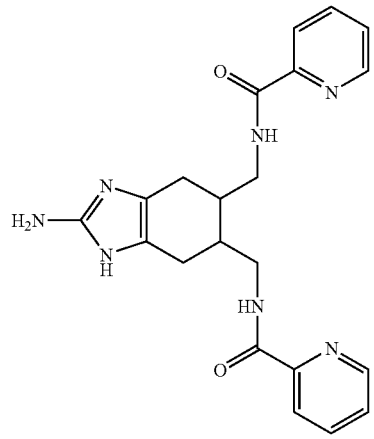
(II)(b)(ii)

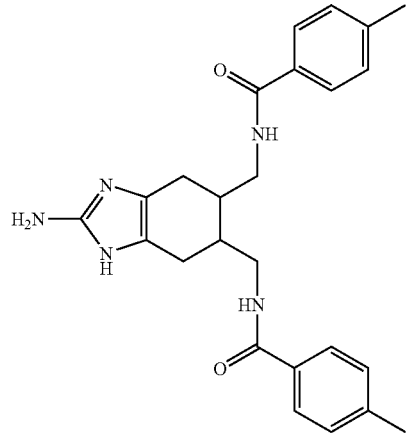
(II)(b)(iii)

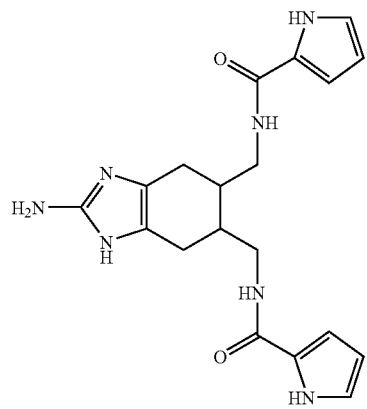
(II)(b)(iv)

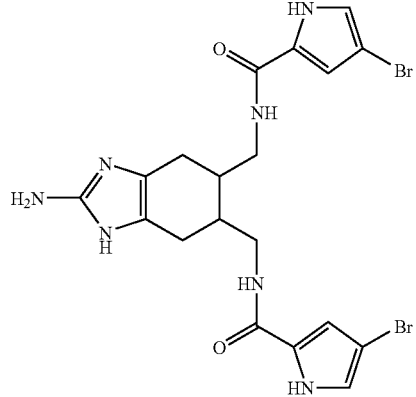
(II)(b)(v)

-continued

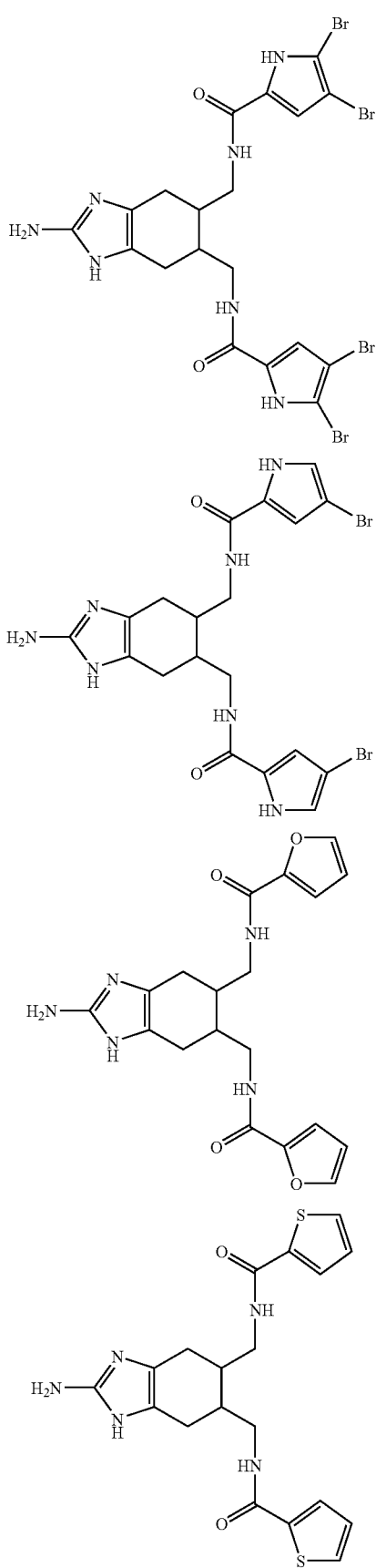

(II)(b)(vi)

(II)(b)(vii)

(II)(b)(viii)

(II)(b)(ix)

In some embodiments of Formula (II), $R^8$ comprises an amino, $R^9$ and $R^{10}$ are the same, and $R^9$ and $R^{10}$ comprise sulfones, generally depicted in Formula (II)(c):

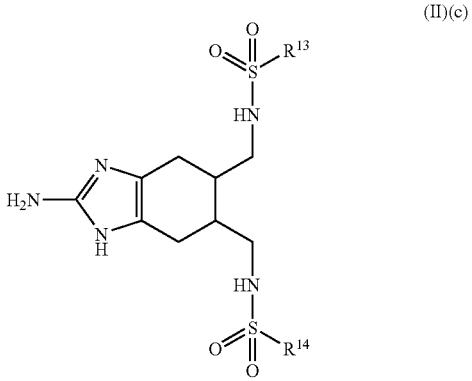

(II)(c)

wherein:

$R^{13}$ and $R^{14}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof Each group can be optionally substituted.

In some embodiments of Formula (II)(c), $R^{13}$ and $R^{14}$ are the same, and $R^{13}$ and $R^{14}$ comprise aryls or heteroaryls. An example of these embodiments is depicted in Formula (II)(c)(i):

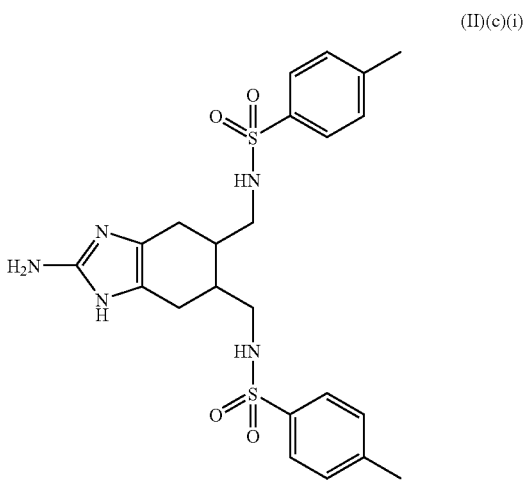

(II)(c)(i)

Active compounds for carrying out the present invention include compounds of Formula (III):

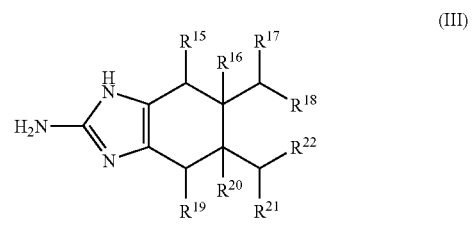

(III)

wherein:

$R^{15}$, $R^{16}$, $R^{17}$, $R^{18}$, $R^{19}$, $R^{20}$, $R^{21}$ and $R^{22}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof. Each group can be optionally substituted.

Active compounds for carrying out the present invention include compounds of Formula (IV):

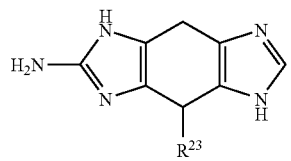

(IV)

wherein:

$R^{23}$ is selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof. Each group can be optionally substituted.

In some embodiments of Formula (IV), $R^{23}$ comprises an amino acid sidechain. Examples of these embodiments are depicted in Formula (IV)(a) through Formula (IV)(c). The amino acids or peptides are optionally substituted, exemplified in Formula (IV)(d):

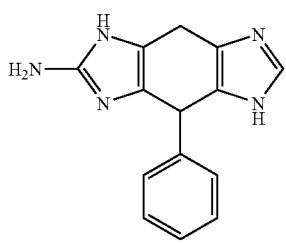

(IV)(a)

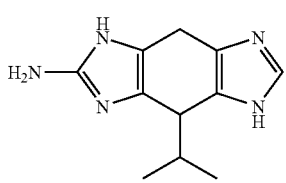

(IV)(b)

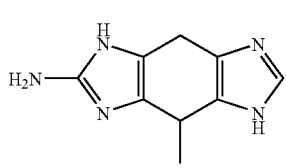

(IV)(c)

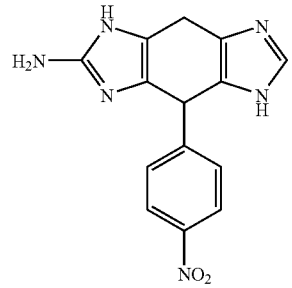

(IV)(d)

Active compound embodiments include those depicted by Formula (V) and Formula (VI):

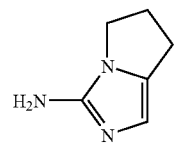

(V)

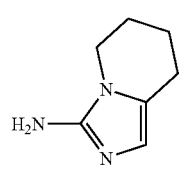

(VI)

These formulas are also optionally substituted.

Active compounds also include those represented by Formula (X):

Formula (X)

wherein:

$R^1$ and $R^2$ and $R^3$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and A and B are each independently selected from N, S and O.

or a pharmaceutically acceptable salt or prodrug thereof. Each group can be optionally substituted.

In some embodiments of Formula (X), R1 is amino; R3 is H; and A and B are each N, generally depicted by Formula (X)(I)(a):

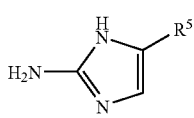

(X)(I)(a)

wherein $R^5$ is an alkyl, alkenyl or alkynyl having an amide group substituted thereon;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(a) are represented by Formula (X)(I)(a)(1):

(X)(I)(a)(1)

wherein:
n is 1 to 10 carbons, saturated or unsaturated; and
$R^6$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl. heterocyclo, aryl, heteroaryl, alkoxy, amino, amide, thiol, sulfone, sulfoxide, oxo, oxy, nitro, carbonyl, carboxy, amino acid sidechain, amino acid and peptide.

A preferred embodiment of Formula (X)(I)(a) is represented by Formula (X)(I)(a)(1)(A):

(X)(I)(a)(1)(A)

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(a) are represented by Formula (X)(I)(a)(2):

(X)(I)(a)(2)

wherein:
n is 1 to 10 carbons, saturated or unsaturated, substituted or unsubstituted; and
$R^7$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(a)(2) are represented by Formula (X)(I)(a)(2)(A):

(X)(I)(a)(2)(A)

wherein:
n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(a)(2)(A) are represented by Formula (X)(I)(a)(2)(A)(i):

(X)(I)(a)(2)(A)(i)

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (X), R1 is amino; R3 is H; and A is S and B is N, generally depicted by Formula (X)(I)(b):

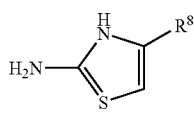

wherein R⁸ is an alkyl, alkenyl or alkynyl having an amide group substituted thereon;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(b) are represented by Formula (X)(I)(b)(1):

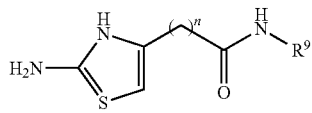

wherein:

n is 1 to 10 carbons, saturated or unsaturated; and $R^9$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

A preferred embodiment of Formula (X)(I)(b) is represented by Formula (X)(I)(b)(1)(A):

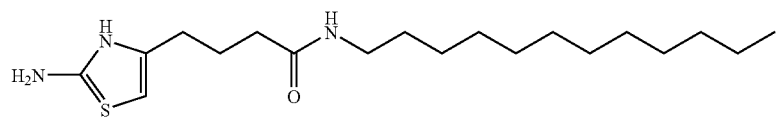

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(b) are represented by Formula (X)(I)(b)(2):

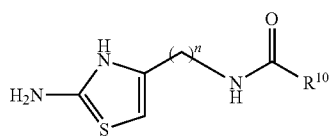

wherein:

n is 1 to 10 carbons, saturated or unsaturated, substituted or unsubstituted; and $R^{10}$ is selected form the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(b)(2) are represented by Formula (X)(I)(b)(2)(A):

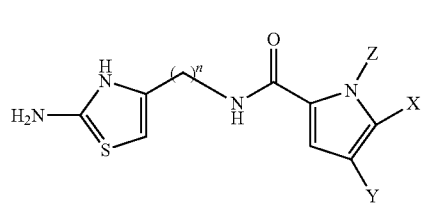

wherein:

n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(b)(2)(A) are represented by Formula (X)(I)(b)(2)(A)(i):

(X)(I)(b)(2)(A)(i)

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (X), R1 is thiol; R3 is H; and A and B are each N, generally depicted by Formula (X)(I)(c):

(X)(I)(c)

wherein $R^{11}$ is an alkyl, alkenyl or alkynyl having an amide group substituted thereon;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(c) are represented by Formula (X)(I)(c)(1):

(X)(I)(c)(1)

wherein:
n is 1 to 10 carbons, saturated or unsaturated; and
$R^{12}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodding thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

A preferred embodiment of Formula (X)(I)(c) is represented by Formula (X)(I)(c)(1)(A):

(X)(I)(c)(1)(A)

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(a) are represented by Formula (X)(I)(a)(2):

(X)(I)(c)(2)

wherein:
n is 1 to 10 carbons, saturated or unsaturated, substituted or unsubstituted; and
$R^{13}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(c)(2) are represented by Formula (X)(I)(c)(2)(A):

(X)(I)(c)(2)(A)

wherein:
n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(c)(2)(A) are represented by Formula (X)(I)(c)(2)(A)(i):

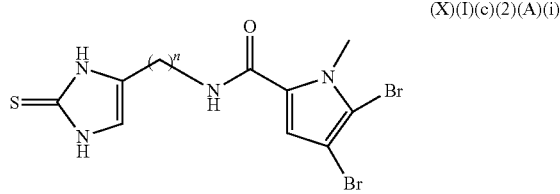

(X)(I)(c)(2)(A)(i)

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

C. Compositions

In some embodiments, biofilm preventing, removing or inhibiting compositions are provided, comprising a carrier and an effective amount of active compound. "Biofilm" or "biofilms" refer to communities of microorganisms that are attached to a substrate. The microorganisms often excrete a protective and adhesive matrix of polymeric compounds. They often have structural heterogeneity, genetic diversity, and complex community interactions. "Biofilm preventing", "biofilm removing", "biofilm inhibiting", "biofilm reducing", "biofilm resistant", "biofilm controlling" or "antifouling" refer to prevention of biofilm formation, inhibition of the establishment or growth of a biofilm, or decrease in the amount of organisms that attach and/or grow upon a substrate, tip to and including the complete removal of the biofilm. As used herein, a "substrate" can include any living or nonliving structure. For example, biofilms often grow on synthetic materials submerged in an aqueous solution or exposed to humid air, but they also can form as floating mats on a liquid surface, in which case the microorganisms are adhering to each other or to the adhesive matrix characteristic of a biofilm. An "effective amount" of a biofilm preventing, removing or inhibiting composition is that amount which is necessary to carry out the composition's function of preventing, removing or inhibiting a biofilm.

In some embodiments, the carrier is a pharmaceutically acceptable carrier. A "pharmaceutically acceptable carrier" as used herein refers to a composition that, when combined with an active compound of the present invention, facilitates the application or administration of that active compound for its intended purpose to prevent or inhibit biofilm formation, or remove an existing biofilm. The active compounds described above may be formulated for administration in a pharmaceutically acceptable carrier in accordance with known techniques. See, e.g., Remington, *The Science And Practice of Pharmacy* (9$^{th}$ Ed. 1995). The pharmaceutically acceptable carrier must, of course, also be acceptable in the sense of being compatible with any other ingredients in the composition. The carrier may be a solid or a liquid, or both, and is preferably formulated with the compound as a unit-dose composition, for example, a tablet, which may contain from 0.01 or 0.5% to 95% or 99% by weight of the active compound. One or more active compounds may be incorporated in the compositions of the invention, which may be prepared by any of the well-known techniques of pharmacy comprising admixing the components, optionally including one or more accessory ingredients.

In general, compositions of the invention are prepared by uniformly and intimately admixing the active compound with a liquid or finely divided solid carrier, or both, and then, if necessary, shaping the resulting mixture For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

The compositions of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used. Preferred routes of parenteral administration include intrathecal injection and intraventricular injection into a ventricle of the brain.

Compositions suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such compositions may be prepared by any suitable method of pharmacy, which includes the step of bringing into association the active compound and a suitable carrier (which may contain one or more accessory ingredients as noted above).

Compositions suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Compositions of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes that render the composition isotonic with the blood of the intended recipient. Aqueous and non-aqueous sterile suspensions may include suspending agents and thickening agents. The compositions may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

For example, in one aspect of the present invention, there is provided an injectable, stable, sterile composition comprising a compound of Formula (I), or a salt thereof, in a unit dosage form in a sealed container. The compound or salt is provided in the form of a lyophilizate that is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent that is physiologically acceptable may be employed in sufficient quantity to emulsify the compound or salt in an aqueous carrier. One such useful emulsifying agent is phosphatidyl choline.

Compositions suitable for rectal administration are preferably presented as unit dose suppositories. These may be prepared by mixing the active compound with one or more conventional solid carriers, for example, cocoa butter, and then shaping the resulting mixture.

Compositions suitable for topical application to the skin preferably take the form of an ointment, cream, lotion, paste, gel, spray, aerosol, or oil. Carriers that may be used include petroleum jelly, lanoline, polyethylene glycols, alcohols, transdermal enhancers, and combinations of two or more thereof.

Compositions suitable for transdermal administration may be presented as discrete patches adapted to remain in intimate contact with the epidermis of the recipient for a prolonged period of time. Compositions suitable for transdermal administration may also be delivered by iontophoresis (see, for example, *Pharmaceutical Research* 3 (6):318 (1986)) and typically take the form of an optionally buffered aqueous solution of the active compound. Suitable compositions comprise citrate or bis\tris buffer (pH 6) or ethanol/water and contain from 0.1 to 0.2M of the active ingredient.

Also provided in some embodiments are biofilm preventing, removing or inhibiting compositions comprising an active compound and an additional biocide that is not an active compound in the group herein disclosed of imidazole derivatives. "Biocide" as used herein refers to a substance with the ability to kill or to inhibit the growth of microorganisms. Common biocides include oxidizing and non-oxidizing chemicals. Examples of oxidizing biocides include chlorine, chlorine dioxide, and ozone. Examples of non-oxidizing biocides include quaternary ammonium compounds, formaldehyde, and anionic and non-anionic surface agents. Chlorine is the most common biocide used in sanitizing water systems. Antibiotics can also be biocides. Common antibiotics include aminoglycosides, cephalosporins, glycopeptides, macrolides, penicillins, polypeptides, sulfonamides, tetracyclines, etc. Antibiotics treat infections by either killing or preventing the growth of bacteria.

In some embodiments, a dentifrice composition is provided comprising the active compounds. A "dentifrice" is a substance that is used to clean the teeth. It may be in the form of, e.g., a paste or powder. Commonly known dentifrices include toothpaste, mouthwash, chewing gum, dental floss, and dental cream. Other examples of dentifrices include toothpowder, mouth detergent, troches, dental or gingival massage cream, dental strips, dental gels, and gargle tablets. Examples of dentifrice compositions comprising toothpaste and mouthwash are found in U.S. Pat. No. 6,861,048 (Yu et al.); U.S. Pat. No. 6,231,836 (Takhtalian et al.); and U.S. Pat. No. 6,331,291 (Glace et al.); each incorporated by reference herein in their entirety.

A coating composition is also provided. A "coating" as used herein is generally known. Any of a variety of organic and aqueous coating compositions, with or without pigments, may be modified to contain biofilm inhibiting compositions as described herein, including but not limited to those described in U.S. Pat. Nos. 7,109,262, 6,964,989, 6,835,459, 6,677,035, 6,528,580, 6,235,812, etc., each incorporated by reference herein in their entirety.

In general, the coatings comprise a film-forming resin, an aqueous or organic solvent that disperses the resin; and, optionally, at least one pigment. Other ingredients such as colorants, secondary pigments, stabilizers and the like can be included if desired. However, for use in the present invention the compositions further comprise one or more biofilm inhibiting compounds as described herein, which may be carried by or dispersed in the solvent and/or resin, so that the biofilm inhibiting compounds are dispersed or distributed on the substrate an article coated. A resin may carry the biofilm inhibiting compounds through covalent attachment through means well known in the art. The resin may comprise, for example, a polymeric material. A polymeric material is a material that is comprised of large molecules made from associated smaller repeating structural units, often covalently linked. Common examples of polymeric materials are unsaturated polyester resins, and epoxy resins.

Any suitable article can be coated, in whole or in part, with a composition of the invention. Suitable articles include, but are not limited to, automobiles and airplanes (including substrates such as wing and propeller surfaces for aerodynamic testing), vessel hulls (including interior and exterior surfaces thereof), pressure vessels (including interior and exterior surfaces thereof) medical implants, windmills, etc. Coating of the article with the composition can be carried out by any suitable means, such as by brushing, spraying, electrostatic deposition, dip coating, doctor blading, etc.

D. Methods of Use

Methods of controlling biofilm formation on a substrate are disclosed, comprising the step of administering an active compound to a substrate in an amount effective to inhibit biofilm formation. A "substrate" as used herein is a base on which an organism, such as those commonly found in biofilms, may live. The term "substrate," as used herein, refers to any substrate, whether in an industrial or a medical setting, that provides or can provide an interface between an object and a fluid, permitting at least intermittent contact between the object and the fluid. A substrate, as understood herein, further provides a plane whose mechanical structure, without further treatment, is compatible with the adherence of microorganisms. Substrates compatible with biofilm formation may be natural or synthetic, and may be smooth or irregular. Fluids contacting the substrates can be stagnant or flowing, and can flow intermittently or continuously, with laminar or turbulent or mixed flows. A substrate upon which a biofilm forms can be dry at times with sporadic fluid contact, or can have any degree of fluid exposure including total immersion. Fluid contact with the substrate can take place via aerosols or other means for air-borne fluid transmission.

Biofilm formation with health implications can involve those substrates in all health-related environments, including substrates found in medical environments and those substrates in industrial or residential environments that are involved in those functions essential to human well being, for example, nutrition, sanitation and the prevention of disease. Substrates found in medical environments include the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; implantable medical devices, including artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherably insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, heart valves, artificial joints, artificial larynxes, otological implants), vascular catheter ports, wound drain tubes, hydrocephalus shunts, pacemakers and implantable defibrillators, and the like. Other examples will be readily apparent to practitioners in these arts. Substrates found in the medical environment also include the inner and outer aspects of pieces of medical equipment, medical gear worn or carried by personnel in the health care setting. Such substrates can include counter tops and fixtures in areas used for medical procedures or for preparing medical apparatus, tubes and canisters used in respiratory treatments, including the administration of oxygen, of solubilized drugs in nebulizers and of anesthetic agents. Also included are those substrates intended as biological barriers to infectious organisms in medical settings, such as gloves, aprons and faceshields. Commonly used materials for biological barriers may be latex-based or non-latex based. Vinyl is commonly used as a material for non-latex surgical gloves. Other such substrates can include handles and cables for medical or dental equipment not intended to be sterile. Additionally, such substrates can include those non-sterile external substrates of tubes and other apparatus found in areas where blood or body fluids or other hazardous biomaterials are commonly encountered.

Substrates in contact with liquids are particularly prone to biofilm formation. As an example, those reservoirs and tubes used for delivering humidified oxygen to patients can bear biofilms inhabited by infectious agents. Dental unit waterlines similarly can bear biofilms on their substrates, providing a reservoir for continuing contamination of the system of flowing an aerosolized water used in dentistry. Sprays, aerosols and nebulizers are highly effective in disseminating biofilm fragments to a potential host or to another environmental site. It is especially important to health to prevent biofilm formation on those substrates from where biofilm fragments can be carried away by sprays, aerosols or nebulizers contacting the substrate.

Other substrates related to health include the inner and outer aspects of those articles involved in water purification, water storage and water delivery, and articles involved in food processing. Substrates related to health can also include the inner and outer aspects of those household articles involved in providing for nutrition, sanitation or disease prevention. Examples can include food processing equipment for home use, materials for infant care, tampons and toilet bowls. "Substrate" as used herein also refers to a living substrate, such as the inner ear of a patent.

Substrates can be smooth or porous, soft or hard. Substrates can include a drainpipe, glaze ceramic, porcelain, glass, metal, wood, chrome, plastic, vinyl, Formica® brand laminate, or any other material that may regularly come in contact with an aqueous solution in which biofilms may form and grow. The substrate can be a substrate commonly found on household items such as shower curtains or liners, upholstery, laundry, and carpeting.

A substrate on which biofilm preventing, removing or inhibiting is important is that of a ship hull. Biofilms, such as those of *Halomonas pacifica*, promote the corrosion of the hull of ships and also increase the roughness of the hull, increasing the drag on the ship and thereby increasing fuel costs. The biofilm can also promote the attachment of larger living structures such as barnacles on the ship hull. Fuel can account for half of the cost of marine shipping, and the loss in fuel efficiency due to biofilm formation is substantial.

Substrates on which biofilms can adhere include those of living organisms, as in the case of humans with chronic infections caused by biofilms, as discussed above. Biofilms can also form on the substrates of food contact surfaces, such as those used for processing seafood, and also on food products themselves. Examples of seafood products that may have biofilm contamination include oysters. Human infections caused by the ingestion of raw oysters has been linked to *Vibrio vulnificus* bacterium. Vibrio bacteria attach to algae and plankton in the water and transfer to the oysters and fish that feed on these organisms.

Other examples of substrates or devices on which biofilms can adhere can be found in U.S. Pat. Nos. 5,814,668 and 7,087,661; and U.S. Pat. Application Publication Nos. 2006/0228384 and 2006/0018945, each of which is incorporated herein by reference in their entirety.

Also disclosed is a method of controlling biofilm formation wherein the biofilm comprises Gram-negative bacteria. "Gram-negative" bacteria are those that do not retain crystal violet dye after an alcohol wash in the Gram staining protocol. This is due to structural properties in the cell walls of the bacteria. Many genera and species of Gram-negative bacteria are pathogenic. Gram-negative bacteria include members of the phylum proteobacteria, which include genus members *Escherichia, Salmonella, Vibrio*, and *Helicobacter*. A "genus" is a category of biological classification ranking between the family and the species, comprising structurally or phylogenetically related species, or an isolated species exhibiting unusual differentiation. It is usually designated by a Latin or latinized capitalized singular noun. Examples of genera of biofilm-forming bacteria affected by active compounds of this invention include, but are not limited to, *Pseudomonas, Bordetella, Vibrio, Haemophilus, Halomonas*, and *Acinetobacter*. "Species" refer to a category of biological classification ranking below the genus, and comprise members that are structurally or phylogenetically related, or an isolated member exhibiting unusual differentiation. Species are commonly designated by a two-part name, which name includes the capitalized and italicized name of the genus in which the species belongs as the first word in the name, followed by the second word that more specifically identifies the member of the genus, which is not capitalized. Examples of species of bacteria capable of forming biofilms that are affected by active compounds of the present invention include *Pseudomonas aeuroginosa, Bordetella pertussis, Vibrio vulnificus, Haemophilus influenzae, Halomonas pacifica*, and *Acinetobacter baumannii*.

Other examples of Gram-negative bacteria affected by active compounds of the present invention include, but are not limited to, bacteria of the genera *Klebsiella, Proteus, Neisseria, Helicobacter, Brucella, Legionella, Campylobacter, Francisella, Pasteurella, Yersinia, Bartonella, Bacteroides, Streptobacillus, Spirillum, Moraxella* and *Shigella*. Examples of Gram-positive bacteria affected by active compounds of the present invention include, but are not limited to, bacteria of the genera *Listeria, Staphylococcus, Streptococcus, Bacillus, Corynebacterium, Peptostreptococcus*, and *Clostridium*. Furthermore, bacteria affected by active compounds of the present invention includes Gram-positive bacteria including, but not limited to, *Listeria monocytogenes, Staphylococcus aureus, Streptococcus pyogenes, Streptococ-* cus pneumoniae, Bacillus cereus, Bacillus anthracis, Clostridium botulinum, Clostridium perfringens, Clostridium difficile, Clostridium tetani, Corynebacterium diphtheriae, Corynebacterium ulcerans, and Peptostreptococcus anaerobius. Additional bacteria affected by active compounds of the present invention also include bacterial genera including, but not limited to, Actinomyces, Propionibacterium, Nocardia and Streptomyces.

A method for treating a chronic bacterial infection in a subject in need thereof is disclosed, comprising administering active compound to said subject in an amount effective to inhibit, reduce, or remove a biofilm component of said chronic bacterial infection. "Treating" as used herein refers to any type of activity that imparts a benefit to a patient afflicted with a disease, including improvement in the condition of the patient (e.g., in one or more symptoms), delay in the progression of the disease, delay in onset of the disease, etc. The present invention is primarily concerned with the treatment of human subjects, but the invention may also be carried out on animal subjects, particularly mammalian subjects (e.g., mice, rats, dogs, cats, rabbits, and horses), avian subjects (e.g., parrots, geese, quail, pheasant), livestock (e.g., pigs, sheep, goats, cows, chickens, turkey, duck, ostrich, emu), reptile and amphibian subjects, for veterinary purposes or animal husbandry, and for drug screening and drug development purposes.

A "chronic bacterial infection" is a bacterial infection that is of a long duration or frequent recurrence. For example, a chronic middle ear infection, or otitis media, can occur when the Eustachian tube becomes blocked repeatedly due to allergies, multiple infections, ear trauma, or swelling of the adenoids. The definition of "long duration" will depend upon the particular infection. For example, in the case of a chronic middle ear infection, it may last for weeks to months. Other known chronic bacterial infections include urinary tract infection (most commonly caused by *Escherichia coli* and/or *Staphylococcus saprophyticus*), gastritis (most commonly caused by *Helicobacter pylori*), respiratory infection (such as those commonly afflicting patents with cystic fibrosis, most commonly caused by *Pseudomonas aeuroginosa*), cystitis (most commonly caused by *Escherichia coli*), pyelonephritis (most commonly caused by *Proteus* species, *Escherichia coli* and/or *Pseudomonas* species), osteomyelitis (most commonly caused by *Staphylococcus aureus*, but also by *Escherichia coli*), bacteremia, skin infection, rosacea, acne, chronic wound infection, infectious kidney stones (can be caused by *Proteus mirabilis*), bacterial endocarditis, and sinus infection. A common infection afflicting pigs is atrophic rhinitis (caused by *Bordatella* species, e.g. *Bordatella rhinitis*).

Various nosocomial infections that are especially prevalent in intensive care units implicate *Acinetobacter* species such as *Acinetobacter baumannii* and *Acinetobacter lwoffi*. *Acinetobacter baumanni* is a frequent cause of nosocomial pneumonia, and can also cause skin and wound infections and bacteremia. *Acinetobacter lwoffi* causes meningitis. The *Acinetobacter* species are resistant to many classes of antibiotics. The CDC has reported that bloodstream infections implicating *Acinetobacter baumanni* were becoming more prevalent among service members injured during the military action in Iraq and Afghanistan.

Also disclosed is a method of clearing a preformed biofilm from a substrate comprising the step of administering an effective amount of compound to said substrate, wherein said effective amount will reduce the amount of said biofilm on said substrate. "Preformed biofilm" is a biofilm that has begun to adhere to a substrate. The biofilm may or may not yet be fully formed.

E. Devices

Medical devices comprising a Substrate and an effective amount of active compounds are also disclosed. "Medical device" as used herein refers to an object that is inserted or implanted in a subject or applied to a surface of a subject. Common examples of medical devices include stents, fasteners, ports catheters, scaffolds and grafts. A "medical device substrate" can be made of a variety of biocompatible materials, including, but not limited to, metals, ceramics, polymers, gels and fluids not normally found within the human body. Examples of polymers useful in fabricating medical devices include such polymers as silicones, rubbers, latex, plastics polyanhydrides, polyesters, polyorthoesters, polyamides, polyacrylonitrile, polyurethanes, polyethylene, polytetrafluoroethylene, polyethylenetetraphthalate, etc. Medical devices can also be fabricated using certain naturally-occurring materials or treated with naturally-occurring materials. Medical devices can include any combination of artificial materials, combinations selected because of the particular characteristics of the components. Medical devices can be intended for short-term or long-term residence where they are positioned. A hip implant is intended for several decades of use, for example. By contrast, a tissue expander may only be needed for a few months, and is removed thereafter.

Some examples of medical devices are found in U.S. Pat. No. 7,081,133 (Chinn et al.); U.S. Pat. No. 6,562,295 (Neuberger); and U.S. Pat. No. 6,387,363 (Gruskin); each incorporated by reference herein in their entirety.

F. Covalent Coupling of Active Compounds

Active compounds as described herein can be covalently coupled to substrates. Examples of substrates include solid supports and polymers. The polymers, typically organic polymers, may be in solid form, liquid form, dispersed or solubilized in a solvent (e.g., to form a coating composition as described above), etc. The solid support may include the substrate examples as described above to be coated with or treated with active compounds of the invention.

Covalent coupling can be carried out by any suitable technique. Active compounds of the present invention may be appended to a substrate via aldehyde condensation, amide or peptide bond, carbon-carbon bond, or any suitable technique commonly used in the art.

For example, the active compound of Formula (II)(a) can be covalently linked to a substrate having a carboxylic acid via peptide coupling as shown (with the dark bar representing the substrate):

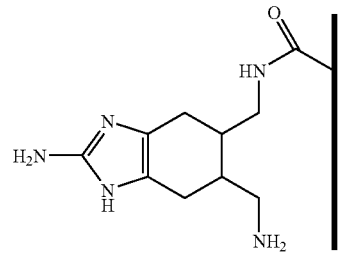

The active compound of Formula (I)(a)(i) can be covalently linked to a substrate by condensation with an aldehyde as shown:

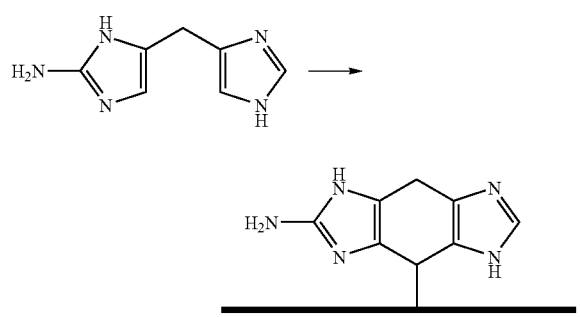

Various coupling reactions can be used to covalently link active compounds of the present invention to a substrate. Examples of coupling reactions that can be used include, but are not limited to, Hiyama, Suzuki, Sonogashira, Heck, Stille, Negishi, Kumada, Wurtz, Ullmann, Cadiot-Chodkiewicz, Buchwald-Hartwig, and Grignard reactions. For example, an active compound of Formula (I)(a)(iv) that is substituted with a halide (e.g. bromo or chloro) can be coupled to a substrate via a Heck reaction as shown:

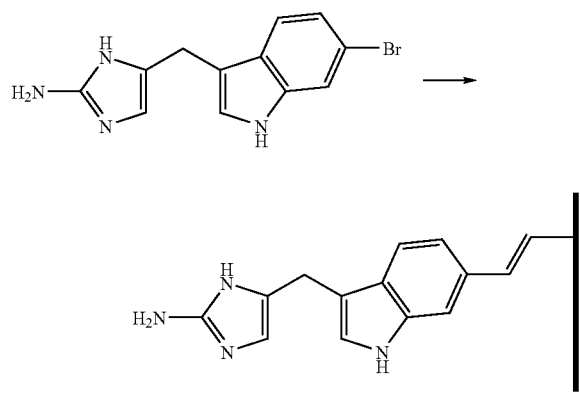

This listing of examples of reactions that can be used to append active compounds of the present invention to a substrate is not intended to be exhaustive. Those skilled in the art will readily appreciate various other methods of carrying out these teachings. Further examples and explanations of these types of reactions can be found in U.S. Pat. No. 6,136,157 (Lindeberg et al.) and U.S. Pat. No. 7,115,653 (Baxter et al.), which are each hereby incorporated by reference in their entirety.

Some aspects of the present invention are described in more detail in the following non-limiting examples.

EXAMPLE 1

Inhibition of *Pseudomonas aeruginosa* biofilm formation. A compound of Formula (II)(a)(i) ("compound 1") was synthesized in 10 linear steps, outlined in Scheme 1. Diethyl fumarate and 1,3-butadiene were subjected to a [4+2] cycloaddition to yield the Diels-Alder adduct 2. The diester 2 was then reduced with lithium aluminum hydride (LiAlH$_4$) to yield diol 3. The diol was then treated with mesityl chloride (MsCl) to generate the corresponding bis-mesylate 4 that was then refluxed with sodium azide (NaN$_3$) to yield di-azide 5. We then epoxidized 5 with meta-chloroperoxybenzoic acid (m-CPBA) at room temperature in the absence of ambient light to generate 6. Epoxide 6 was then treated with NaN$_3$ and sulfuric acid H$_2$SO$_4$ in refluxing ethanol to yield the azidoalcohol 7 that was subsequently subjected to hydrogenating conditions in the presence of di-tert-butyl dicarbonate (Boc$_2$O). The tri-Boc protected amino alcohol 8 was then oxidized with pyridinium chlorochromate to generate ketone 9. Quantitative Boc-deprotection with TFA, followed by conversion to the HCl, and finally condensation of our α-aminoketone with cyanamide generated 1 in 7.5% overall yield from commercially available starting materials.

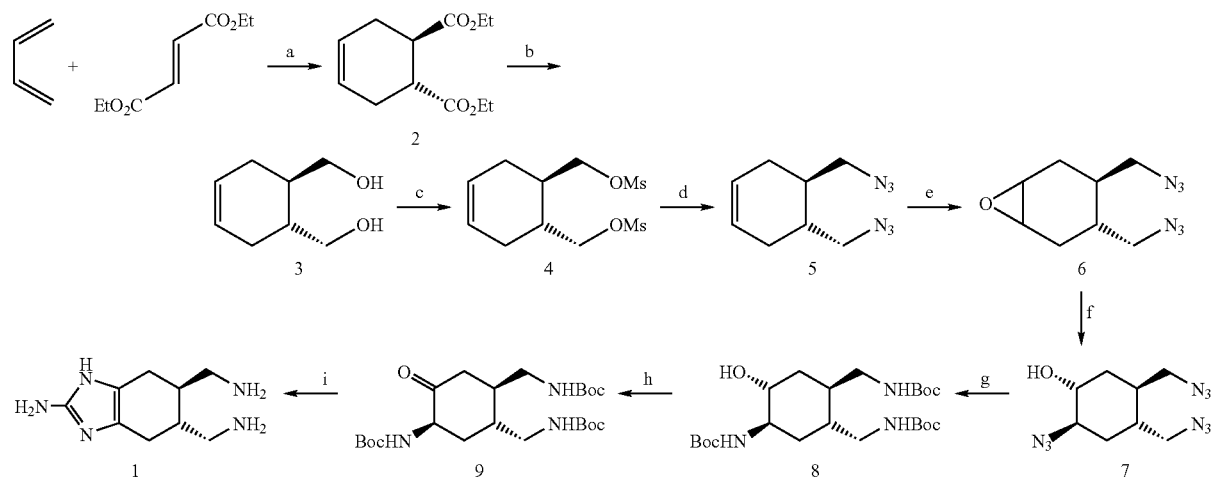

Scheme 1. Synthesis of compound 1.

Reaction conditions: a. Toluene, reflux, 24 hours; b. lithium aluminum hydride, 0° C., diethyl ether; c. mesityl chloride, dichloromethane, diisopropylethyl amine; d. sodium azide, DMF, 100° C.; e. m-CPBA, dichloromethane, room temperature, 24 hours; f. sodium azide, H$_2$SO$_4$, ethanol, reflux; g. H$_2$, 10% Pc/C, DMF, Boc$_2$O; h. PCC, methylene chloride; i. TFA/methylene chloride, then HCl/MeOH, then Cyanamide/H$_2$O/pH = 4.5, 90° C., 3 hours.

Control compounds were also synthesized (Scheme 2). Starting with 2-aminoimidazole 1, we acylated the 2-amino position of the 2-aminoimidazole ring with an acyl pyrrole moiety to yield compound 10. This was designed to test the importance of the 2-AI ring as the critical pharmacophore that imparted biological activity on our molecule. We also synthesized the diastereomer of compound 1, where one of the chiral centers was inverted. This diastereomer, 11, was synthesized using the same synthetic sequence that we delineated above with the exception that we employed maleic anhydride instead of diethyl fumarate in the first step of the synthesis.

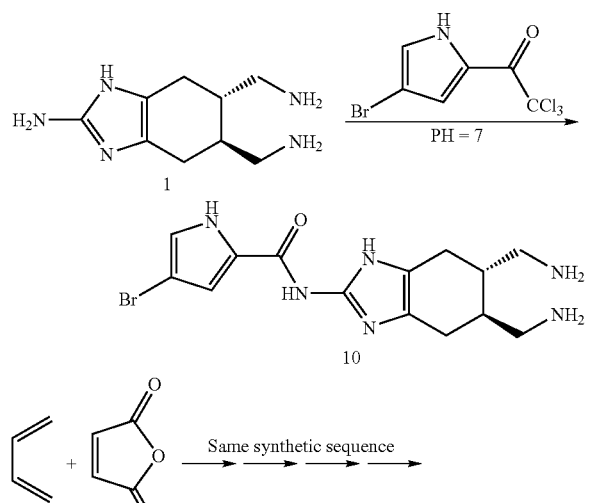

Each compound was assayed for the ability to inhibit the formation of P. aeruginosa biofilms. The 2-acetylated compound 10 was inactive in all our assays, providing evidence that the 2-aminoimidazole ring is essential for biological activity. We employed a standard crystal violet reporter assay to assess for the formation of biofilms. Briefly, P. aeruginosa strain PAO1 was allowed to form biofilms in a multi-well plate in the absence or presence of our compounds. Planktonic (or free growing) bacteria were then removed, wells washed vigorously, and crystal violet added. Crystal violet stains the remaining bacteria which, following ethanol solubilization, can be quantitated by spectrophotometry ($A_{540}$). As can be seen from FIG. 1, at 4 hours, both compounds inhibited the formation of P. aeruginosa PAO1 biofilms.

Figure 2:
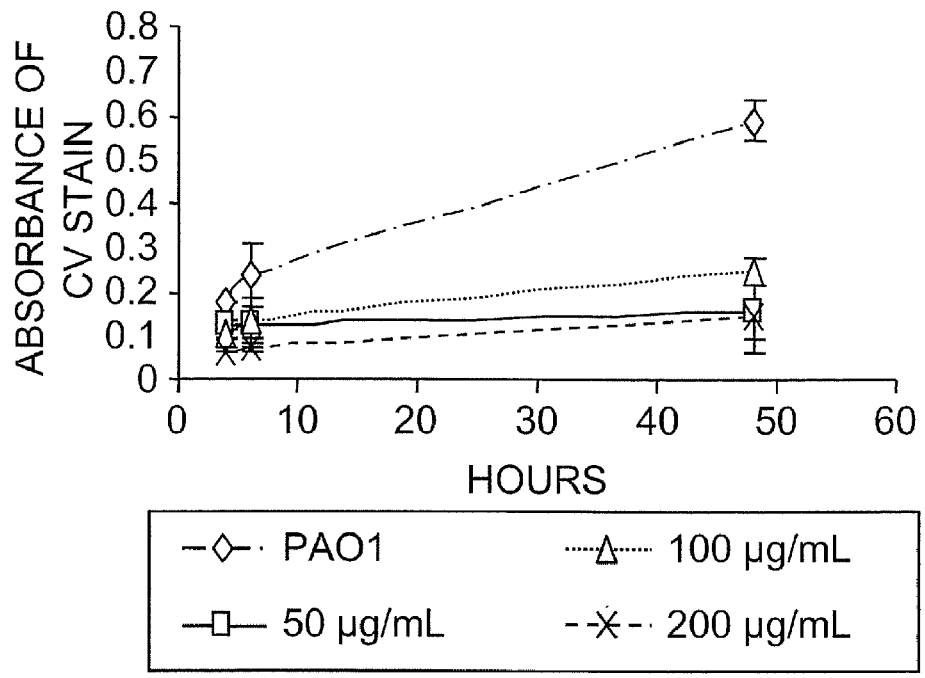
FIG. 2. Inhibition of biofilm formation by compounds 1 and 11.
Figure 2:
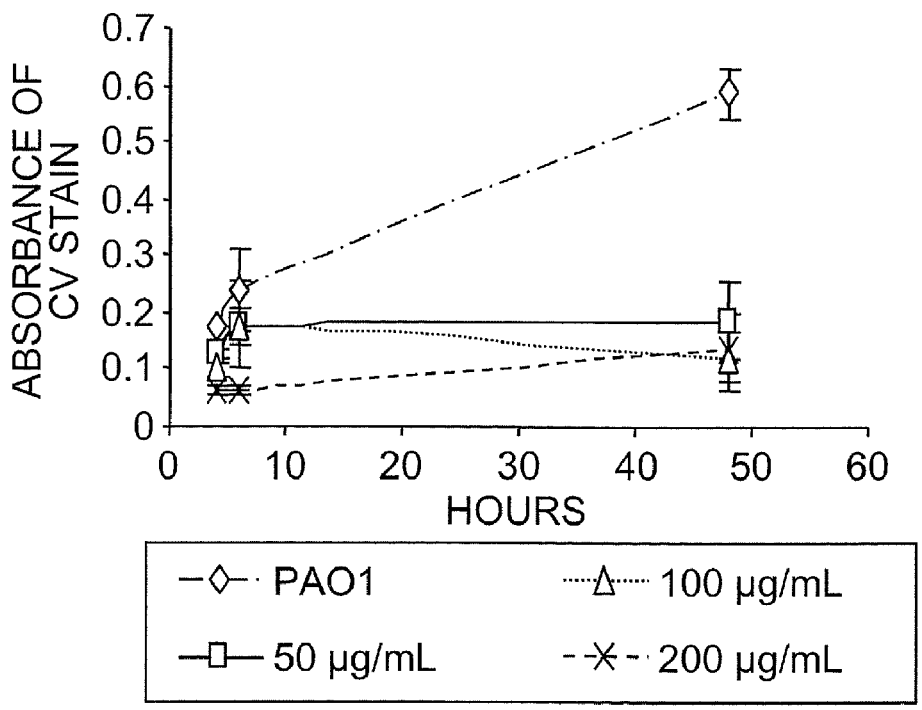

Based upon this result, we performed both a time-dependent and concentration-dependent analysis of each compound. These data are depicted in FIG. 2. As can be seen, both compounds effectively inhibit formation of P. aeruginosa biofilms at 50 µg/mL (lowest concentration tested), even at the 48-hour time point (the longest time tested).

Figure 3:
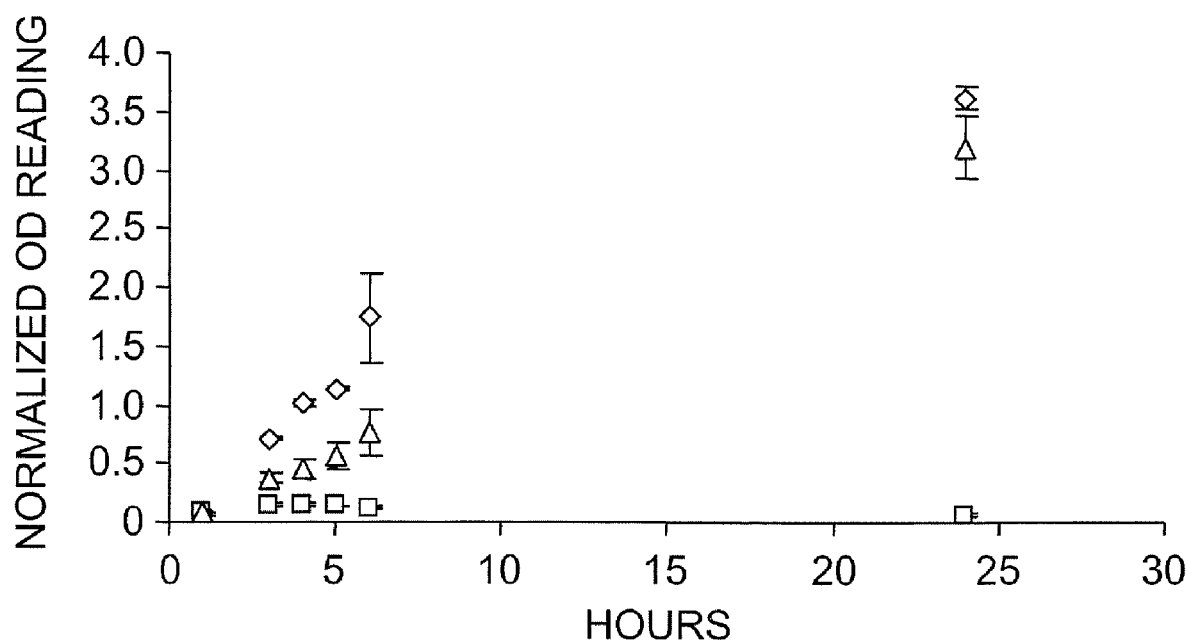
FIG. 3. Planktonic growth studies. Diamonds are growth in the absence of compound, Triangles is bacteria grown in the presence of (1), Squares depict bacterial growth in the presence of (11).

To answer the question of whether the compounds were antibiotics or true inhibitors of biofilm formation, we tested the ability of both compounds to inhibit growth of planktonic P. aeruginosa. Growth was quantitated by measuring optical density at 600 nm. As can be seen in FIG. 3, the cis-compound 11 potently inhibited the growth of planktonic bacteria, indicating that it possesses bactericidal properties and was likely inhibiting biofilm formation by killing the planktonic bacteria before biofilms were established. The trans compound 1, in contrast, marginally inhibited growth at 24 hours. Therefore, 1 appears to be inhibiting the ability of P. aeruginosa to form biofilms.

EXAMPLE 2

Active compounds were tested for inhibition of biofilm formation using various bacterial strains. Results are reported in TABLE 1. Assays were performed as reported above, with 500 µM active compound, and 24 hours. "X" denotes biofilm inhibition.

TABLE 1

| Formula | Compound | P. aeruginosa | V. Vulnificus | H. Pacifica |
|---|---|---|---|---|
| (II)(a) | 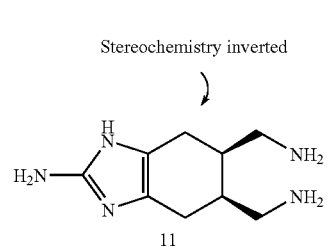 | X | | |
| (II)(a) | | X | X | X |
| (I)(a)(i) | | | X | X |

TABLE 1-continued

| Formula | Compound | P. aeruginosa | V. Vulnificus | H. Pacifica |
| --- | --- | --- | --- | --- |
| (I)(a)(iv) | | X | | X |
| (I)(a)(xviii) | | X | | X |
| (I)(a)(xviii) | | | | X |
| (I)(a)(xviii) | | | | X |
| (V) | | | X | |
| (I) | | | | X |

EXAMPLE 3

Figure 4:
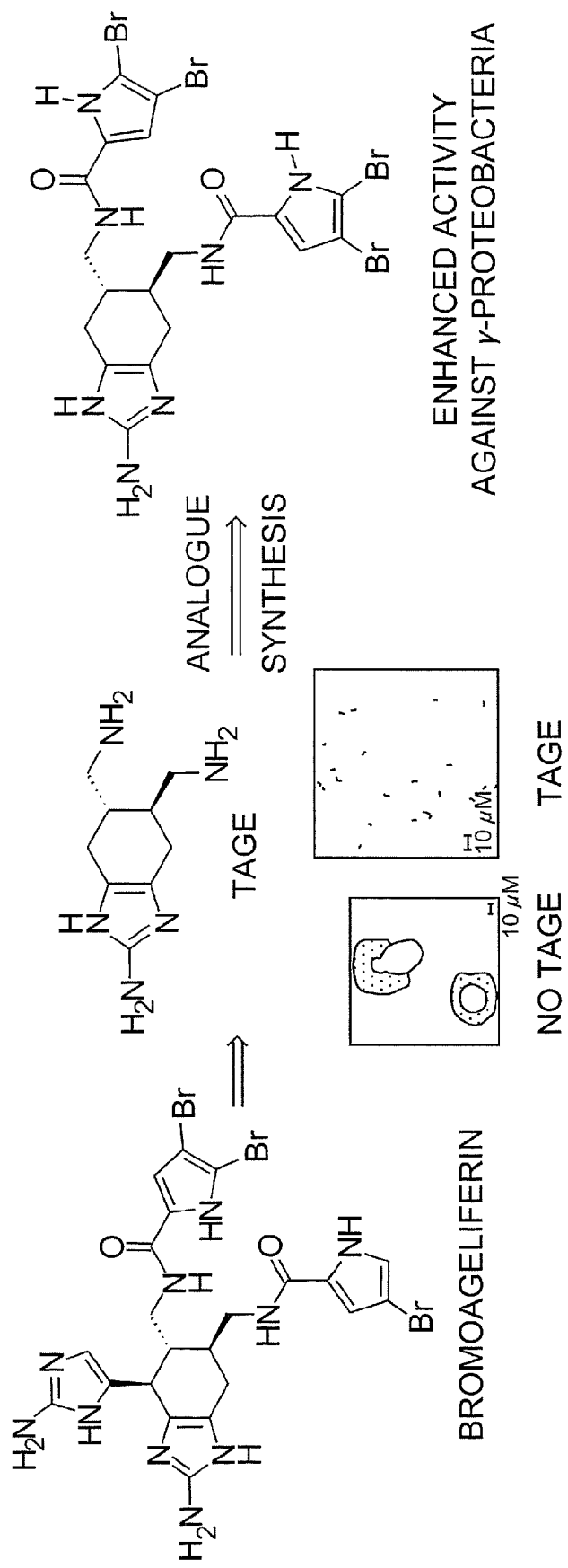
FIG. 4. Bromoageliferin, TAGE and the TAGE derivative BromoTAGE.

Identification of a bicyclic 2-aminoimidazole derivatives that inhibit and disperse bacterial biofilms. In Example 1 above it was demonstrated the synthesis of a small molecule, denoted TAGE (trans-bromoageliferin analogue), based on the natural product bromoageliferin, and demonstrated that TAGE had anti-biofilm activity against *Pseudomonas aeruginosa* (see FIG. 4). It is demonstrated by the present Example that TAGE: 1) does not have selective toxicity against cells within the biofilm state, 2) will inhibit biofilm development under flow conditions, indicating that the CV staining protocol correlates with the ability to be active under biomimetic conditions, and 3) TAGE will disperse preformed *P. aeruginosa* biofilms. It is also demonstrated that TAGE is not cytotoxic. Further analogue development (see FIG. 4) has identified compounds that are exceedingly effective as biofilm inhibitors against the γ-proteobacteria in this study (PAO1, PA14, PDO300, and *A. baumannii*). Against the β-proteobacterium RB50 and the gram-positive bacterium *S. aureus*, substantial ability to inhibit biofilm development is also observed; however, some of this activity is attributed to microbicidal activity. The TAGE derivatives presented in this study, however, do not disperse pre-formed biofilms with the same efficiency as TAGE.

Figure 5:
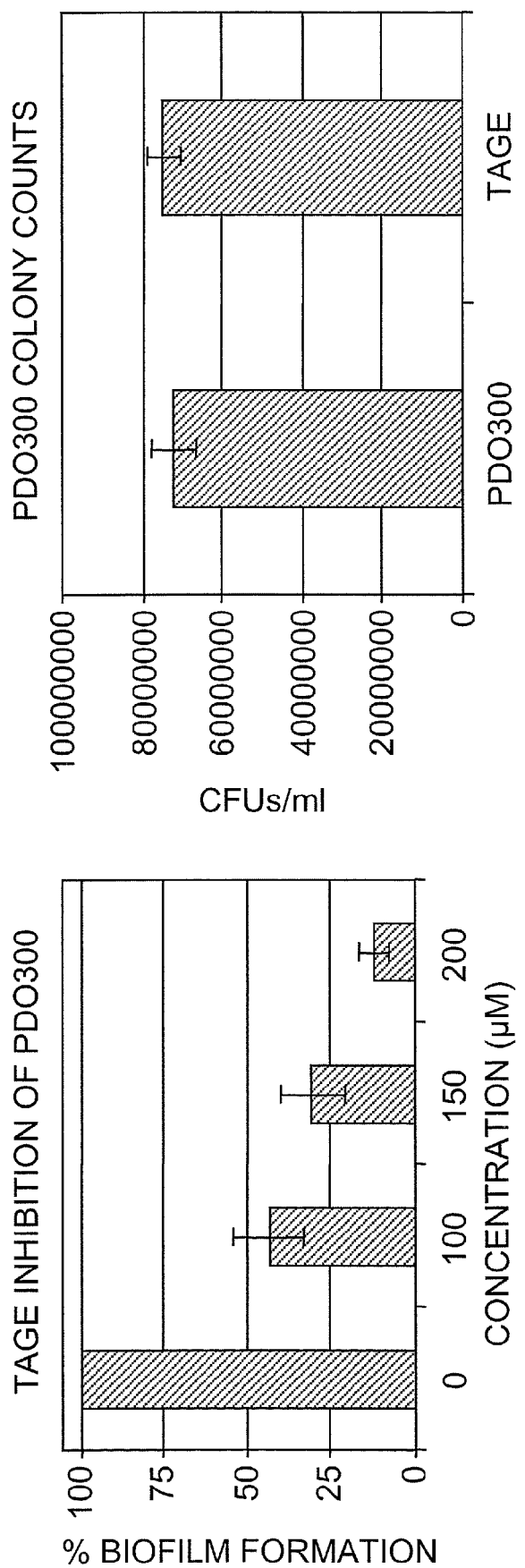
FIG. 5. Inhibition of PDO300 biofilms with TAGE. Left, dose-response of [% Biofilm Formation] vs. TAGE concentration. Right, colony counts of PDO300 grown in the absence and presence of TAGE (88 µM).

The first issue addressed was the ability of TAGE to inhibit the formation of a biofilm from mucoid variants of *P. aeruginosa*. After a CF patient is colonized by *P. aeruginosa*, the bacterium undergoes a phenotypic shift from a non-mucoid to a mucoid form (Govan et al., *Microbiol. Rev.*, 1996, 60, 539;

Ramsey et al., *Mol. Microbiol.*, 2005, 56, 309). The mucoid form is characterized by the overproduction of alginate in the extracellular polymeric substance (EPS) (Ramsey et al., *Mol. Microbiol.*, 2005, 56, 309). PDO300 was employed to assay if TAGE would inhibit the formation of mucoid biofilms. PDO300 is a well-characterized mucoid strain of *P. aeruginosa* that is genotypically identical to PAO1 except for the mucA mutation that converts the bacterium to the mucoid phenotype (Mathee et al., *Microbiology*, 1999, 145, 1349). PDO300 biofilms were allowed to develop in a 96-well plate in the absence or presence of TAGE. After 24 hours, the media and planktonic bacteria were removed, the wells were washed vigorously, and crystal violet was added. Crystal violet stains the bacterial biofilm that forms on the inside wall of the well at the air/liquid interface, which, following ethanol solubilization, can be quantitated by spectrophotometry ($A_{540}$) (O'Toole et al., *Mol. Microbiol.*, 1998, 30, 295). Using various TAGE concentrations, a dose-response curve of [TAGE] vs. (% biofilm inhibition) was generated and it was determined that TAGE has an $IC_{50}$ of 88 µM against PDO300 (FIG. 5). Growth curves (not shown) and colony counts (FIG. 5) indicated that TAGE lacked bactericidal activity against PDO300.

The second issue addressed was the effect that TAGE had upon the bacterial biofilm. Specifically, the effect TAGE had upon biofilm architecture and the effect TAGE had upon cell viability within a biofilm were analyzed. The studies reported above demonstrated that TAGE was able to significantly reduce biofilm mass at concentrations (300 µM) that induced no microbicidal activity against planktonic bacteria. However, biofilm mass was measured by crystal violet (CV) staining and gives no indication of the topology of the biofilm. CV staining simply indicates the total amount of biomass that resides within the biofilm. Furthermore, given that there is differential gene expression between bacteria growing in a biofilm and planktonic bacteria, (Costerton et al., *Science*, 1999, 284, 1318.) it was investigated if TAGE had selective microbicidal activity against biofilm bacteria. To address these points, PAO1 biofilms were grown on a glass cover slip for 48 hours in the absence or presence of 100 µM TAGE. Media and planktonic bacteria were then washed from the cover slips and live/dead cell staining was performed. Visualization via confocal microscopy was then used to assess both the relative ratio of live/dead cells within the biofilm as well as differences in architecture between the untreated and TAGE-treated samples. A significant reduction in the biofilm biomass and biofilm architecture was observed with TAGE-treated biofilms in comparison to biofilms grown in the absence of compound (not shown). Furthermore, the ratio of live vs. dead cells in TAGE-treated vs. untreated cells was similar, indicating that TAGE lacks bactericidal activity against bacteria within a biofilm (not shown).

Next, the ability of TAGE to operate under flow conditions was assessed. Biofilms formed under flow conditions are generally accepted as better models of biofilms that form in vivo. Christensen et al., *Methods Enzymol.*, 1999, 310, 20. The bacterial strain PAO1:gfp was used to assess biofilm development under flow conditions. PAO1:gfp contains an integrated green fluorescent protein gene in the PAO1 genome that allows bacterial visualization via fluorescence. In two separate flow vessels, PAO1:gfp was allowed to attach, under turbulent flow, for 1 hour. It is at this point that irreversible attachment occurs. After the attachment phase, media only was flowed over one of the vessels while media-containing 300 µM TAGE was flowed over the other vessel. Each flow was maintained for 24 hours. At the end of 24 hours, each vessel was visualized by confocal microscopy. These results clearly show that TAGE is active under continuous flow conditions as evidenced by the severe reduction of fluorescence. In addition, the use of the CV staining assay that was employed in the previous study gave almost identical results compared with the results obtained under flow conditions.

Mammalian cytotoxicity of TAGE was also investigated. Bromoageliferin, a natural sponge compound, is known to modulate the activity of calcium channels. U. Bickmeyer, *Toxicon*, 2005, 45, 627. GH4Cl rat pituitary cells and N2A mouse neuroblastoma cells were chosen for cytotoxicity screening. These cell lines are utilized for evaluating toxicity of marine natural products. Burkholder et al., *Proc. Natl. Acad. Sci. USA*, 2005, 102, 3471. Van Dolah et al., *Nat. Toxins*, 1994, 2, 189. Each cell line was plated at $3 \times 10^4$ cells/well in 96-well plates in 50 µl of Dulbeccos Modified Eagles Medium (DMEM). The cells were allowed to adhere at 37° C. in 5% $CO_2$ for 4 hours before use. 4 µl of test fractions were added and the cells incubated for 18 hours. Cell viability was assessed through an MTT-based colorimetric assay. All cells remained viable in the presence of up to 600 µM of our compounds, which indicates a lack of cytotoxicity.

Figure 6:
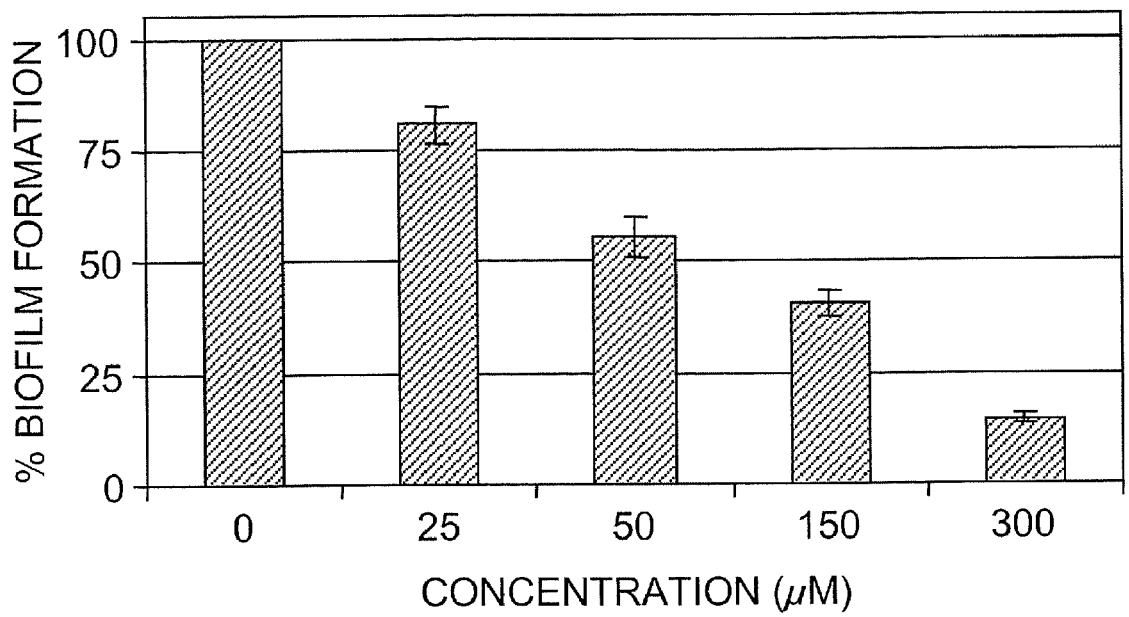
FIG. 6. Representative dose-response for PAO1 dispersion with TAGE.

One aspect associated with small molecule modulation of biofilm development is the ability to disperse a pre-formed biofilm. There have only been a limited number of examples in the literature of molecules that disperse bacterial biofilms. Banin et al., *Appl. Environ. Microbiol*, 2006, 72, 2064. L. M. Junker and J. Clardy, *Antimicrob. Agents Ch.*, 2007, 51, 3582. Boles et al., *Mol. Microbiol.*, 2005, 57, 1210. TAGE was assayed for its ability to disperse pre-formed PAO1 and PA14 biofilms. Each bacterial strain was allowed to form biofilms in a microtiter well for 24 hours in the absence of compound. At the end of 24 hours, the media containing the planktonic bacteria was removed from each well and either media alone or media containing TAGE was added. After 24 hours, all the wells were washed vigorously to remove media and planktonic bacteria, and then were stained with crystal violet to quantify the amount of remaining biofilm. Representative PAO1 results are depicted in FIG. 6. TAGE was able to disperse PAO1 with an $EC_{50}$ of 82 µM and PA14 biofilms with an $EC_{50}$ of 114 µM.

Given the TAGE's ability to inhibit and disperse *P. aeruginosa* biofilms, the activity of TAGE against other opportunistic bacteria, *Acinetobacter baumannii*, *Bordetella bronchiseptica*, and *Staphlococcus aureus*, was investigated. *A. baumannii* is another opportunistic γ-proteobacterium that has become a severe threat over the past decade due to its exceptional and increasing multi-drug resistance. M. E. Falagas and E. A. Karveli, *Clin. Microbiol Infect.*, 2007, 13, 117. *B. bronchiseptica* is a β-proteobacterium that is frequently isolated from mammalian respiratory tracts. P. A. Cotter and J. F. Miller, *Mol. Microbiol.*, 1997, 24, 671. *S. aureus* is a biofilm-forming gram-positive bacterium that is frequently associated with nosocomial infections and is becoming an increasing threat due to its acquisition of methicillin and vancomycin resistance. TAGE had no effect on the ability of *A. baumannii, B. bronchiseptica,* or *S. aureus* to form biofilms at concentrations up to 600 μM.

Three TAGE derivatives were synthesized that possessed an acylpyrrole ring in a manner that mimics the ageliferin natural products (Scheme 3).

Scheme 3. Synthesis of advanced ageliferin analogues.

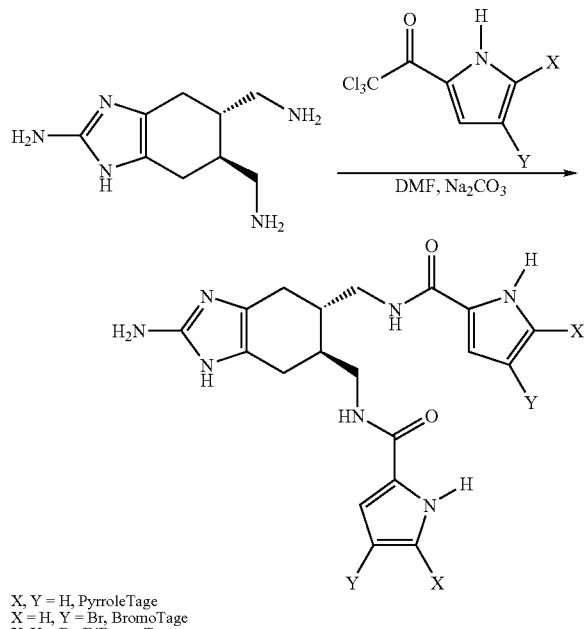

X, Y = H, PyrroleTage
X = H, Y = Br, BromoTage
X, Y = Br, DiBromoTage

Previous studies have indicated that the incorporation of an acyl pyrrole moiety within the 2-aminomidazole scaffold dramatically increasing anti-biofilm activity. These pyrrole 2-aminoimidazole structures showed anti-biofilm activity that exceeded the anti-biofilm activity of TAGE and CAGE, while their parent 2-aminoimidazole substructure, 4-(3-aminopropyl)-2-aminoimidazole, lacked anti-biofilm activity. Furthermore, we have also demonstrated that activity is not solely due to the acyl pyrrole, as simple acyl pyrrole derivatives had no inhibitory effect on the ability of bacteria to form biofilms. To synthesize the three TAGE derivatives, TAGE was first synthesized on multi-gram scale using the synthetic approach we outlined previous. TAGE was then coupled to the appropriate the appropriate acyl pyrrole trichloromethyl ketone to generate the 3 TAGE derivatives (PyrroleTAGE, BromoTAGE, and DibromoTAGE).

Figure 7:
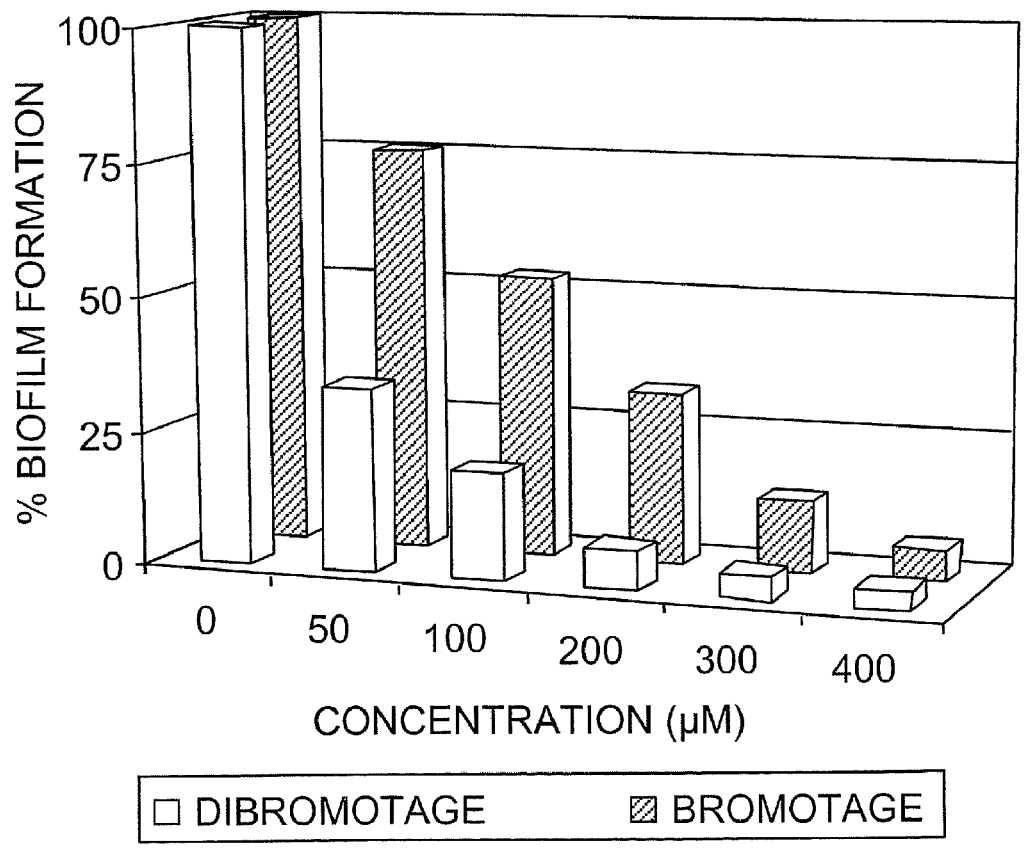
FIG. 7. Dose-response comparison for BromoTAGE and DibromoTAGE against *A. baumannii*.

Screens of the three compounds were performed against *A. baumannii* and *B. bronchiseptica*. These strains had showed resistance to TAGE. PyrroleTAGE showed only slight inhibitory activity (23%) against *A. baumannii* at the highest concentration tested (400 μM). The activity was encouraging because TAGE showed no activity at more than twice this concentration. As noted, incorporation of a bromine atom within the acyl pyrrole moiety of the 2-aminoimidazole scaffold might greatly increase activity. In this case, BromoTAGE revealed a significant increase in anti-biofilm activity, and it was determined that the $IC_{50}$ value for inhibition against *A. baumannii* was 108 μM. DibromoTAGE was shown to be even a more potent inhibitor against *A. baumannii* with an $IC_{50}$ value of 15.5 μM. A comparison of the dose-responses for Bromo- and DibromoTAGE is depicted in FIG. 7. These results indicated that the number of bromines on the acyl pyrrole moieties influenced the inhibitory activities of these TAGE derivatives on *A. baumannii* biofilm formation. Growth curves were measured in the presence or absence of each compound, and it was noted that there was no reduction on planktonic growth (not shown). This indicated that the mechanism of biofilm inhibition with these TAGE derivatives was not due to microbicidal activity.

Figure 8:
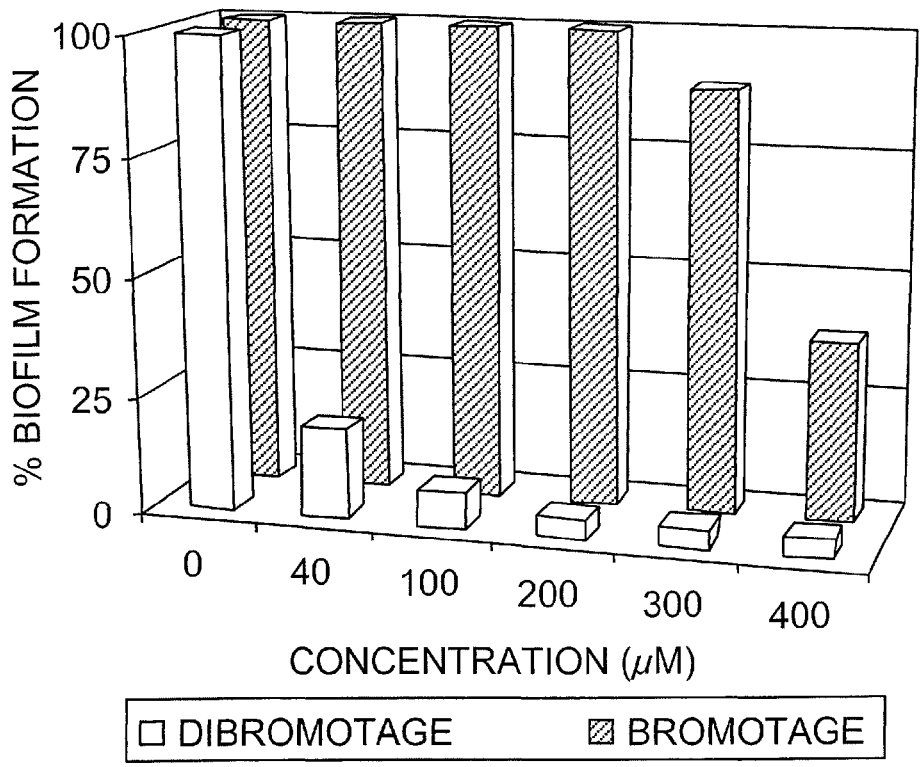
FIG. 8. Dose-response comparison for BromoTAGE and DibromoTAGE against RB50.

Next, the ability of each TAGE derivative to inhibit the formation of *B. bronchiseptica* biofilms (strain Rb50) was assayed to see if the compounds could inhibit the formation of biofilms across this bacterial order. PyrroleTAGE showed no inhibitory activity against Rb50 at 500 μM. However, BromoTAGE showed activity at high concentrations, and further investigation determined an $IC_{50}$ value for inhibition of Rb50 to be 385 μM. DibromoTAGE was more potent and had an $IC_{50}$ value of 27 μM (dose-response comparison depicted in FIG. 8). Comparison of the RB50 growth curves generated in the absence and presence of the TAGE derivatives, however, revealed that the compounds were microbicidal, and most likely exerting their anti-biofilm effects through a bacterial static mechanism.

Next, the anti-biofilm effects of our TAGE derivatives against *Staphylococcus aureus*, a gram-positive bacterium that is known to form biofilms, were examined. As we observed with TAGE. PyrroleTAGE showed no inhibitory activity at concentrations up to 600 μM. BromoTAGE and DibromoTAGE, however, revealed $IC_{50}$ values of 21.0 μM and 14.0 μM, respectively (not shown). Analysis of the growth curves generated in the absence and presence of BromoTAGE and DibromoTAGE revealed that both compounds are slightly toxic and have an effect on growth and overall cellular density after 24 hours (not shown). However, these compounds were not as toxic to *S. aureus* as they were to RB50.

Figure 9:
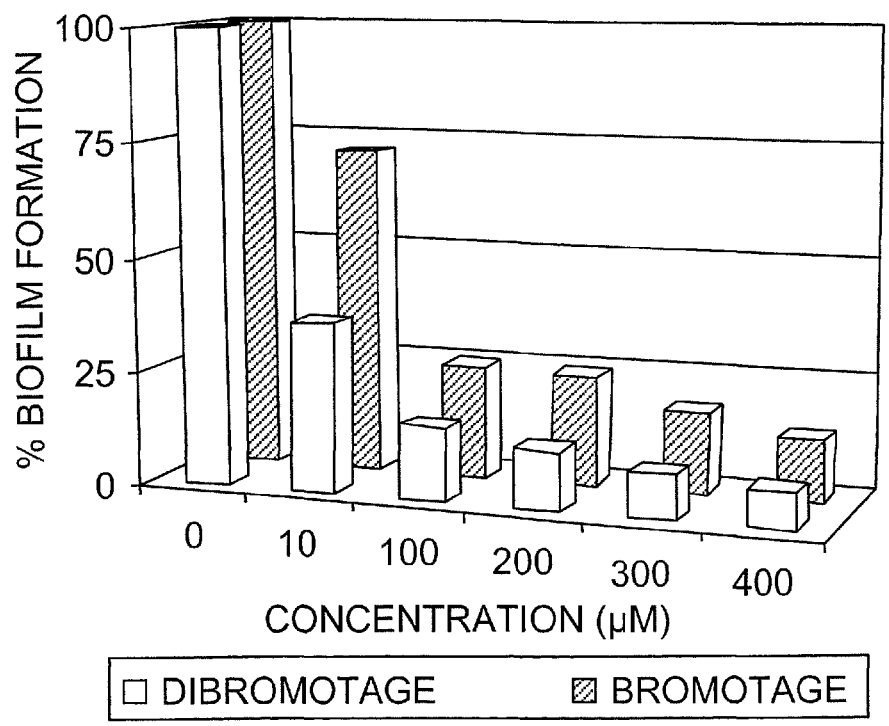
FIG. 9. Dose-response comparison for BromoTAGE and DibromoTAGE against PAO1.

Given the increase in activity by both BromoTAGE and DibromoTAGE, it was determined if the TAGE derivatives also had enhanced activity against *P. aeruginosa*. Previous results had shown that TAGE was able to inhibit the formation of PAO1 biofilms with an $IC_{50}$ of 100 μM. As with all of the previous studies with PyrroleTAGE, no inhibitory activity was observed at concentrations up to 400 μM. BromoTAGE, however, showed a 3-fold increase in activity in comparison to TAGE and revealed an $IC_{50}$ value of 32.5 μM against PAO1. Consistent with all of the anti-biofilm results from this study, DibromoTAGE gave the most significant inhibition result, and revealed an $IC_{50}$ value of 1.77 μM. A representative dose-response comparison is depicted in FIG. 9. Growth curves and colony counts of PAO1 grown the presence and absence of BromoTAGE and DibromoTAGE indicated that both compounds lacked microbicidal activity against planktonic growth. (not shown).

DibromoTAGE was also screened against PDO300 and PA14 to compare to the inhibitory activity of TAGE against these strains. Against PDO300, DibromoTAGE demonstrated enhanced activity with an $IC_{50}$ value of 2.47 μM, while against PA14 DibromoTAGE's $IC_{50}$ value was determined to be 12.0 µM (not shown). In comparison to TAGE, this represents a 35-fold increase in activity against PDO300 and a 16-fold increase in activity against PA14. Growth curves and colony counts demonstrated that DiBromoTAGE is not toxic to planktonic cells (not shown).

Finally, each of the TAGE derivatives were assayed for their ability to disperse pre-formed biofilms. The increase in anti-biofilm activity that we observed for inhibiting the development of bacterial biofilms did not translate into increased dispersion activity. At the highest concentration tested against PAO1 (400 µM), no dispersion was observed by any of the derivatives. Some minimal dispersion activity against *A. baumannii* biofilms (20-30% at 400 µM) was observed with Bromo- and DiBromoTAGE, but more extensive dispersion was not noted at higher concentrations. While not wishing to be bound by any particular theory, it is hypothesized that the failure of these derivatives to effectively disperse biofilms, in contrast to TAGE, might be due to impeded diffusion through the biofilm matrix.

In conclusion, small molecules were synthesized and studied for their ability to modulate biofilm development. These compounds were shown to be exceedingly effective as biofilm inhibitors against the γ-proteobacteria in this study (PAO1, PA14, PDO300, and *A. baumannii*). Against the β-proteobacterium RB50 and the gram-positive bacterium *S. aureus*, a substantial ability to inhibit biofilm development was observed; however microbicidal activity was also observed. In all cases in this study, an increase in activity was correlated to increased bromine content on the pyrrole moiety. The TAGE derivatives, however, do not disperse pre-formed biofilms with the same efficiency as TAGE. As a core scaffold, it has also been demonstrated that TAGE will inhibit biofilm development under flow conditions, indicating that the CV staining protocol correlates with the ability to be active under biomimetic conditions. Toxicity work indicates that TAGE is devoid of cytotoxicity, giving these compounds a promising combination of activity and lack of toxicity.

Experimental. All $^1$H NMR (300 MHz) and $^{13}$C NMR (75 MHz) spectra were recorded at 25.0° C. on a Varian Mercury spectrometer. Chemical shifts (δ) are given in ppm relative to tetramethylsilane or the respective NMR solvent. Abbreviations used are s=singlet, m=multiplet. High resolution ESI was used to determine molecular weight of new compounds in this study. Silica gel (40 µm average particle size) was used for column chromatography. All reagents were used without further purification from commercial sources unless otherwise noted.

Static Biofilm Inhibition Assay: An overnight culture of the bacterial strain being screened against was subcultured at an $OD_{600}$ of 0.1 into the media used (listed below with strain) and then pippetted into test tubes along with a predetermined concentration of our compound of interest. Test tubes were then poured into tilted Petri dishes and 100 µL of media, strain and compound were then transferred into 96-well PVC microtiter plates. These microtiter plates were then covered, wrapped in Saran™ Wrap polyethylene film (S.C. Johnson, Racine, Wis.) and allowed to incubate at 37° C. for 24 hours. After that time, the medium was discarded and the plates were thoroughly washed with water. The remaining biofilm that was formed during incubation was stained with 100 µL of a 0.1% crystal violet solution and allowed to incubate at room temperature for 30 minutes. After 30 minutes, the crystal violet was discarded and washed thoroughly again with water. The remaining crystal violet that had stained the biofilm in the inside walls of the 96-well PVC plates was solubilized with 200 µL of 95% ethanol. The quantification of biorilm formation was accomplished by transferring 125 µL of the ethanol solution into a polystyrene microtiter dish, which was read by spectrophotometry ($A_{540}$). After the background has been subtracted from each row, a percent inhibition can be calculated by dividing the amount of crystal violet in wells that contained compound by the amount of crystal violet in wells that contained bacteria only. Each concentration reported during the course of this study was repeated two to five times with each of those biofilm inhibition assays being done in 6 replicates each.

| Bacterial strains/media used: |
| --- |
| PAO1 - LBNS |
| PA14 - LBNS |
| PDO300 - LBNS |
| *Acinetobacter Baumannii* (ATCC 19606) - LB |
| *Staphylococcus aureus* (ATCC 29213) - TSB with 0.3% glucose |
| Rb50 - SS media/100X supplement (10 µL/mL of SS media). |

Static Biofilm Dispersion Assay: An overnight culture of either PAO1 or PA14 was subcultured at an $OD_{600}$ of 0.5 into LBNS and aliquoted (100 µL) into the wells of a 96-well PVC microtiter plate. The microtiter plates were then covered and wrapped with Saran™ Wrap polyethylene film before being incubated at room temperature under stationary conditions for 24 hours to allow the formation of biofilms. After 24 hours, the medium was discarded and the plates were thoroughly washed with water leaving only the preformed biofilm on the inside of the PVC wells. LBNS alone was added for the control and LBNS containing a predetermined concentration of the compound of interest was then pippetted into the wells (100 µL). The plates were then covered and wrapped in Saran™ Wrap polyethylene film and incubated at 37° C. for an additional 24 hours after which the media and planktonic cells were discarded and washed with water. The wells were then stained with 100 µL of a 0.1% crystal violet solution and allowed to sit for 30 minutes at room temperature. The crystal violet solution was then discarded from the wells and washed with water thoroughly. The remaining crystal violet was solubilized with 200 µL of 95% ethanol. The quantification of remaining biofilm was accomplished by transferring 125 µL of the ethanol solution into a polystyrene microtiter dish, which was read by spectrophotometry ($A_{540}$). Percent dispersion was calculated in the same manner as percent biofilm inhibition described previously in this experimental section.

General Procedure for Acylation of TAGE. DMF (2 or 3 ml) was added to a reaction vial containing TAGE•3 HCl along with $Na_2CO_3$ (5 equivalents), and the respective brominated or non-brominated 2-(trichloroacetyl)-pyrrole variant (2.1 equivalents). The reaction was then allowed to stir under an argon atmosphere at 50° C. overnight. Upon completion of the reaction, the reaction vial was removed from the heat source and concentrated under reduced pressure vacuum. The resulting residue was purified by flash column chromatography (utilizing a gradient starting at 10% methanol/ammonia in DCM and increasing polarity to 40% methanol/ammonia in DCM) to give the corresponding acylpyrrole TAGE derivative. Percent yields are recorded with compound characterization below.

PyrroleTAGE—DMF (2 ml), 104.4 mg TAGE•3 HCl, 155.6 mg 2-(trichloroacetyl)-pyrrole, 183 mg $Na_2CO_3$ yielded 69 mg PyrroleTAGE as a free base after purification (53% yield). $^1$H NMR (300 Hz, DMSO-$d_6$) δ11.47 (s, 2H), δ 8.20 (s, 2H), δ 7.40 (s, 2H), δ 6.84 (s, 2H), δ 6.77 (s, 2H), δ 6.07 (s, 2H), δ 3.21 (m, 4H), δ 2.62-2.50 (m, 2H partially buried in DMSO peak), δ 2.26-2.16 (m, 4H) ppm; $^{13}$C NMR (75 Hz, DMSO-$d_6$) δ 160.8, 146.5, 126.3, 121.1, 117.6, 110.2, 108.5, 40.7, 34.3, 20.1; HRMS (ESI) calcd for $C_{19}H_{24}N_7O_2$ (MH)$^+$382.1985, found 382.1982.

BromoTAGE—DMF (2 ml), 101 mg TAGE•3 HCl, 210.7 mg 4-bromo-2-(trichloroacetyl)-pyrrole, 180 mg $Na_2CO_3$ yielded 89 mg BromoTAGE as a free base after purification (50% yield). $^1$H NMR (300 Hz, DMSO-$d_6$) δ11.91 (s, 2H), δ 8.44 (t, 2H), δ 7.42 (s, 2H), δ 6.95 (s, 2H), δ 6.91 (s, 2H), δ 3.15 (m, 4H), δ 2.60-2.50 (m, 2H partially buried in DMSO peak), δ 2.25-2.16 (m, 4H) ppm; $^{13}$C NMR (75 Hz, DMSO-$d_6$) δ 159.7, 146.5, 126.9, 121.0, 117.5, 111.9, 94.9, 40.8, 34.0, 20.1; HRMS (EST) calcd for $C_{19}H_{22}N_7O_2Br_2$ (MH)$^+$ 538.0196, found 538.0185.

DibromoTAGE—DMF (3 ml), 106 mg TAGE•3 HCl, 274 mg 4, 5-dibromo-2-(trichloroacetyl)-pyrrole, 195 mg $Na_2CO_3$ yielded 127 mg DibromoTAGE as a free base after purification (52% yield). $^1$H NMR (300 Hz, DMSO-$d_6$) δ 8.51 (t, 2H), δ 7.41 (s, 2H), δ 6.98 (s, 2H), δ 3.19 (m, 4H), δ 2.60-2.50 (m, 2H partially buried in DMSO peak), δ 2.25-2.16 (m, 4H) ppm; $^{13}$C NMR (75 Hz, DMSO-$d_6$) δ 158.9, 146.5, 128.1, 117.5, 113.1, 104.3, 97.8, 40.8, 33.9, 20.1; HRMS (ESI) calcd for $C_{19}H_{20}N_7O_2Br_4$ (MH)$^+$693.8406, found 693.8410.

EXAMPLE 4

Inhibition and dispersion of *Pseudomonas aeruginosa* biofilms with reverse amide 2-aminoimidazole oroidin analogues. The marine alkaloid oroidin along with a small library of reverse amide (RA) 2-aminoimidazoles were synthesized and assayed for anti-biofilm activity against PAO1 and PA14, two strains of the medically relevant γ-proteobacterium *Pseudomonas aeruginosa*. Analogues that contained a long, linear alkyl chain were more potent inhibitors than the natural product at preventing the formation of PAO1 and PA14 biofilms. The most active compound in the series was also shown to disperse established PAO1 and PA14 biofilms at low micromolar concentrations.

The activity of oroidin, a natural sponge compound, has been documented in a limited number of studies involving bacterial attachment and colonization. Kelly et al., *Aquat. Microb. Ecol.*, 2005, 40, 191-203. Kelly et al., *Aquat. Microb. Ecol.*, 2003, 31, 175-182. Oroidin has also been shown to inhibit biofouling driven by the marine α-proteobacterium *R. salexigens*. A. Yamada et al., *Bull. Chem. Soc. Jpn.*, 1997, 70, 3061-3069. Due to this activity and chemical simplicity, oroidin was selected as a lead compound for structure activity relationship (SAR) studies in hopes of discovering a diverse range of compounds that possess anti-biofilm properties. One intriguing approach is the reversal of the amide bond highlighted in FIG. 10, which connects the bromopyrrole tail of oroidin 4 to the 2-aminoimidazole (2-AI) head.

One of the best methods for large scale preparation of the 2-AI scaffold en route to prepare oroidin and other family members involves Akabori reduction (Na/Hg) of ornithine methyl ester 7 followed by condensation with cyanamide under pH controlled conditions. S. Akabori, *Ber. Dtsch. Chem. Ges.*, 1933, 66, 151-158. G. C. Lancini and E. Lazzari, *J. Heterocycl. Chem.*, 1966, 3, 152-&. A. Olofson et al., *J. Org. Chem.*, 1998, 63, 1248-1253; Oroidin was synthesized as reported and matched characterization data. Derivatization can then be achieved via acylation of the alkyl amine off the carbon tail with variously substituted trichloroacetyl pyrroles. However, this chemistry is plagued by severe limitations, most notably the overall lack of compatibility of this system with other trichloroacetyl esters. In addition, solubility issues of the parent 2-AI leaves much to be desired. Many attempts by our group in developing other acylation conditions that would allow for the generation of greater diversity have proven unfruitful. From a practical standpoint, purifications of intermediates bearing an unprotected 2-AI often require large amounts of methanol saturated with ammonia (MeOH/NH3), which is cumbersome to prepare and can be difficult to remove from the pure sample after column chromatography.

Figure 10:
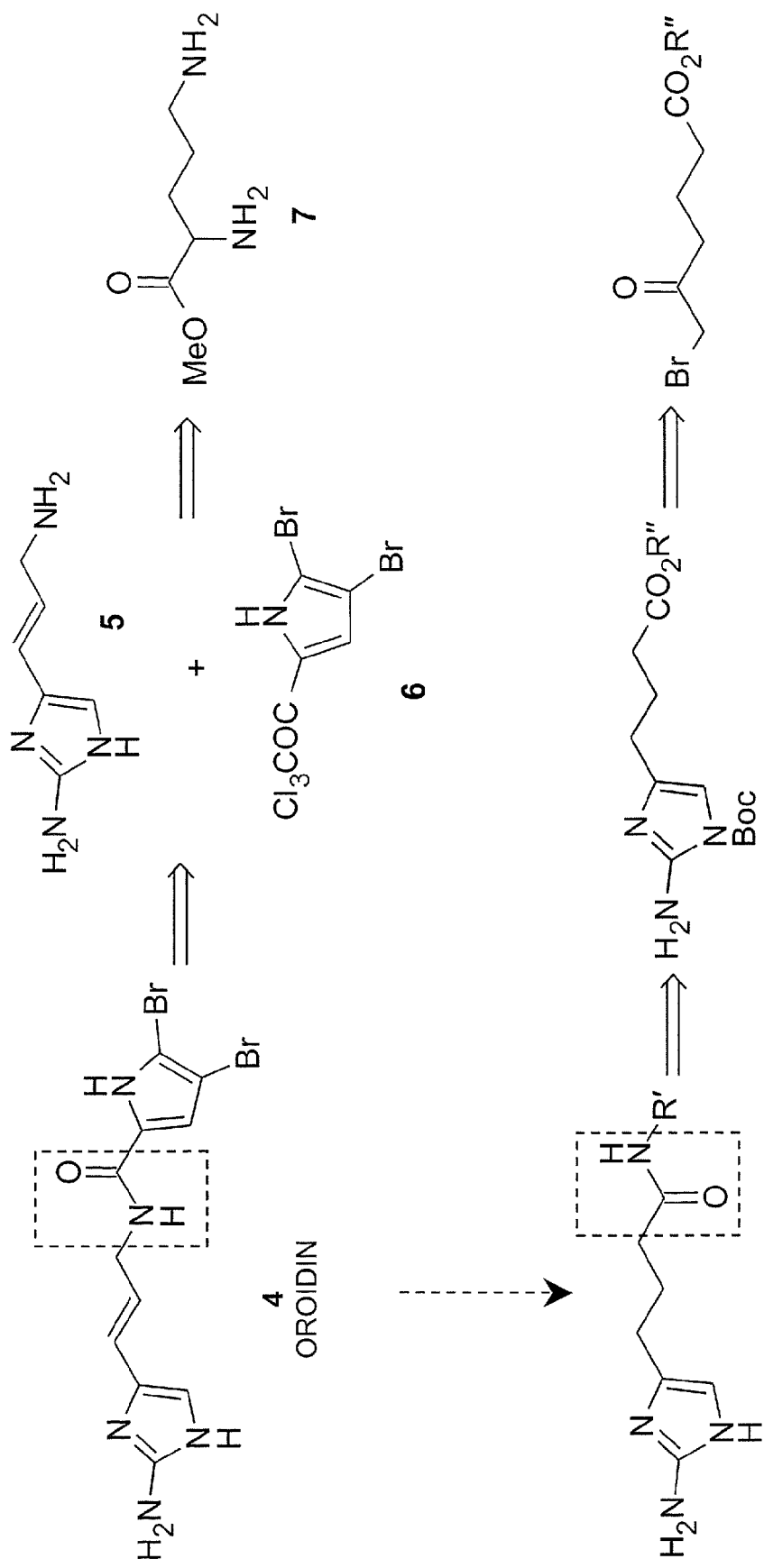
FIG. 10. Retrosynthetic analysis of oroidin and the RA scaffold.
Figure 11:
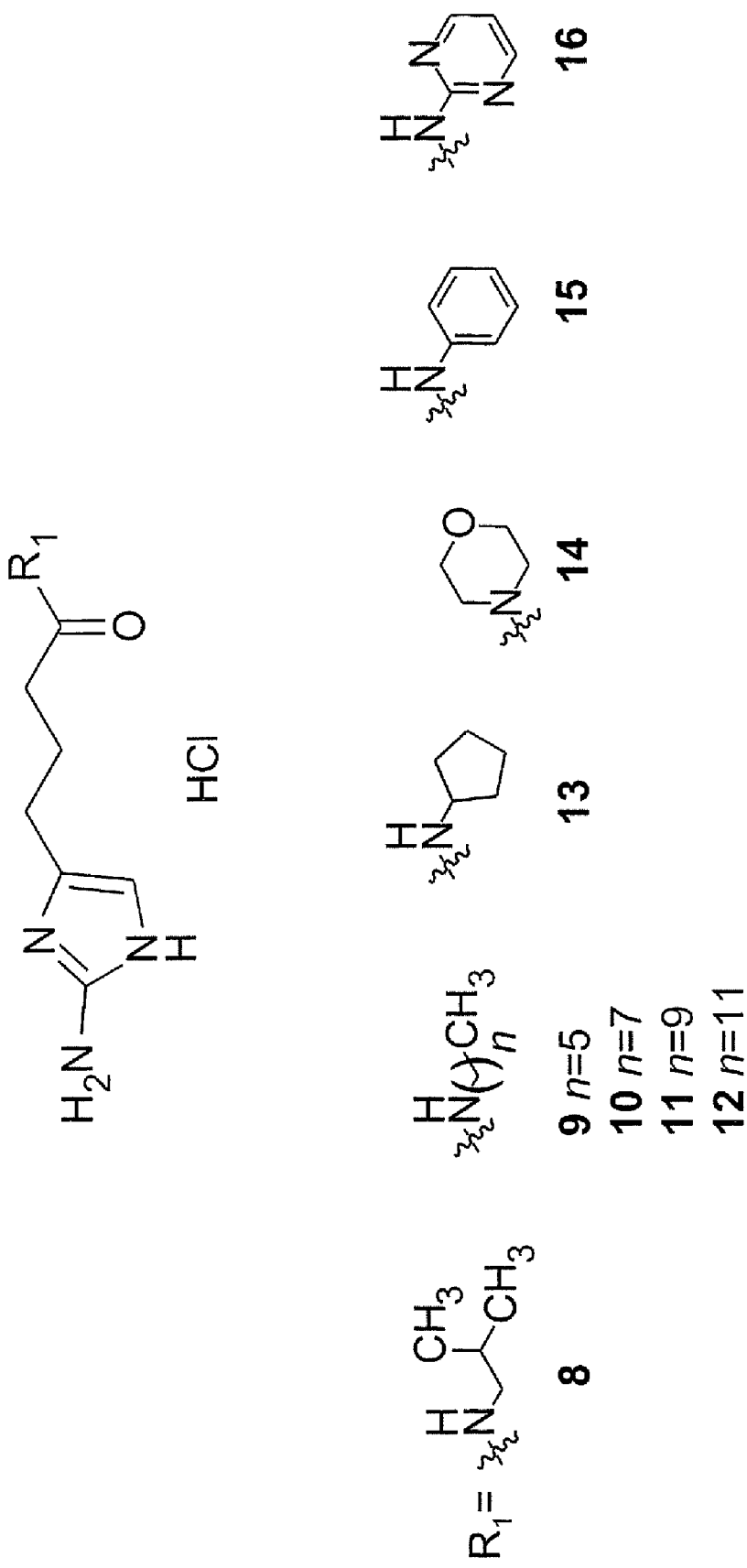
FIG. 11. Members of the reverse amide library.

Implementation of a reverse amide approach, coupled with a practical protecting group strategy, would effectively eliminate many of the aforementioned handicaps with current methods. Installation of the reverse amide bond could be obtained by direct aminolysis of an intermediate Boc-2AI alkyl ester or through couplings of a carboxylic acid (FIG. 10). These intermediates could be accessed through α-bromoketones which are obtained by diazomethane homologation with the proper acyl chloride. Additionally, significant diversity can be achieved by incorporating any commercially available amine with a common RA intermediate. Herein we report the synthesis of a focused reverse amide (RA) library (FIG. 11) and subsequent biological evaluation of the library in comparison to the natural product oroidin in the context of anti-biofilm activity of biofilms formed by the medically relevant γ-proteobacterium *Pseudomonas aeruginosa*.

Synthesis of RA Library. Scaffold synthesis began with treatment of the commercially available acid chloride 17 with diazomethane (Scheme 4). Adiyaman et al., *Tet. Lett.*, 1996, 37, 4849-4852. Quenching with concentrated HCl or HBr delivered the corresponding α-haloketones in excellent yields which were isolable by column chromatography. Installation of the protected 2-aminoimidazole moiety was achieved through a Boc-guanidine condensation in DMF at ambient temperature to yield 18. Significantly higher yields for this step were obtained when two equivalents of sodium iodide were added to the reaction mixture and represents a significant improvement over previous reports. N. Ando and S. Terashima, *Synlett*, 2006, 2836-2840. V. B. Birman and X. T. Jiang, *Org. Lett.*, 2004, 6, 2369-2371. It was also observed during this sequence that the α-bromoketone afforded higher yields than its α-chloro counterpart in the cyclization reaction.

Scheme 4. 1st Generation Synthesis of the RA Scaffold:

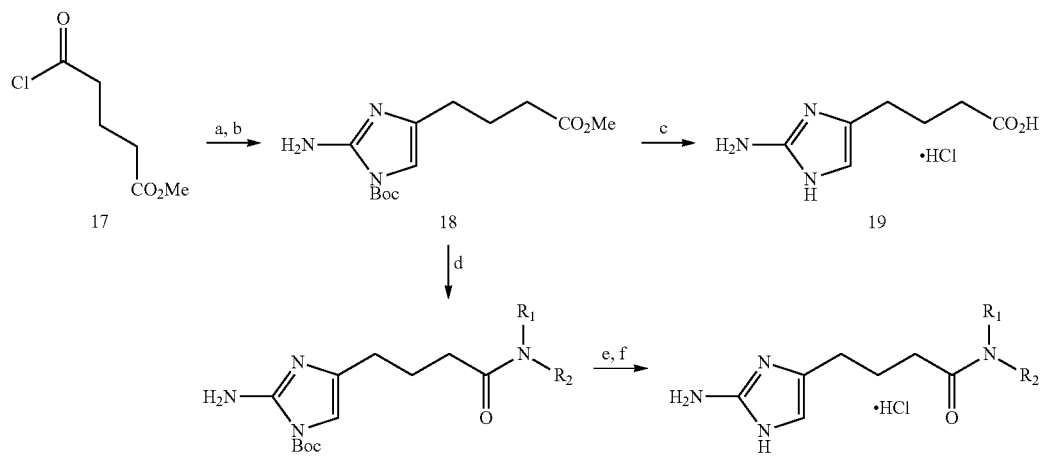

Reaction conditions: (a) i. CH$_2$N$_2$, Et$_2$O/CH$_2$Cl$_2$, 0° C. ii. conc. HCl (90%) or conc. HBr (93%) (b) Boc-guanidine, NaI, DMF, 65% (c) LiOH, MeOH/THF/H$_2$O (3:1:1) then 1N HCl to pH = 5, 94% (d) AlMe$_3$, NR$_1$R$_2$, DCE, 0° C. to 60° C. (e) TFA, CH$_2$Cl$_2$ (f) 2M HCl in Et$_2$O The first approach to the RA scaffold relied heavily on the aminiolysis of intermediate 18 since this would afford the Boc-protected RA precursors in a single synthetic step. After deprotection with TFA and HCl salt exchange, isolation of the targets would require only filtration with no need for further purification. Based upon the seminal paper published by Weinreb on the transformation, trimethylaluminum was used as the Lewis acid to affect the direct aminolysis reaction. Basha et al., *Tet. Lett.*, 1977, 4171-4174. Numerous reaction factors were taken into account such as choice of solvent, equivalents of aluminum-amine complex, reagent order of addition, time, and temperature. Despite all of the conditions scanned (data not shown), the highest yielding reaction occurred in only 55% yield when aniline was used as the amine partner. Triazabicyclo[4.4.0]dec-5-ene (TBD) was also examined as a potential catalyst to promote the direct aminolysis of ester 18. Sabot et al., *Tet. Lett.*, 2007, 48, 3863-3866. Heating both starting materials in the presence of 30 mol % of TBD in toluene at elevated temperatures for extended periods of time failed to produce any desired product as evident by TLC analysis (data not shown).

Due to the problems encountered utilizing aminolysis, we opted for a more conventional route to access the RA scaffold through the intermediacy of an activated carboxylic acid. Unfortunately, saponification of the methyl ester 18 proved problematic on this system as cleavage of the Boc group was observed under the basic conditions of both LiOH/MeOH/THF/H$_2$O or LiI/pyridine. Decomposition of the methyl ester was also observed when TMSOK in methylene chloride or (Bu$_3$Sn)$_2$O in toluene at either ambient temperature or reflux were employed as the saponification agents (data not shown).

Persuaded by these results that the current route required revision, we began a second generation approach to our core scaffold (Scheme 5). This approach relied on a different protecting group strategy, substituting the methyl ester for a benzyl ester which, in the case of another failed attempt at aminolysis, would undergo hydrogenolysis under mild conditions to deliver the corresponding Boc-protected acid 22. Synthesis began with the known mono benzyl ester acid (Li et al., *J. Am. Chem. Soc.*, 1995, 117, 2123-2127.20 which was transformed into the benzyl protected α-bromoketone by conversion to its acid chloride followed by diazomethane homologation and concomitant quench with concentrated HBr. Cyclization of this intermediate afforded the Boc-protected 2-AI 21 in 66% yield. All attempts at direct aminolysis of benzyl ester 21 resulted in sluggish reactions that were plagued by the formation of multiple side products.

Scheme 5. 2nd Generation Synthesis of RA Scaffold:

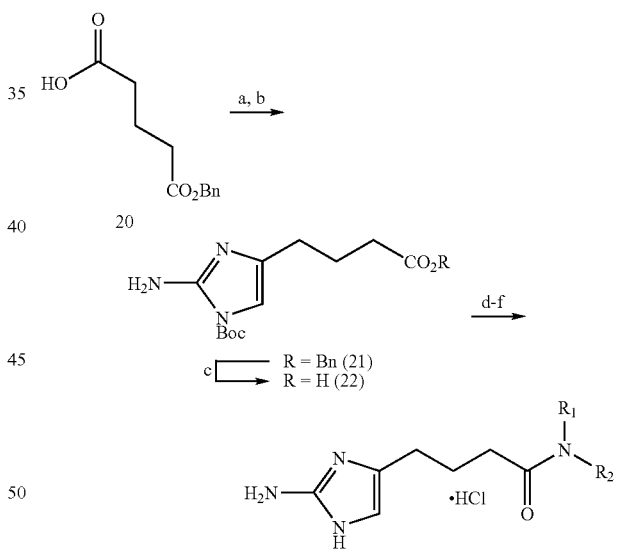

Reaction conditions: (a) i. (COCl)$_2$, DMF (cat.), CH$_2$Cl$_2$ ii. CH$_2$N$_2$, Et$_2$O/CH$_2$Cl$_2$, 0° C. iii. conc. HBr, 88% (b) Boc-guanidine, DMF, 66% (c) H$_2$ (1 atm), 10% Pd/C, THF, 98% (d) EDC, HOBt, NR$_1$R$_2$, DMF (e) TFA, CH$_2$Cl$_2$ (f) 2M HCl in Et$_2$O Given the failure of the direct aminolysis conversion, the two-step approach to the RA scaffold was investigated. Deprotection proceeded as planned and was accomplished by subjecting 21 to a hydrogen atmosphere at balloon pressure to cleanly afford pure Boc-protected acid 22 in near quantitative yield (98%). With the acid now in hand and available on a multi-gram scale, attempts to install the key amide bond were assessed. A number of activating agents were scanned including DCC, EDC, HCTU, CDI, and cyanuric chloride to affect the transformation. Of those listed only EDC and HCTU were able to give consistent and tangible results. EDC was chosen over HCTU due to ease of purification in separating side products during column chromatography. It was during this optimization that the limitation of the synthetic route was identified to be the reactivity of the Boc group. A significant quantity of a Boc-protected starting amine was isolated and characterized, signifying the lability of the Boc-group due to Boc-transfer under the reaction conditions regardless of which activating agent was used.

With two routes in hand to generate the RA scaffold, we assembled the focused library outlined in Table 2. EDC/HOBt couplings of acid 22 were used to generate most of the linear alkyl chain analogues (28-34%) while aminolysis of the methyl ester intermediate 18 furnished the remaining compounds (11-55%) in the library (Table 2). The final step of the synthetic approach required removal of the Boc group, which proceeded at room temperature in TFA/DCM. The resulting trinflouroacetate salts of each target were then traded out for their HCl counterparts before characterization and assessment of their biological activity.

TABLE 2

Completion of the reverse amide library

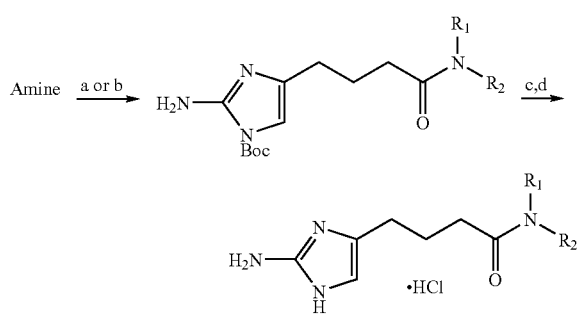

| Amine | Conditions | Coupled Product | Target |
| --- | --- | --- | --- |
| isobutylamine | a | 23 | 8 |
| hexylamine | b | 24 | 9 |
| octylamine | b | 25 | 10 |
| decylamine | a | 26 | 11 |
| dododecylamine | b | 27 | 12 |
| cyclopentylamine | a | 28 | 13 |
| morpholine | a | 29 | 14 |
| aniline | a | 30 | 15 |
| 2-aminopyrimidine | a | 31 | 16 |

Reaction conditions: (a) AlMe$_3$, 18, DCE, 0° C. to 60° C. (b) 22, EDC, HOBt, DMF (c) TFA, CH$_2$Cl$_2$ (d) 2M HCl in Et$_2$O Biological Evaluation of RA Library. Nosocomial infections are driven by a persistent bacterial colonization of hospital facilities, wherein the bacteria are extremely resistant to eradication because they exist in a biofilm state. *P. aeruginosa* is an opportunistic γ-proteobacterium that is a serious threat to immunocompromised patients and is frequently isolated from patients found in intensive care units suffering from severe burns or other traumas. It is the second most common pathogen in hospital-acquired pneumonia behind *Staphylococcus aureus*. Driscoll et al., *Drugs*, 2007, 67, 351-368. For Cystic Fibrosis patients, the onset of colonization by this bacterium is of great concern. Morbidity rates of patients who suffer from the disease are directly correlated to the virulence of *P. aeruginosa* biofilms. J. W. Costerton, *Trends in Microbiology*, 2001, 9, 50-52. T. F. C. Mah and G. A. O'Toole, *Trends Micro.*, 2001, 9, 34-39. The speed and prevalence with which multidrug resistant (MDR) strains are appearing puts pressure on the medical community to find ways to combat the aggressive nature of this bacterium. M. E. Falagas and E. A. Karveli, *Clin. Microbiol. Infec.*, 2007, 13, 117-119.

Figure 12:
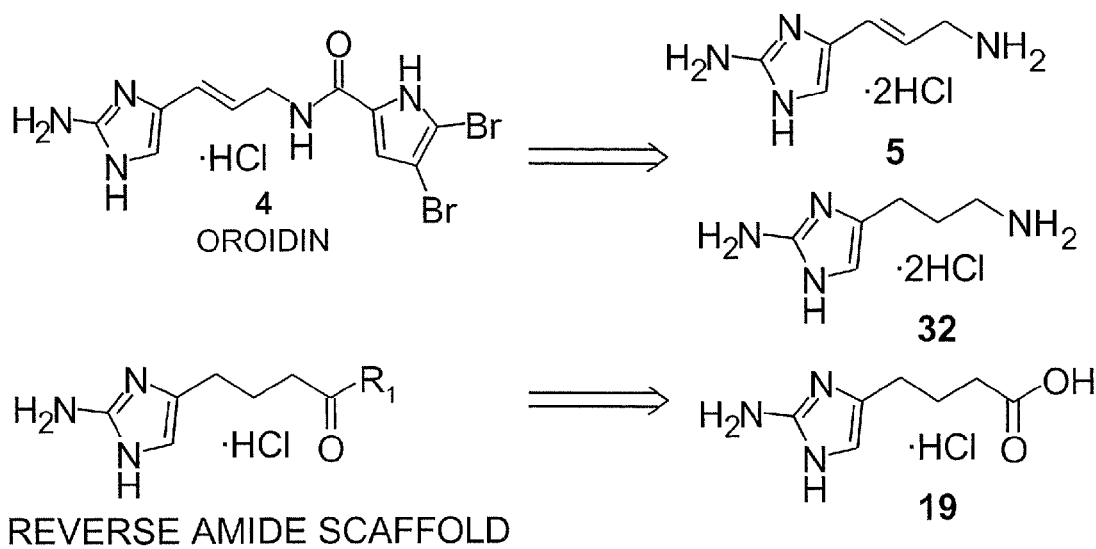
FIG. 12. Inhibition data at 500 µM for the RA library. All values are averages of at least three experiments.
Figure 12:
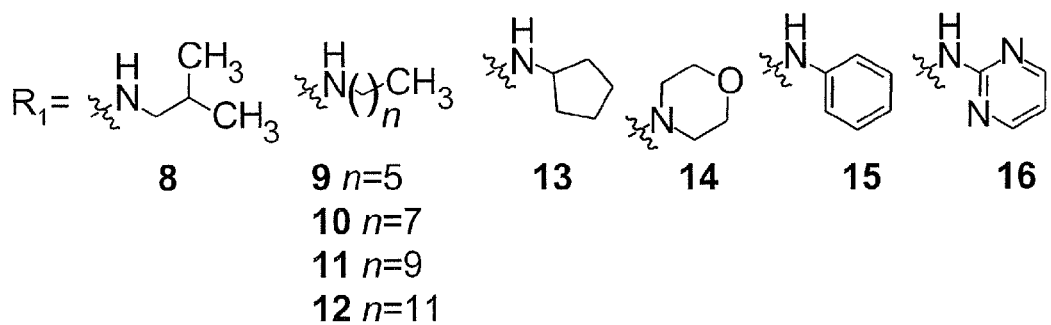

Members of the reverse amide library along with oroidin Olofson et al., *J. Org. Chem.*, 1998, 63, 1248-1253; Oroidin was synthesized as reported and matched characterization data. were initially screened at 500 μM in a 96-well format using a crystal violet reporter assay to assess each compound's ability to inhibit the formation of PAO1 or PA14 biofilms (FIG. 12). G. A. O'Toole and R. Kolter, *Mol. Microbiol.*, 1998, 28, 449-461. Compounds 5, 19, and 32 were used as controls in the assays and all showed only marginal inhibition. There was a remarkable range of activities among the RA compounds analyzed in the inhibition assay. Similar activities were observed between PAO1 and PA14, although most compounds were slightly more potent against PA14. This trend is opposite to our previously reported bromoageliferin analogues. Huigens et al., *J. Am. Chem. Soc.*, 2007, 129, 6966-6967. These screens also suggested that the aliphatic chain derivatives (9-12) and oroidin 4 were very potent inhibitors of *P. aeruginosa* biofilms.

Figure 13:
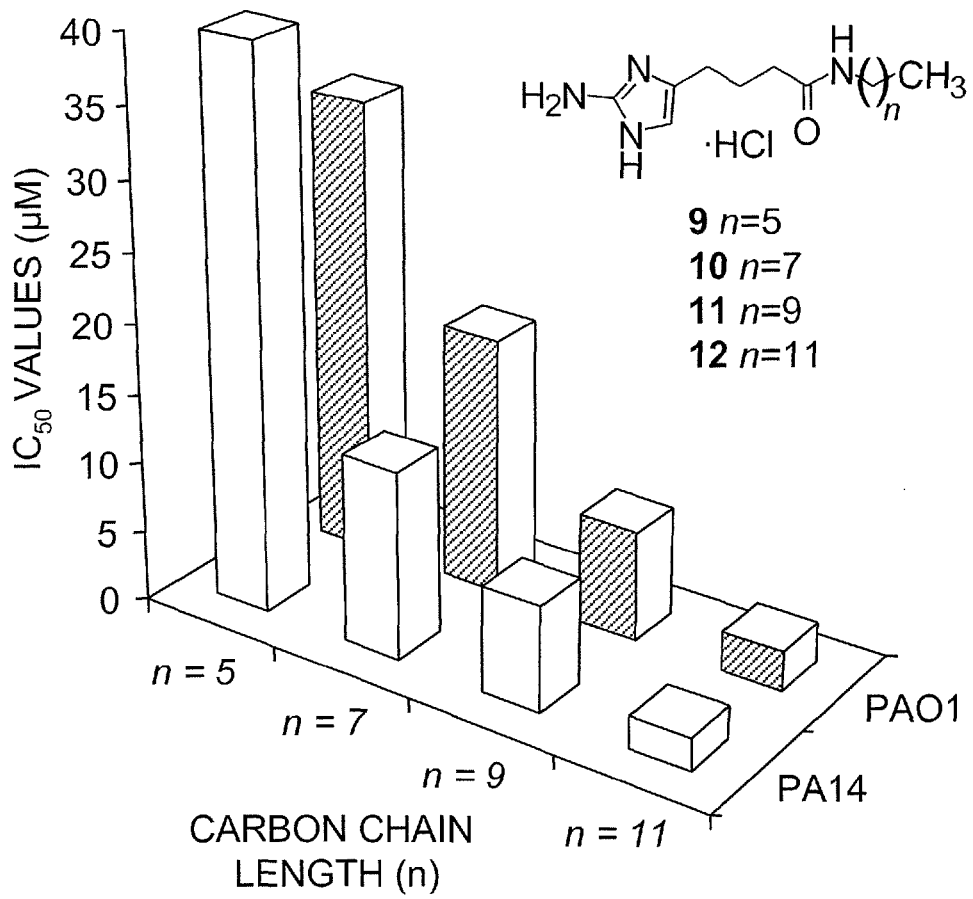
FIG. 13. Structure activity relationship of aliphatic chain RA analogues.

Subsequently, the aliphatic derivatives (9-12) and oroidin 4 were selected for IC$_{50}$ value determination against PAO1 and PA14 (Table 3). The generation of dose-response curves for these compounds revealed a correlation between the length of the carbon chain and the potency of the compound (supporting information). This trend is apparent when the IC$_{50}$ values are plotted as a function of chain length in both PAO1 and PA14 (FIG. 13). Increasing the chain length from six to twelve carbons effectively increased the inhibition activity over a full order of magnitude in both strains. All linear carbon chain analogues were significantly more potent than oroidin (PAO1 IC$_{50}$=190 μM, PA14 IC$_{50}$=166 μM). The most active RA analogue identified was 12 (PAO1 IC$_{50}$=2.84 μM, PA14 IC$_{50}$=2.26 μM), effectively demonstrating that changes to certain portions of the natural product have the ability to dramatically increase biological activity.

TABLE 3

| PAO1 and PA14 IC$_{50}$ values. | | |
| --- | --- | --- |
| Compound | PAO1 IC$_{50}$ (μM) | PA14 IC$_{50}$ (μM) |
| oroidin (4) | 190 ± 9 | 166 ± 23 |
| 9 (n = 5) | 32.7 ± 6.5 | 39.9 ± 13.0 |
| 10 (n = 7) | 18.4 ± 2.3 | 13.3 ± 1.8 |
| 11 (n = 9) | 7.79 ± 1.52 | 7.48 ± 1.60 |
| 12 (n = 11) | 2.84 ± 0.93 | 2.26 ± 0.83 |

To validate that our compounds were true inhibitors of biofilm formation and not acting as bactericidal agents, growth curves were performed at the determined IC$_{50}$ values for PAO1 and PA14 with the dodecyl-based analogue 12 and oroidin 4. Bacterial cell densities for both strains remained unchanged when grown in the presence or absence of either the natural product 4 or 12 throughout a 24-hour time period (supporting information).

Figure 14:
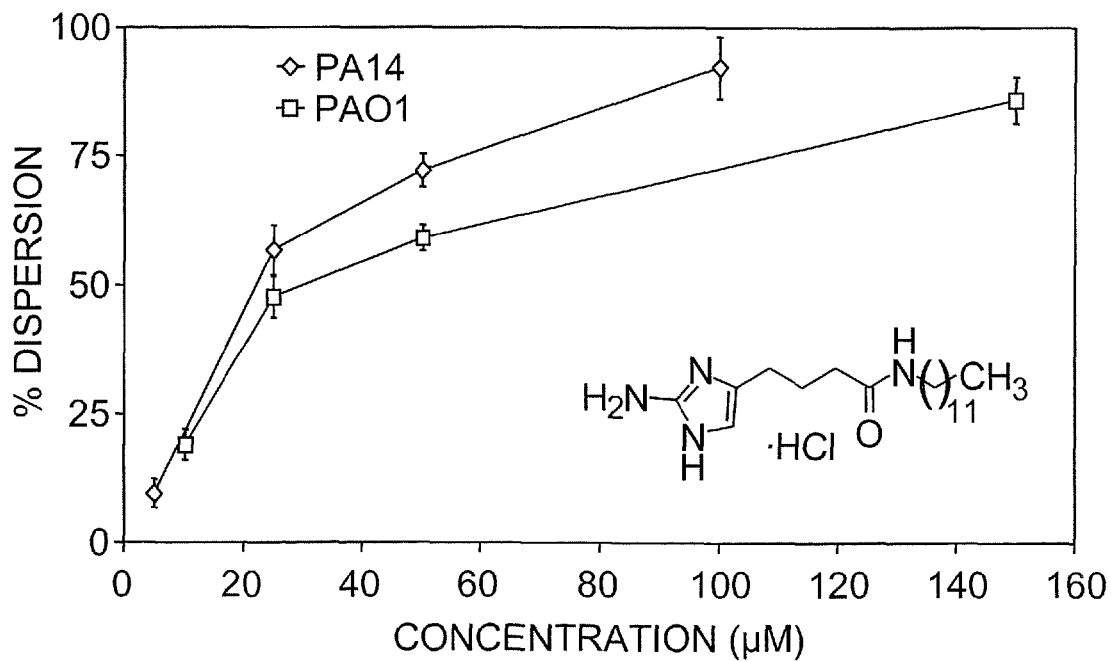
FIG. 14. Dispersion of established *P. aeruginosa* biofilms with 12.

While the focus has predominantly been on designing small molecules that inhibit the formation of biofilms, the more significant challenge is the development of a small molecule that will disperse established biofilms. Treatment of chronic infections is commonly hindered by the presence of established biofilms that impart increased resistance to conventional antibiotics. Costerton et al., *Science*, 1999, 284, 1318-1322. Small molecules able to disperse established biofilms are, therefore, of great interest to the medical community. To test for the ability to disperse established biofilms, PAO1 and PA14 were allowed to form biofilms for 24 hours in the absence of compound. After this time the media was discarded. The wells were washed and fresh media was added containing varying concentrations of 12 and then incubated at 37° C. for 24 hours. RA analogue 12 displayed significant anti-biofilm activity, dispersing established PAO1 and PA14 biofilms with $EC_{50}$ values of 32.8±4.7 µM and 21.3±3.9 µM respectively (FIG. 14).

In conclusion, we have identified several reverse amide (RA) analogues that possess potent anti-biofilm properties. These compounds are based on a reverse amide scaffold which switches the directionality of the amide bond frequently found in many members of the oroidin class of marine alkaloids. The synthetic path taken to access these derivatives allows for rapid access and simplified purification of all library analogues. Clearly, the most potent derivatives were those that contained linear carbon chains of various lengths from the amide nitrogen. The most active of these compounds, 12, has also been shown to disperse established *P. aeruginosa* biofilms at low micromolar concentrations, making it a highly noteworthy addition to the limited number of small molecules known to possess such characteristics. L. M. Junker and J. Clardy, *Antimicrob. Agents Ch.*, 2007, 51, 3582-3590. Banin et al., *Appl. Environ. Microb.*, 2006, 72, 2064-2069. Boles et al., *Mol. Microbiol.*, 2005, 57, 1210-1223.

Experimental. Stock solutions (100, 10, 1 mM) of all compounds assayed for biological activity were prepared in DMSO and stored at room temperature. The amount of DMSO used in both inhibition and dispersion screens did not exceed 1% (by volume). *P. aeruginosa* strains PAO1 and PA14 were graciously supplied by the Wozniak group at Wake Forest University School of Medicine.

General Static Inhibition Assay Protocol for *Pseudomonas aeruginosa*. An overnight culture of the wild type strain was subcultured at an $OD_{600}$ of 0.10 into LBNS along with a predetermined concentration of the small molecule to be tested for biofilm inhibition. Samples were then aliquoted (100 µL) into the wells of a 96-well PVC microtiter plate. The microtiter dishes were covered and sealed before incubation under stationary conditions at 37° C. for 24 hours. After that time, the medium was discarded and the plates thoroughly washed with water. The wells were then inoculated with a 0.1% aqueous solution of crystal violet (100 µL) and allowed to stand at ambient temperature for 30 minutes. Following another thorough washing with water the remaining stain was solubilized with 200 µL of 95% ethanol. Biofilm inhibition was quantitated by measuring the $OD_{540}$ for each well by transferring 125 µL of the ethanol solution into a fresh polystyrene microtiter dish for analysis.

General Static Dispersion Assay Protocols for *Pseudomonas aeruginosa*. An overnight culture of the wild type strain was subcultured at an $OD_{600}$ of 0.50 into LBNS and then aliquoted (100 µL) into the wells of a 96-well PVC microtiter plate. The microtiter dishes were covered and sealed before incubation under stationary conditions at room temperature to allow formation of the biofilms. After 24 hours the medium was discarded and the plates thoroughly washed with water. Fresh medium containing the appropriate concentration of compound was then added to the wells. The plates were again sealed and this time incubated under stationary conditions at 37° C. After 24 hours, the media was discarded from the wells and the plates washed thoroughly with water. The wells were inoculated with a 0.1% aqueous solution of crystal violet (100 µL) and allowed to stand at ambient temperature for 30 minutes. Following another thorough washing with water the remaining stain was solubilized with 200 µL of 95% ethanol. Biofilm dispersion was quantitated by measuring the $OD_{540}$ for each well by transferring 125 µL of the ethanol solution into a fresh polystyrene microtiter dish for analysis.

Chemistry. All reagents including anhydrous solvents used for the chemical synthesis of the library were purchased from commercially available sources and used without further purification unless otherwise noted. All reactions were run under either a nitrogen or argon atmosphere. Flash silica gel chromatography was performed with 60 Å mesh standard grade silica gel from Sorbtech. $^1$H and $^{13}$C NMR spectra were obtained using Varian 300 MHz or 400 MHz spectrometers. NMR solvents were purchased from Cambridge Isotope Labs and used as is. Chemical shifts are given in parts per million relative to DMSO-$d_6$ (δ 2.50) and $CDCl_3$ (δ 7.27) for proton spectra and relative to DMSO-$d_6$ (δ 39.51) and $CDCl_3$ (δ 77.21) for carbon spectra with an internal TMS standard. High-resolution mass spectra were obtained at the North Carolina State Mass Spectrometry Laboratory for Biotechnology. ESI experiments were carried out on Agilent LC-TOF mass spectrometer.

6-bromo-5-oxo-hexanoic acid methyl ester. Methyl glutaryl chloride (2.5 mL, 18.23 mmol) was dissolved into anhydrous dichloromethane (10 mL) and added drop-wise to a 0° C. solution of $CH_2N_2$ (55.0 mmol generated from Diazald® diazomethane precursor/KOH) in diethyl ether (150 mL). This solution was stirred at 0° C. for 1.5 h at which time the reaction was quenched via the drop-wise addition of 48% HBr (7.5 mL). The reaction mixture was diluted with dichloromethane (25 mL) and immediately washed with sat. $NaHCO_3$ (3×25 mL) and brine (2×25 mL) before being dried ($MgSO_4$), filtered and concentrated. The crude oil was purified via flash column chromatography (10-30% EtOAc/Hexanes) to obtain the title compound (3.76 g, 93%) as a colorless oil. $^1$H NMR (400 MHz, $CDCl_3$) δ 3.91 (s, 2H), 3.68 (s, 3H), 2.76 (t, 2H, J=7.2 Hz), 2.38 (t, 2H, J=7.2 Hz), 1.95 (quint, 2H, J=7.2 Hz); $^{13}$C NMR (75 MHz, $CDCl_3$) δ 201.36, 173.41, 51.67, 38.74, 34.16, 32.87, 19.13; HRMS (ESI) calcd for $C_7H_{12}O_3Br$ $(MH)^+$ 222.9964, found 222.9964.

6-chloro-5-oxo-hexanoic acid methyl ester. Using the same general procedure as used above but instead quenching with conc. HCl afforded the chloro derivative (2.93 g, 90%) as a colorless oil. $^1$H NMR (400 MHz, $CDCl_3$) δ 4.13 (s, 2H), 3.67 (s, 3H), 2.69 (t, 2H, J=7.2 Hz), 2.38 (t, 2H, J=7.2 Hz), 1.94 (quint., 2H, J=7.2 Hz); $^{13}$C NMR (100 MHz, $CDCl_3$) δ 201.85, 173.33, 51.57, 48.22, 38.47, 32.66, 18.61; HRMS (ESI) calcd for $C_7H_{12}O_3Cl$ $(MH)^+$ 179.0469, found 179.0476.

6-bromo-5-oxo-hexanoic acid benzyl ester. Monobezylesterbutanoic acid 20 (3.00 g, 13.6 mmol) was dissolved in anhydrous dichloromethane (70 mL) at 0° C. and a catalytic amount of DMF was added. To this solution was added oxalyl chloride (3.60 mL, 41.3 mmol) drop-wise and the solution was then warmed to room temperature. After 1 h, the solvent and excess oxalyl chloride were removed under reduced pressure. The resulting solid was dissolved into anhydrous dichloromethane (10 mL) and added drop-wise to a 0° C. solution of $CH_2N_2$ (42.0 mmol generated from Diazald® diazomethane precursor (Sigma-Aldrich, St. Louis, Mo.)/KOH) in diethyl ether (120 mL). This solution was stirred at 0° C. for 1.5 h at which time the reaction was quenched via the drop-wise addition of 48% HBr (4.7 mL). The reaction mixture was diluted with dichloromethane (25 mL) and immediately washed with sat. $NaHCO_3$ (3×25 mL) and brine (2×25 mL) before being dried ($MgSO_4$), filtered and concentrated. The crude oil was purified by flash column chromatography (0-30% EtOAc/Hexanes) to obtain the title compound (3.57 g, 88%) as a colorless oil. $^1$H NMR (400 MHz, $CDCl_3$) δ 7.35 (m, 5H), 5.12 (s, 2H), 3.85 (s, 2H), 2.73 (t, 2H, J=6.8 Hz), 2.42 (t, 2H, J=6.8 Hz), 1.96 (quint, 2H, J=6.8 Hz); $^{13}$C NMR (75

MHz, CDCl$_3$) δ 201.43, 172.88, 136.15, 128.79, 128.48, 128.45, 66.52, 38.74, 34.07, 33.20, 19.23; HRMS (ESI) calcd for C$_{13}$H$_{16}$O$_3$Br (MH)[30] 299.0277, found 299.0279.

2-amino-4-(3-methoxycarbonyl-propyl)-imidazole-1-carboxylic acid tert-butyl ester (18). 6-bromo-5-oxo-hexanoic acid methyl ester (2.30 g, 10.3 mmol), Boc-guanidine (4.92 g, 30.9 mmol),[32] and NaI (3.07 g, 20.6 mmol) were dissolved in DMF (30 mL) and allowed to stir at room temperature. After 24 h the DMF was removed under reduced pressure and the residue was taken up in ethyl acetate (100 mL) and washed with water (3×50 mL) and brine (50 mL) before being dried (Na$_2$SO$_4$), filtered and evaporated to dryness. The resulting oil was purified by flash column chromatography (50-100% EtOAc/Hexanes) to obtain a yellow oil. Trituration of the viscous oil with cold hexanes (20 mL) produced a precipitate, which upon filtration yielded 18 (1.89 g, 65%) as a pale yellow solid. $^1$H NMR (400 MHz, CDCl$_3$) δ 6.53 (s, 1H), 5.6 (br s, 2H), 2.41 (t, 2H, J=7.2 Hz), 2.37 (t, 2H, J=7.2 Hz), 1.93 (quint., 2H, J=7.2 Hz), 1.58 (s, 9H); $^{13}$C NMR (75 MHz, CDCl$_3$) δ 174.09, 150.11, 149.61, 138.39, 107.15, 84.81, 51.56, 33.65, 28.18, 27.68, 23.82; HRMS (ESI) calcd for C$_{13}$H$_{22}$N$_3$O$_4$ (MH)$^+$284.1604, found 284.1606.

4-(2-amino-1H-imidazol-4-yl) butyric acid hydrochloride (19). To 2-amino-4-(3-methoxycarbonyl-propyl)-imidazole-1-carboxylic acid tert-butyl ester 18 (50 mg, 0.176 mmol) was added methanol (0.60 mL), tetrahydrofuran (0.20 mL), and water (0.20 mL). Lithium hydroxide (9 mg, 0.352 mmol) was then added and the reaction was stirred at room temperature for 30 min. The pH of the solution was carefully adjusted to pH=5 with a 1N aqueous solution of HCl before being evaporated to dryness. The crude product was purified via a silica gel plug (100% MeOH sat. NH$_3$) to deliver the product as its corresponding free base. The hydrochloride salt was obtained through addition of a single drop of concentrated HCl to a methanolic solution (2 mL) of the free base. Rotary evaporation of this solution afforded 19 (34 mg, 94%) as a white solid. $^1$H NMR (300 MHz, DMSO-d$_6$) δ 12.25 (s, 1H), 12.13 (br s, 1H), 11.77 (s, 1H), 7.33 (s, 2H), 6.54 (s, 1H) 2.43 (t, 2H, J=7.2 Hz), 2.21 (t, 2H, J=7.2 Hz), 1.73 (m, 2H); $^{13}$C NMR (100 MHz, DMSO-d$_6$) δ 174.04, 146.92, 126.01, 108.62, 32.81, 23.47, 23.05; HRMS (ESI) calcd for C$_7$H$_{12}$N$_3$O$_2$ (MH)$^+$ 170.0924, found 170.0927.

2-amino-4-(3-benzyloxycarbonyl-propyl)-imidazole-1-carboxylic acid tert-butyl ester (21). 6-bromo-5-oxo-hexanoic acid benzyl ester (3.42 g, 11.99 mmol) and Boc-guanidine (5.73 g, 35.97 mmol) were dissolved in DMF (35 mL) and allowed to stir at room temperature. After 48 h the DMF was removed under reduced pressure and the residue was taken up in ethyl acetate (100 mL) and washed with water (3×50 mL) and brine (50 mL) before being dried (Na$_2$SO$_4$), filtered and evaporated to dryness. The resulting oil was purified by flash column chromatography (30-100% EtOAc/Hexanes) to obtain the title compound (2.79 g, 66%) as a colorless oil which solidified upon prolonged standing. $^1$H NMR (400 MHz, CDCl$_3$) δ 7.35 (m, 5H), 6.51 (s, 1H), 5.91 (s, 2H), 5.12 (s, 2H), 2.41 (m, 4H), 1.94 (quint., 2H, J=7.2 Hz), 1.57 (s, 9H); $^{13}$C NMR (75 MHz, CDCl$_3$) δ 173.45, 150.31, 149.59, 138.27, 136.36, 128.67, 128.29, 128.27, 107.05, 84.73, 66.23, 33.82, 28.16, 27.62, 23.79; HRMS (ESI) calcd for C$_{19}$H$_{26}$N$_3$O$_4$ (MH)$^+$360.1917, found 360.1919.

2-amino-4-(3-carboxy-propyl)-imidazole-1-carboxylic acid tert-butyl ester (22). To a solution of anhydrous THF (2 mL) and 10% Pd/C (12 mg) was charged 2-amino-4-(3-benzyloxycarbonyl-propyl)-imidazole-1-carboxylic acid tert-butyl ester 21 (101 mg, 0.281 mmol). Air was removed from the system and the reaction was back flushed with hydrogen. This process was repeated three times before setting the reaction under a hydrogen balloon at atmospheric pressure and temperature for 1 h. After that time the reaction was filtered through a Celite® diatomite pad (World Minerals Inc., Santa Barbara, Calif.) and the filter cake was washed with THF (8 mL). The filtrate was concentrated under reduced pressure to afford the title compound 21 (75 mg, 98%) as a white solid. $^1$H NMR (400 MHz, DMSO-d$_6$) δ 6.52 (s, 1H), 6.42 (br s, 2H), 2.52 (t, 2H, J=5.4 Hz), 2.18 (t, 2H, J=5.4 Hz), 1.71 (m, 2H), 1.53 (s, 9H); $^{13}$C NMR (100 MHz, DMSO-d$_6$) δ 175.00, 149.99, 148.95, 138.28, 105.86, 84.09, 39.24, 38.85, 33.70, 27.52, 27.08, 23.52; HRMS (ESI) calcd for C$_{12}$H$_{20}$N$_3$O$_4$ (MH)$^+$270.1448, found 270.1452.

General aminolysis procedure: To a stirring 0° C. solution of amine (0.704 mmol) in anhydrous 1,2-dichloroethane (1 mL) was added drop-wise a 2M solution of AlMe$_3$ in PhCH$_3$ (0.351 mL, 0.704 mmol). The solution was stirred for 10 min before the addition of 2-amino-4-(3-methoxycarbonyl-propyl)-imidazole-1-carboxylic acid tert-butyl ester 18 (100 mg, 0.352 mmol) in several portions. Once dissolution was complete, the reaction was warmed to 60° C. and stirred until completion as evident by TLC analysis. The reaction was then cooled back down to 0° C. before being diluted with dichloromethane (5 mL) and quenched with water (1 mL). The resulting viscous solution was warmed to ambient temperature and Celite® diatomite was added. After stirring for 5 min, the mixture was filtered and the filtrate washed with brine (2×3 mL), dried (Na$_2$SO$_4$), and evaporated to dryness. The crude product was purified via flash column chromatography (2-10% MeOH/CH$_2$Cl$_2$) to afford pure product.

2-amino-4-(3-isobutylcarbamoyl-propyl)-imidazole-1-carboxylic acid tert-butyl ester (23) White solid (46 mg, 40%). $^1$H NMR (400 MHz, DMSO-d$_6$) δ 7.75 (m, 1H), 6.51 (s, 1H), 6.37 (br s, 2H), 2.85 (t, 2H, J=6.4 Hz), 2.22 (t, 2H, J=6.8 Hz), 2.07 (t, 2H, J=7.2 Hz), 1.61-1.73 (m, 3H), 1.53 (s, 9H), 0.81 (d, 6H, J=6.4 Hz); $^{13}$C NMR (100 MHz, DMSO-d$_6$) δ 171.82, 149.92, 148.95, 138.39, 105.84, 84.04, 45.94, 34.88, 28.09, 27.52, 27.23, 24.10, 20.14; HRMS (EST) calcd for C$_{16}$H$_{29}$N$_4$O$_3$ (MH)$^-$325.2234, found 325.2238.

2-amino-4-(3-decylcarbamoyl-propyl)-imidazole-1-carboxylic acid tert-butyl ester (26). Tan solid (24 mg, 16%). $^1$H NMR (400 MHz, DMSO-d$_6$) δ 7.74 (m, 1H), 6.52 (s, 1H), 6.49 (br s, 2H), 3.00 (q, 2H, J=6.8 Hz), 2.22 (t, 2H, J=6.8 Hz), 2.04 (t, 2H, J=6.8 Hz), 1.71 (quint., 2H, J=6.8 Hz), 1.53 (s, 9H), 1.36 (m, 2H), 1.23 (s, 14H), 0.85 (t, 3H, J=6.8 Hz); $^{13}$C NMR (100 MHz, DMSO-d$_6$) δ 171.64, 149.82, 148.86, 137.90, 105.90, 84.16, 38.33, 34.88, 31.31, 29.16, 29.03, 28.97, 28.75, 28.73, 28.02, 27.51, 27.05, 26.40, 24.04, 22.12, 13.97; HRMS (ESI) calcd for C$_{22}$H$_{41}$N$_4$O$_3$ (MH)$^+$409.3173, found 409.3175.

2-amino-4-(3-cyclopentylcarbamoyl-propyl)-imidazole-1-carboxylic acid tert-butyl ester (28). White solid (54 mg, 45%). $^1$H NMR (400 MHz, DMSO-d$_6$) δ 7.72 (d, 1H, J=6.4 Hz), 6.5 (s, 1H), 6.38 (s, 2H), 3.97 (m, 1H), 2.21 (t, 2H, J=7.2 Hz), 2.02 (t, 2H, J=7.2 Hz), 1.73 (m, 4H), 1.61 (m, 2H), 1.53 (s, 9H), 1.47 (m, 2H), 1.32 (m, 2H); $^{13}$C NMR (75 MHz, DMSO-d$_6$) δ 171.27, 149.92, 148.96, 138.37, 105.88, 84.02, 50.04, 34.79, 32.32, 28.05, 27.53, 27.17, 24.00, 23.43; HRMS (ESI) calcd for C$_{17}$H$_{29}$N$_4$O$_3$ (MH)$^+$337.2234, found 337.2235.

2-amino-4-(4-morpholin-4-yl-4-oxo-butyl)-imidazole-1-carboxylic acid tert-butyl ester (29). Tan solid (33 mg, 27%). $^1$H NMR (400 MHz, DMSO-d$_6$) δ 6.52 (s, 1H), 6.39 (s, 2H), 3.52 (m, 4H), 3.41 (m, 4H), 2.28 (m, 4H), 1.42 (quint., 2H, J=7.2 Hz) 1.53 (s, 9H); $^{13}$C NMR (75 MHz, DMSO-d$_6$) δ 171.43, 150.56, 149.64, 139.17, 106.58, 84.78, 66.85, 46.14, 32.23, 28.23, 27.89, 24.19; HRMS (ESI) calcd for C$_{16}$H$_{27}$N$_4$O$_4$ (MH)$^+$339.2026. found 339.2027.

2-amino-4-(3-phenylcarbamoyl-propyl)-imidazole-1-carboxylic acid tert-butyl ester (30). White solid (66 mg, 55%). $^1$H NMR (300 MHz, DMSO-$d_6$) δ 9.88 (s, 1H), 7.59 (d, 2H, J=8.1 Hz), 7.27 (t, 2H, J=7.5 Hz), 7.00 (t, 1H, J=7.2 Hz), 6.55 (s, 1H), 6.44 (br s, 2H), 2.97 (m, 4H), 1.82 (m, 2H), 1.53 (s, 9H); $^{13}$C NMR (75 MHz, DMSO-$d_6$) δ 170.95, 149.71, 148.86, 139.25, 138.16, 128.47, 122.78, 118.98, 105.92, 84.00, 38.42, 35.71, 27.44, 27.01, 23.72; HRMS (ESI) calcd for $C_{18}H_{25}N_4O_3$ (MH)$^+$345.1921, found 345.1920.

2-amino-4-[3-(pyrimidin-2-ylcarbamoyl)-propyl]-imidazole-1-carboxylic acid tert-butyl ester (31). Tan solid (19 mg, 11%). $^1$H NMR (400 MHz, DMSO-$d_6$) δ 10.51 (s, 1H), 8.63 (d, 2H, J=4.8 Hz), 7.15 (t, 1H, J=4.8 Hz), 6.54 (s, 1H), 6.40 (s, 2H), 2.49 (t, 2H, J=7.2 Hz), 2.29 (t, 2H, J=7.2 Hz), 1.80 (quint., 2H, J=7.2 Hz), 1.53 (s, 9H); $^{13}$C NMR (75 MHz, DMSO-$d_6$) δ 171.34, 158.11, 157.63, 149.76, 148.85, 138.31, 116.37, 105.81, 83.98, 35.75, 27.44, 27.05, 23.37; HRMS (ESI) calcd for $C_{16}H_{23}N_6O_3$ (MH)$^+$347.1826, found 347.1827.

General EDC/HOBt procedure: 2-amino-4-(3-carboxypropyl)-imidazole-1-carboxylic acid tert-butyl ester 22 (100 mg, 0.371 mmol), 1-hydroxybenzotriazole (100 mg, 0.742 mmol) and N-(3-dimethylaminopropyl)-N'-ethylcarbodiimide hydrochloride (142 mg, 0.742 mmol) were dissolved in anhydrous DMF (3 mL). The appropriate amine coupling partner (1.48 mmol) was then added and the solution was stirred at ambient temperature until completion was evident by TLC analysis. The reaction was concentrated under reduced pressure and the residue partitioned between ethyl acetate (20 mL) and water (10 mL). The organic layer was successively washed with water (3×10 mL), a 10% aqueous solution of citric acid (2×10 mL), sat. NaHCO$_3$ (2×10 mL), and brine (10 mL) before being dried (Na$_2$SO$_4$) and evaporated to dryness. The crude product was purified via flash column chromatography (2-10% MeOH/CH$_2$Cl$_2$) to afford the target compound.

2-amino-4-(3-hexylcarbamoyl-propyl)-imidazole-1-carboxylic acid tert-butyl ester (24). Pale yellow solid (41 mg, 32%). $^1$H NMR (300 MHz, DMSO-$d_6$) δ 7.73 (m, 1H), 6.50 (s, 1H), 6.39 (s, 2H), 2.99 (q, 2H, J=6.3 Hz), 2.21 (t, 2H, J=7.5 Hz), 2.04 (t, 2H, J=7.2 Hz), 1.70 (m, 2H), 1.53 (s, 9H), 1.31 (m, 3H), 1.23 (br s, 7H), 0.85 (t, 3H, J=5.1 Hz); $^{13}$C NMR (75 MHz, DMSO-$d_6$) δ 171.68, 149.93, 148.95, 138.37, 105.81, 84.04, 38.35, 34.91, 31.01, 29.14, 27.52, 27.22, 26.10, 24.06, 22.09, 13.93; HRMS (ESI) calcd for $C_{18}H_{33}N_4O_3$ (MH)$^+$ 353.2547, found 353.2549.

2-amino-4-(3-octylcarbamoyl-propyl)-imidazole-1-carboxylic acid tert-butyl ester (25). White solid (48 mg, 34%). $^1$H NMR (300 MHz, DMSO-$d_6$) δ 7.73 (m, 1H), 6.50 (s, 1H), 6.38 (s, 2H), 2.99 (q, 2H, J=5.4 Hz), 2.21 (t, 2H, J=7.5 Hz), 2.04 (t, 2H, J=7.2 Hz), 1.73 (m, 2H), 1.53 (s, 9H), 1.36 (m, 4H), 1.23 (br s, 10H), 0.85 (t, 3H, J=5.1 Hz); $^{13}$C NMR (75 MHz, DMSO-$d_6$) δ 171.72, 149.95, 148.95, 138.43, 105.83, 84.06, 38.35, 34.92, 31.26, 29.16, 28.71, 27.53, 27.22, 26.43, 24.10, 22.12, 13.98; HRMS (ESI) calcd for $C_{20}H_{37}N_4O_3$ (MH)$^+$381.2860, found 381.2861.

2-amino-4-(3-dodecylcarbamoyl-propyl)-imidazole-1-carboxylic acid tert-butyl ester (27). White solid (44 mg, 28%). $^1$H NMR (400 MHz, DMSO-$d_6$) δ 7.73 (t, 1H, J=5.6 Hz), 6.50 (s, 1H), 6.38 (s, 2H), 3.00 (q, 2H, J=5.6 Hz), 2.21 (t, 2H, J=7.6 Hz), 2.04 (t, 2H, J=7.6 Hz), 1.71 (quint., 2H, J=7.6 Hz), 1.53 (s, 9H), 1.36 (m, 2H), 1.23 (s, 18H), 0.85 (t, 3H, J=6.0 Hz); $^{13}$C NMR (75 MHz, DMSO-$d_6$) δ 171.58, 149.77, 148.88, 138.42, 105.76, 83.98, 38.28, 34.90, 31.18, 29.06, 28.88, 28.58, 27.47, 27.18, 26.29, 24.04, 21.96, 13.81, 13.27; HRMS (ESI) calcd for $C_{24}H_{45}N_4O_3$ (MH)$^+$437.3486, found 437.3487.

4-(2-amino-1H-imidazol-4-yl)-N-isobutyl-butyramide hydrochloride (8). A solution of 2-amino-4-(3-isobutylcarbamoyl-propyl)-imidazole-1-carboxylic acid tert-butyl ester 23 (76 mg, 0.234 mmol) in anhydrous dichloromethane (1 mL) was cooled to 0° C. TFA (1 mL) was charged into the flask and the reaction stirred for 5 h. After that time the reaction was evaporated to dryness and toluene (2 mL) was added. Again the mixture was concentrated and the process repeated. The resulting TFA salt was dissolved in dichloromethane (1 mL) and 2M HCl in diethyl ether (0.50 mL) was added followed by cold diethyl ether (8 mL). The precipitate was collected by filtration and washed with diethyl ether (3 mL) to yield the target compound 8 (59 mg, 97%) as a tan solid. $^1$H NMR (300 MHz, DMSO-$d_6$) δ 12.14 (s, 1H), 11.70 (s, 1H), 7.89 (m, 1H), 7.34 (br s, 2H), 6.55 (s, 1H), 2.84 (t, 2H, J=6.6 Hz), 2.38 (t, 2H, J=7.5 Hz), 2.10 (t, 2H, J=7.5 Hz), 1.60-1.79 (m, 3H), 0.82 (d, 6H, J=6.3 Hz); $^{13}$C NMR (75 MHz, DMSO-$d_6$) δ 171.52, 146.78, 126.31, 108.68, 46.00, 34.41, 28.09, 23.94, 23.64, 20.18; HRMS (ESI) calcd for $C_{11}H_{21}N_4O$ (MH)$^+$225.1709, found 225.1711.

4-(2-amino-1H-imidazol-4-yl)-N-hexyl-butyramide hydrochloride (9). Using the same general procedure as used for the synthesis of 8, 2-amino-4-(3-hexylcarbamoyl-propyl)-imidazole-1-carboxylic acid tert-butyl ester 24 (90 mg, 0.255 mmol) gave 9 (70 mg, 96%) as a pale yellow foam. $^1$H NMR (300 MHz, DMSO-$d_6$) δ 11.96 (s, 1H), 11.54 (s, 1H), 7.81 (m, 1H), 7.29 (br s, 2H), 6.56 (s, 1H), 3.01 (m, 2H), 2.40 (t, 2H, J=7.8 Hz), 2.07 (t, 2H, J=7.2 Hz), 1.73 (m, 2H), 1.23-1.36 (m, 8H) 0.85 (m, 3H); $^{13}$C NMR (100 MHz, DMSO-$d_6$) δ 171.35, 146.72, 126.37, 108.71, 38.43, 34.41, 31.00, 29.12, 26.12, 23.87, 23.62, 22.09, 13.96; HRMS (ESI) calcd for $C_{13}H_{25}N_4O$ (MH)$^+$253.2022, found 253.2025.

4-(2-amino-1H-imidazol-4-yl)-N-octyl-butyramide hydrochloride (10). Using the same general procedure as used for the synthesis of 8, 2-amino-4-(3-octylcarbamoyl-propyl)-imidazole-1-carboxylic acid tert-butyl ester 25 (50 mg, 0.131 mmol) gave 10 (39 mg, 93%) as a white solid. $^1$H NMR (300 MHz, DMSO-$d_6$) δ 12.13 (s, 1H), 11.69 (s, 1H), 7.87 (m, 1H), 7.33 (br s, 2H), 6.55 (s, 1H), 2.99 (q, 2H, J=6.3 Hz), 2.38 (t, 2H, J=7.5 Hz), 2.07 (t, 2H, J=7.5 Hz), 1.73 (m, 2H), 1.35 (m, 2H), 1.23 (m, 10H), 0.85 (t, 3H, J=6.3 Hz); $^{13}$C NMR (75 MHz, DMSO-$d_6$) δ 171.30, 146.80, 126.32, 108.57, 38.40, 34.39, 31.15, 29.06, 28.62, 28.56, 26.37, 23.86, 23.57, 21.99, 13.85; HRMS (ESI) calcd for $C_{15}H_{29}N_4O$ (MH)$^+$281.2335, found 281.2339.

4-(2-amino-1H-imidazol-4-yl)-N-decyl-butyramide hydrochloride (11). Using the same general procedure as used for the synthesis of 8, 2-amino-4-(3-decylcarbamoyl-propyl)-imidazole-1-carboxylic acid tert-butyl ester 26 (32 mg, 0.078 mmol) gave 11 (27 mg, 99%) as a white solid. $^1$H NMR (400 MHz, DMSO-$d_6$) δ 12.07 (s, 1H), 11.64 (s, 1H), 7.85 (s, 1H), 7.32 (br s, 2H), 6.56 (s, 1H), 3.00 (q, 2H, J=6.4 Hz), 2.38 (t, 2H, J=7.2 Hz), 2.07 (t, 2H, J=7.2 Hz), 1.73 (quint., 2H, J=7.2 Hz), 1.36 (m, 2H), 1.23 (s, 14H), 0.85 (t, 3H, J=7.2 Hz); $^{13}$C NMR (100 MHz, DMSO-$d_6$) δ 171.33, 146.72, 126.36, 108.70, 38.42, 34.41, 31.32, 29.15, 29.04, 28.99, 28.77, 28.73, 26.45, 23.89, 23.62, 22.12, 13.99; HRMS (ESI) calcd for $C_{17}H_{33}N_4O$ (MH)$^+$ 309.2648, found 309.2647.

4-(2-amino-1H-imidazol-4-yl)-N-dodecyl-butyramide hydrochloride (12). Using the same general procedure as used for the synthesis of 8, 2-amino-4-(3-dodecylcarbamoyl-propyl)-imidazole-1-carboxylic acid tert-butyl ester 27 (20 mg, 0.046 mmol) gave 12 (16 mg, 94%) as a white solid. $^1$H NMR (400 MHz, DMSO-$d_6$) δ 12.03 (s, 1H), 11.60 (s, 1H), 7.83 (t, 1H, J=6.4 Hz), 7.31 (s, 2H), 6.56 (s, 1H), 3.00 (q, 2H, J=6.4 Hz), 2.38 (t, 2H, J=7.2 Hz), 2.07 (t, 2H, J=7.2 Hz), 1.73

(quint., 2H J=7.2 Hz), 1.36 (m, 2H), 1.23 (s, 18H), 0.85 (t, 2H, J=6.4 Hz); $^{13}$C NMR (75 MHz, DMSO-d$_6$) δ 171.20, 146.66, 126.34, 108.59, 38.34, 34.32, 34.32, 31.15, 29.02, 28.86, 28.6, 28.55, 26.31, 23.78, 23.52, 21.94, 13.79; HRMS (ESI) calcd for C$_{19}$H$_{37}$N$_4$O (MH)$^+$ 337.2961, found 337.2964.

4-(2-amino-1H-imidazol-4-yl)-N-cyclopentyl-butyramide hydrochloride (13). Using the same general procedure as used for the synthesis of 8, 2-amino-4-(3-cyclopentylcarbamoyl-propyl)-imidazole-1-carboxylic acid tert-butyl ester 28 (100 mg, 0.297 mmol) gave 13 (78 mg, 96%) as a pale yellow foam. $^1$H NMR (400 MHz, DMSO-d$_6$) δ 11.99 (s, 1H), 11.57 (s, 1H), 7.79 (d, 1H, J=7.2 Hz), 7.30 (s, 2H), 6.56 (s, 1H), 3.97 (m, 1H), 2.37 (t, 2H, J=7.2 Hz), 2.05 (t, 2H, J=7.2 Hz), 1.69-1.79 (m, 4H), 1.59 (m, 2H), 1.47 (m, 2H), 1.31 (m, 2H); $^{13}$C NMR (100 MHz, DMSO-d$_6$) δ 170.97, 146.74, 126.38, 108.72, 50.11, 34.36, 32.31, 23.81, 23.45, 23.62; HRMS (ESI) calcd for C$_{12}$H$_{21}$N$_4$O (MH)$^+$ 237.1709, found 237.1711.

4-(2-amino-1H-imidazol-4-yl)-1-morpholin-4-yl-butan-1-one hydrochloride (14). Using the same general procedure as used for the synthesis of 8, 2-amino-4-(4-morpholin-4-yl-4-oxo-butyl)-imidazole-1-carboxylic acid teri-butyl ester 29 (44 mg, 0.133 mmol) gave 14 (25 mg, 70%) as a tan solid. $^1$H NMR (400 MHz, DMSO-d$_6$) δ 12.1 (s, 1H), 11.64 (s, 1H), 7.33 (s, 2H), 6.58 (s, 1H), 3.54 (m, 4H), 3.42 (m, 4H), 2.43 (t, 2H, J=7.2 Hz), 2.33 (t, 2H, J=7.2 Hz), 1.75 (quint., 2H, J=7.2 Hz); $^{13}$C NMR (75 MHz, DMSO-d$_6$) δ 170.27, 146.72, 126.39, 108.61, 66.04, 45.28, 31.05, 23.56, 23.17; HRMS (ESI) calcd for C$_{11}$H$_{19}$N$_4$O$_2$ (MH)$^+$ 239.1502, found 239.1503.

4-(2-amino-1H-imidazol-4-yl)-N-phenyl-butyramide hydrochloride (15). Using the same general procedure as used for the synthesis of 8, 2-amino-4-(3-phenylcarbamoyl-propyl)-imidazole-1-carboxylic acid tert-butyl ester 30 (80 mg, 0.232 mmol) gave 15 (64 mg, 99%) as a tan solid. $^1$H NMR (400 MHz, DMSO-d$_6$) δ 12.03 (s, 1H), 11.60 (s, 1H), 9.98 (s, 1H), 7.59 (d, 2H, J=8.0 Hz), 7.33 (br s, 2H), 7.28 (t, 2H, J=8.0 Hz), 7.02 (t, 1H, J=7.6 Hz), 6.61 (s, 1H), 2.44 (m, 2H), 2.32 (t, 2H, J=6.8 Hz), 1.85 (m, 2H); $^{13}$C NMR (75 MHz, DMSO-d$_6$) δ 170.65, 146.77, 139.25, 137.24, 128.59, 126.40, 123.00, 119.13, 108.83, 35.33, 23.60, 23.51; HRMS (ESI) calcd for C$_{13}$H$_{17}$N$_4$O (MH)$^+$ 245.1396, found 245.1401.

4-(2-amino-1H-imidazol-4-yl)-N-pyrimidin-2-yl-butyramide hydrochloride (16). Using the same general procedure as used for the synthesis of 8, 2-amino-4-[3-(pyrimidin-2-ylcarbamoyl) -propyl]-imidazole-1-carboxylic acid tert-butyl ester 31 (50 mg, 0.144 mmol) gave 16 (41 mg, 99%) as a white solid. $^1$H NMR (400 MHz, DMSO-d$_6$) δ 12.06 (s, 1H), 11.64 (s, 1H), 10.59 (s, 1H), 8.64 (d, 2H, J=4.8 Hz), 7.34 (s, 2H), 7.17 (t, 1H, J=4.8 Hz), 6.60 (s, 1H), 2.51 (m, 2H), 2.46 (t, 2H, J=7.2 Hz), 1.83 (quint., 2H, J=7.2 Hz); $^{13}$C NMR (75 MHz, DMSO-d$_6$) δ 158.17, 157.54, 146.73, 129.02, 126.33, 116.5, 108.71, 35.35, 23.48, 23.09; HRMS (ESI) calcd for C$_{11}$H$_{15}$N$_6$O (MH)$^+$ 247.1301, found 247.1304.

EXAMPLE 5

Analysis of a library of oroidin derivatives. Two members of the oroidin family, bromoageliferin and oroidin, were documented to possess anti-biofouling properties by inhibiting biofilm development in the marine α-proteobacterium R. salexigens. A. Yamada et al., Bull. Chein. Soc. Jpn. 1997, 70, 3061. Herein we provide the results of a structure-activity relationship (SAR) analysis from the synthesis and biological evaluation of a 50 compound oroidin library in the context of anti-biofilm activity against the medically relevant gram-negative γ-proteobacterium P. aeruginosa.

Marine natural products provide a diverse array of chemical structures and are known to possess a plethora of biological activities. M. D. Lebar, et al., Nat. Prod. Rep. 2007, 24, 774. Most members of the oroidin alkaloid family have nitrogen dense architectures that contain a 2-aminoimidazole (2-AI) subunit. H. Hoffmann, T. Lindel, Synthesis-Stuttgart 2003, 1753. S. M. Weinreb, Nat. Prod. Rep. 2007, 24, 931. These compounds are typically found in sponges of the family Agelasidae and mainly serve as a chemical anti-feeding defense mechanism against predators. J. C. Braekman, et al., Biochem. Syst. Ecol. 1992, 20, 417. Oroidin is believed to be one of the main building blocks in the biosynthesis of other more complex family members including palau'amine and the stylissadines. A. Al Mourabit, P. Potier, Eur. J. Org. Chem. 2001, 237. M. Kock, et al., Angew. Chem., Int. Ed. 2007, 46, 6586. In addition to being documented to interfere with the biofouling process of R. salexigens, oroidin has also been observed to retard bacterial attachment and colonization in a limited number of studies. S. R. Kelly, et al., Aquat. Microb. Ecol. 2005, 40, 191. S. R. Kelly, et al., Aquat. Microb. Ecol. 2003, 31, 175.

A library of analogues was synthesized based upon the oroidin template. The structure-activity relationships (SAR) were then delineated within the context of anti-biofilm activity. Molecules based on oroidin would require a relatively short reaction sequence to access (2-6 steps) and could be rapidly assembled from core scaffolds and screened for their anti-biofilm properties.

Figure 15:
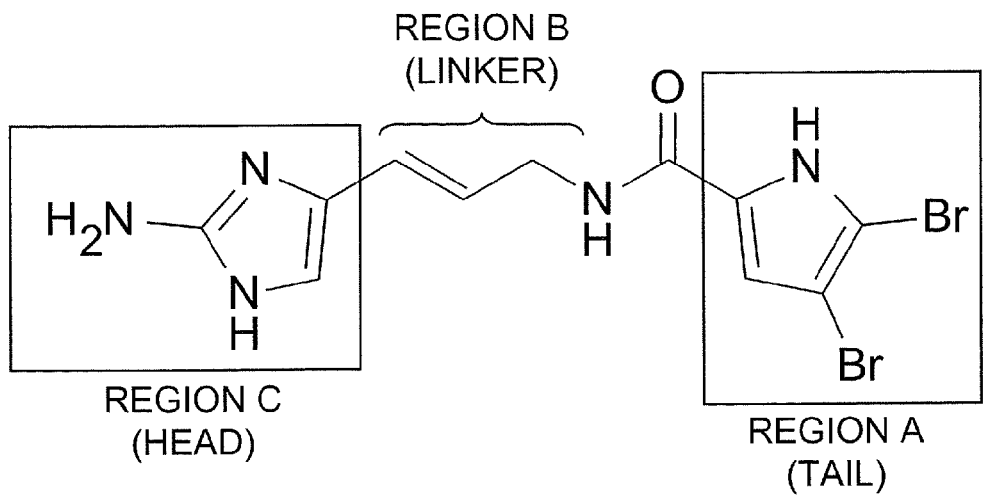
FIG. 15. Fragmentation of the oroidin template for SAR study.
Figure 16:
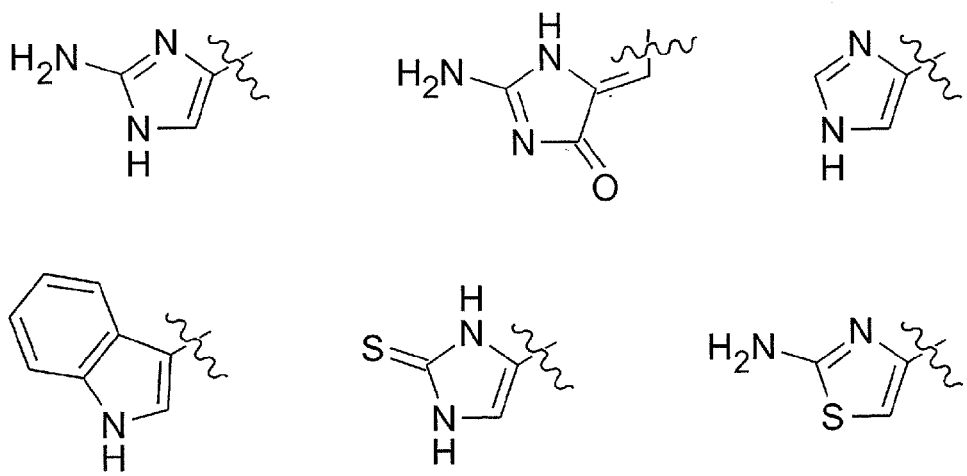
FIG. 16. Region C SAR design.

Using this natural product as our base, a focused library was constructed by systematically varying three regions within the oroidin template (FIG. 15) to delineate what structural features of the molecule were essential for biological activity. These areas were designated as: the tail group (Region A), the linker chain (Region B), and the head group (Region C). The tail group was varied as: absent, an N—H pyrrole derivative, or an N-methyl pyrrole derivative. The linker between the head group and tail group was varied from two to four carbons and the effect of chain unsaturation was also examined. The head groups considered for analysis included 2-aminoimidazole, 2-amino-4-oxoimidazole, imidazole, tryptoplian, 2-thioimidazolone, and 2-aminothiazole (FIG. 16).

To examine each compound's ability to inhibit the formation of Pseudomonas aerziguiosa biofilms, PAO1 and PA14 were employed as the target bacterial strains using a crystal violet reporter assay. G. A. O'Toole, R. Kolter, Mol. Microbiol. 1998, 28, 449. All compounds were initially screened at 500 μM for anti-biofilm activity. IC$_{50}$ values were then determined for compounds that displayed exceptional activity in the preliminary screen followed by growth curve and colony count analysis to verify that the compounds were in fact true inhibitors of bacterial biofilm formation and not acting as microbicides inducing cell death before biofilm development had begun.

Region A SAR: Tail-group analogue synthesis and biological activity. Nearly all oroidin alkaloids are known to contain the pyrrole carboxamide moiety with various degrees of bromination and this provided the first structural element for investigation. H. Hoffmann, T. Lindel, Synthesis-Stuttgart 2003, 1753. Each analogue was prepared by a convergent synthetic approach with amide bond formation between the scaffold 4-(3-aminopropyl)-2-aminoimidazole dihydrochloride 16 and the appropriate trichloroacetyl pyrrole derivative serving as the final step. Trichloroacetyl pyrroles are known to undergo smooth amide bond formation in the presence of an unprotected 2-aminoimidazole and are among the most frequently used reagents in the total synthesis of many oroidin relatives. V. B. Birman, X. T. Jiang, *Org. Lett.* 2004, 6, 2369. D. P. O'Malley, et al., *J. Am. Chem. Soc.* 2007, 129, 4762. The necessary trichloroacetyl pyrroles were synthesized as outlined in Scheme 6. D. M. Bailey, R. E. Johnson, *J. Med. Chem.* 1973, 16, 1300. The corresponding N—H and N-methyl dibromo carboxylic acids 11 and 15 were also prepared. These simple compounds are frequently isolated in high concentrations in conjunction with the more complex oroidin alkaloids from the *Agelasidae* sponges and would serve as controls in the inhibition assay. A. E. Wright, et al., *J. Nat. Prod.* 1991, 54, 1684. A compiled activity list of all compounds synthesized and assayed at 500 µM for Region A SAR is summarized in Scheme 7.

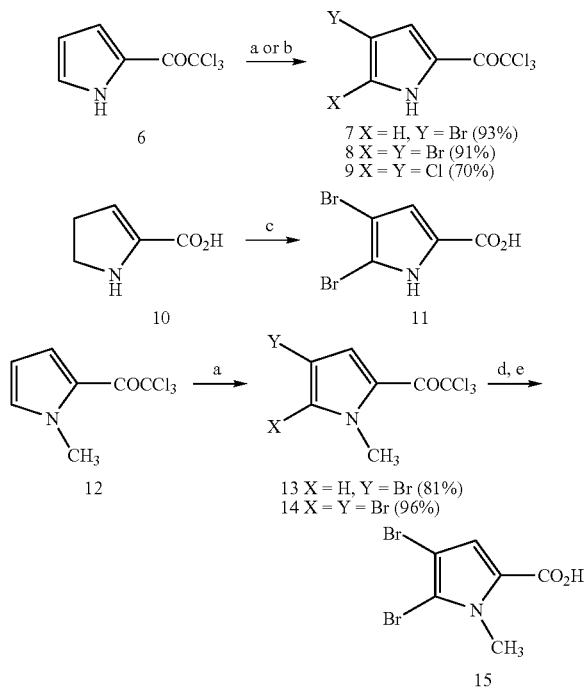

Scheme 6. Synthesis of pyrrole subunits for Region A SAR:

Reaction conditions: (a) Br$_2$, CHCl$_3$, 0° C. (b) SO$_2$Cl$_2$, CHCl$_3$, reflux (c) Br$_2$, HOAc, CHCl$_3$, 50° C., 87% (d) K$_2$CO$_3$, MeOH, 92% (e) LiOH, MeOH/THF/H$_2$O, 94%.

SCHEME 7

Region A SAR synthesis and biological evaluation.

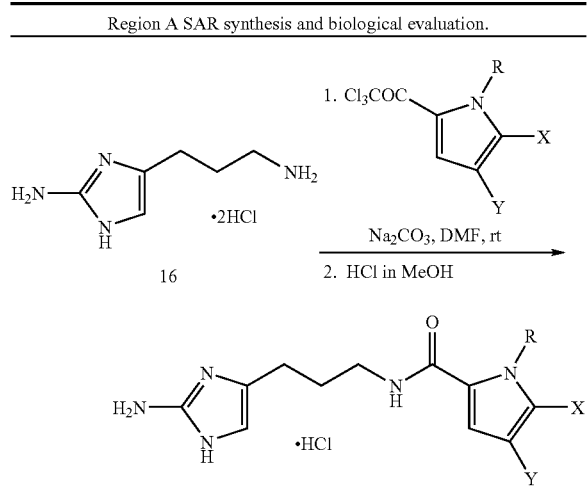

SCHEME 7-continued

| | % Yield | % Biofilm Inhibition at 500 µM vs PAO1 | % Biofilm Inhibition at 500 µM vs PA14 |
|---|---|---|---|
| 17 R = X = Y = H | 63 | <10 | 16 |
| 18 R = H, X = H, Y = Br | 74 | 74 | 86 |
| 19 R = H, X = Y = Br | 59 | 61 | 37 |
| 20 R = H, X = Y = Cl | 65 | 37 | 48 |
| 21 R = CH$_3$, X = Y = H | 58 | 25 | — |
| 22 R = CH$_3$, X = H, Y = Br | 56 | 88 | 83 |
| 23 R = CH$_3$, X = Y = Br | 63 | >95 | >95 |

The N—H pyrrole sub-class was the first group of analogues studied. The dihydro derivatives of the natural products clathrodin, (J. J. Morales, A. D. Rodriguez, *J. Nat. Prod.* 1991, 54, 629) hymenidin, (J. Kobayashi, et al. *Experientia* 1986, 42, 1176) and oroidin represent the various successive degrees of N—H pyrrole bromination and were synthesized and screened for their ability to inhibit the formation of *P. aeruginosa* biofilms (Scheme 7). As previously reported, scaffold 16 was relatively inactive against both strains (20% inhibition against PAO1, 15% against PA14). R. W. Huigens, et al., *J. Am. Chem. Soc.* 2007, 129, 6966. Dihydroclathrodin (DHC, 17) showed similar activity to the base scaffold with <10% inhibition of PAO1 and 16% inhibition of PA14 biofilm formation. Dihydrohymenidin (DHH, 18) showed a remarkable increase in activity, inhibiting the formation of PAO1 and PA14 biofilms by 74% and 86%, respectively. Addition of a second bromine atom at the 2-position on the pyrrole ring yielded dihydrooroidin (DHO, 19). It was hypothesized that activity would yet again increase but surprisingly DHO displayed a decrease in potency against both strains (PAO1 inhibition=61%, PA14 inhibition=37%).

The requirement of a particular halogen identity on the pyrrole ring was also examined by replacing both bromine atoms with less sterically demanding and less electronegative chlorine atoms (20). No known oroidin family members possess chlorine substituents on the pyrrole carboxamide subunit yet some do contain chlorinated positions in other parts of the molecule. M. Kock, et al., *Angew. Chem., Int. Ed.* 2007, 46, 6586. This venture however proved unfruitful as no substantial benefit was gained with the dichloro derivative 20, inhibiting the formation of PAO1 biofilms by 37% and PA14 biofilms by 48% at 500 µM.

Investigation into how introduction of a methyl substituent on the pyrrole nitrogen would affect activity was the next step in the SAR process for this region. This decision was based upon the observation that some naturally occurring members of the oroidin family (i.e. sventrin 24) contain an N-methylated pyrrole instead of the more commonly seen N—H pyrrole moiety. M. Assmann, et al., *J. Nat. Prod.* 2001, 64, 1593. The non-brominated derivative 21 showed a slight increase in activity when compared to DHC, as it was observed that 21 inhibited the formation of PAO1 biofilms by 25%. However, this derivative was found to be inactive against PA14. Analogous to what was observed with the N—H pyrrole subset, N-methyl dihydrohymenidin 22 showed a substantial increase in activity (88% and 83% inhibition for PAO1 and PA14, respectively). This time addition of a second bromine was observed to enhance activity as this compound, dihydrosventrin (DHS, 23), inhibited the formation of both PAO1 and PA14 biofilms by >95% at 500 µM.

All compounds that revealed >70% biofilm inhibition activity during the preliminary 500 µM screen were selected for further biological characterization. Dose response curves were generated for each compound to determine the analogue's IC$_{50}$ value against both *Pseudomonas* strains. These results are summarized in Table 4. Of the tail-modified derivatives, dihydrosventrin (DHS) was the most active with an IC$_{50}$ of 51±9 µM against PAO1 and 111±8 µM against PA14. When the tail fragment 15 was tested alone, it displayed no activity at 500 µM. This evidence further reinforces the fact that the two fragments must be covalently linked to elicit their anti-biofilm activity. Growth curves and colony counts were also performed for both PAO1 and PA14 in the presence and absence of DHS 23 at its respective IC$_{50}$ concentration. In each case, no reduction in bacterial density or viable colonies was observed, thus confirming that our compounds were true inhibitors of biofilm formation and not eliciting their activity through a microbiocidal mechanism (not shown).

TABLE 4

IC$_{50}$ values for Region A analogues.

| Compound | PAO1 IC$_{50}$(µM) | PA14 IC$_{50}$(µM) |
| --- | --- | --- |
| Dihydrohymenidin (18) | 323 ± 30 | 266 ± 23 |
| N-methyl dihydrohymenidin (22) | 348 ± 13 | 309 ± 16 |
| Dihydrosventrin (23) | 51 ± 9 | 111 ± 8 |

Dihydrosventrin (23)

The data gathered from this section of the SAR indicated a rough correlation between degree of bromination on the pyrrole ring and increased anti-biofilm activity. It was also observed that compounds bearing the N-methylated pyrrole had better potential as biofilm inhibitors, illustrated by the remarkable difference in activity between dihydrosventrin 23 and dihydrooroidin 19.

Figure 17:
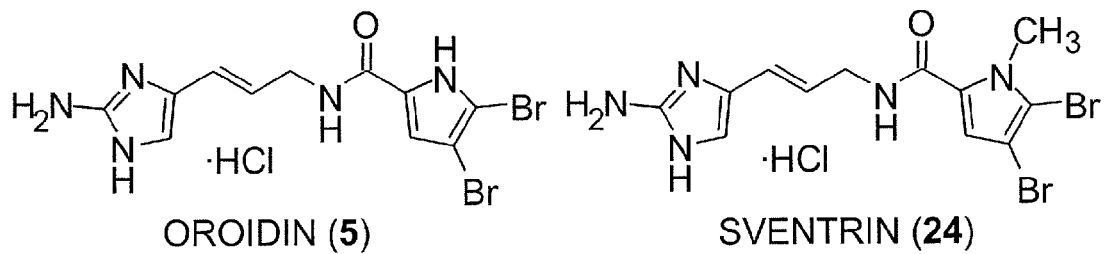
FIG. 17. $IC_{50}$ values for the natural products oroidin 5 and sventrin 24.

Region B SAR: Linker analogue synthesis and biological activity. The double bond found in oroidin is proposed to have a profound impact on the ability of the sponge to synthesize a number of more complex chemical skeletons (i.e. ageliferins, sceptrins) through dimerization type reactions. A. Al Mourabit, P. Potier, *Eur. J. Org. Chem.* 2001, 237. Discerning whether or not unsaturation was necessary for a biological response from an anti-biofilm standpoint would allow us to circumvent a low yielding extra synthetic step needed to install the double bond between the 3-4 positions in the dihydro scaffold 16. Oroidin 5 was prepared as previously reported. A. Olofson, et al., *J. Org. Chem.* 1998, 63, 1248. Sventrin 24 was synthesized using an identical synthetic approach executed for oroidin with the exception of employing 14 in the amide bond formation step. Initial screens at 500 µM revealed that both natural products inhibited the formation of PAO1 and PA14 biofilms >95%. The activity of oroidin 5 (PAO1 IC$_{50}$=190±9 µM, PA14 IC$_{50}$=166±19 µM) was exceptionally better than its dihydro congener, which was not even considered a candidate for IC$_{50}$ value determination (vide supra). In contrast, the IC$_{50}$ values of sventrin 24 (IC$_{50}$=75±5 µM PAO1, IC$_{50}$=115±3 µM PA14) were very similar to those of its saturated counterpart (FIG. 17). This seemed to indicate that as we begin to fine tune our scaffolds to maximize anti-biofilm activity, unsaturation within the linker is not necessary to elicit maximum biological activity.

As carried out with DHS, follow tip growth curve and colony count analysis of PAO1 and PA14 grown in the presence or absence of either natural product at their respective IC$_{50}$ concentrations did not induce microbial cell death.

Given that a fully saturated chain, when coupled to the 4,5-dibromo-N-methylpyrrole subunit yielded a compound (DHS) with the highest activity, we then elected to study the effect that linker length had upon biological activity. Homologues of DHS that contained a 2-methylene and a 4-methylene spacer between the 2-Al head and the pyrrole tail were envisioned. These compounds were quickly accessed as outlined in Scheme 8. Briefly, commercially available 1,4-diamino-2-butanone dihydrochloride 25 was condensed with cyanamide under pH-controlled conditions to yield the 2-methylenie spacer 2-Al 26 (T. Vitali, et al., *Farmaco* 1984, 39, 70), which was subsequently coupled to fragment 14 to deliver target 27. The 4-methylene spacer was generated through Akabori reduction of lysine methyl ester 28 to produce the corresponding α-amino aldehyde, (Akabori, *Ber. Deut. Chem. Ges.* 1933, 66, 151; G. C. Lancini, E. Lazzari, *J. Heterocycl. Chem.* 1966, 3, 152) which, upon cyclization with cyanamide and ensuing amide bond formation, afforded the 2-Al 30.

Scheme 8. Region B SAR linker synthesis;

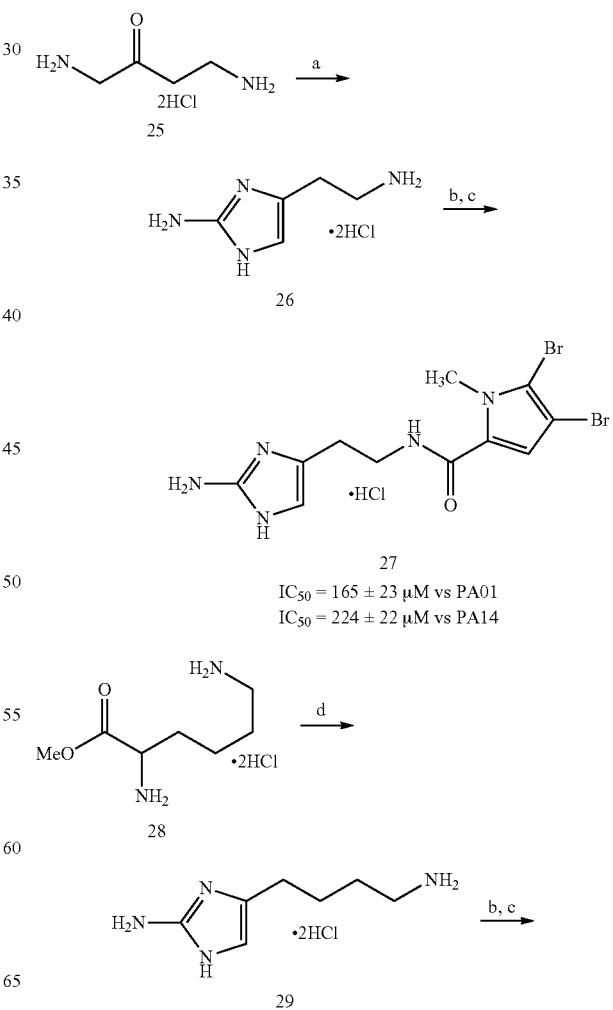

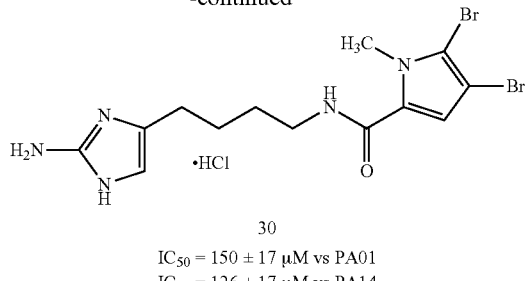

30

IC$_{50}$ = 150 ± 17 μM vs PA01
IC$_{50}$ = 126 ± 17 μM vs PA14

Reaction conditions: (a) NH$_2$CN, H$_2$O, 95° C., pH = 4.3, 62% (b) 14, Na$_2$CO$_3$, DMF, rt (c) HCl in MeOH, 27: 64%, 30: 54% (d) Na/Hg, H$_2$O, 5° C., pH = 1.5 then NH$_2$CN, H$_2$O, 95° C., pH = 4.3, 18%.

Initial screens at 500 μM revealed that each compound, like the parent compound DHS, inhibited the formation of PAO1 and PA14 biofilms by >95%. IC$_{50}$ values for both 27 and 30 did, however, indicate the subtle effects that alkyl linker length had upon activity, with both modifications decreasing activity in comparison to DHS. Increasing the alkyl chain length to 4-methylene units elicited the smallest drop in activity (PAO1 IC$_{50}$=150±17 μM, PA14 IC$_{50}$=126±17 μM), while the reduction in potency was slightly more pronounced when decreasing the alkyl chain length to 2-methylene units (PAO1 IC$_{50}$=165±23 μM, PA14 IC$_{50}$=224±22 μM). Colony counts and growth curves performed with these homologues revealed no microbiocidal activity at their respective IC$_{50}$ values.

Screening of these various linker analogues quickly revealed two important SAR features of the oroidin scaffold in terms of anti-biofilm activity. First, the optimum chain length between the 2-AI head and pyrrole tail was three carbon units. Second, unsaturation was not necessary to elicit a biological response, thus eliminating the need for an additional synthetic step which otherwise would have been needed for analogue synthesis.

Figure 18:
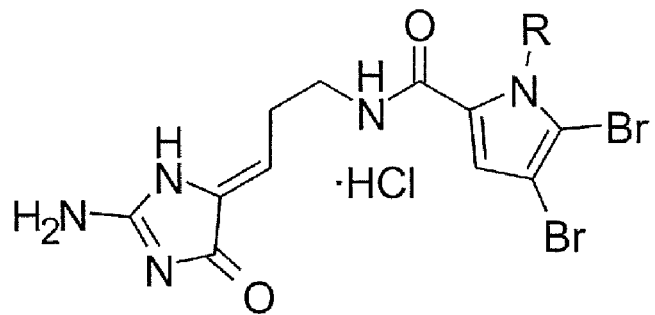
FIG. 18. 2-amino-4-oxoimidazole analogues.

Region C SAR: Head-group analogue synthesis and biological activity. Given the ubiquitous nature of the 2-aminoimidazole group in oroidin alkaloids, a substantial effort was made to delineate the importance of the 2-AI head group. We first focused on determining the ramifications of oxidizing the 2-AI ring at the 4-position. The natural product dispacamide (F. Cafieri, et al., Tet. Lett. 1996, 37, 3587) 31 and its N-methyl congener 32 were synthesized and subsequently assayed for inhibition of PAO1 and PA14 biofilms (FIG. 18). Dispacamide was prepared as previously reported (A. Olofson, et al., J. Org. Chem. 1998, 63, 1248) while dihydrosventrin 23 was also oxidized with molecular bromine in DMSO to afford its requisite N-methyl analogue. Each compound showed a substantial reduction in activity with <20% PAO1 and PA14 biofilm formation inhibition at 500 μM.

The repercussions of atomic deletion or full head group replacement within Region C were investigated next. This was examined by replacement of the 2-AI group with a tryptophan residue or an imidazole group lacking the 2-amino functionality. It was deemed unnecessary to delineate a synthesis for a 3-carbon linker of trytophan and imidazole when their 2-carbon homologues were commercially available and could be directly compared to the corresponding 2-AI derivative with a 2-methylene unit linker which had already been characterized. Tryptamine hydrochloride or histamine dihydrochloride were coupled to all of the different trichloroacetyl pyrroles discussed in the Region A SAR portion of this report and assayed for biofilm inhibition activity (Scheme 9).

SCHEME 9

Region C SAR synthesis and biological evaluation.

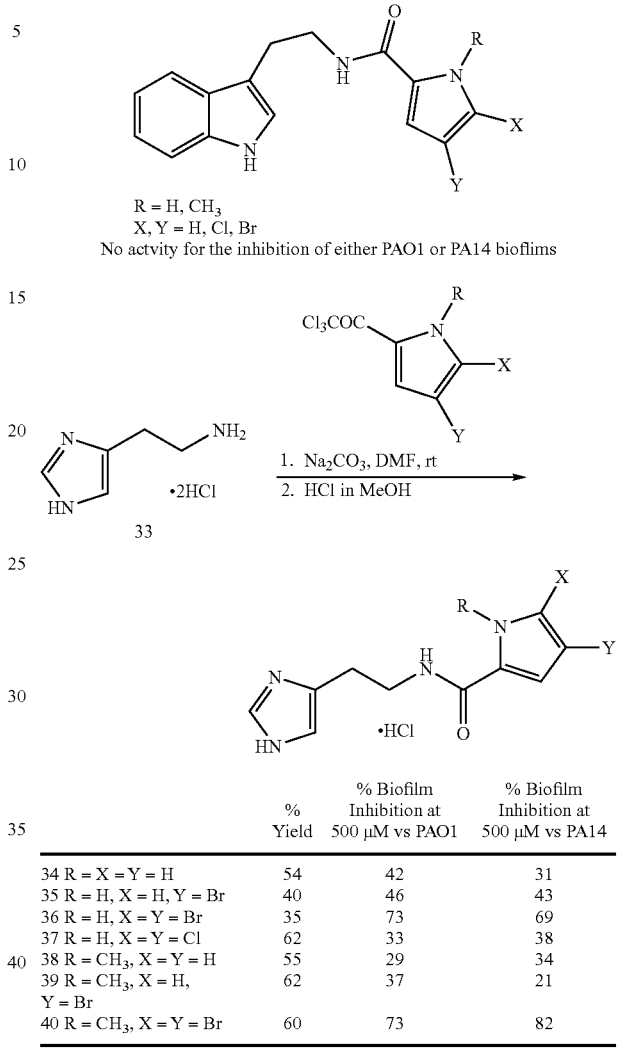

| | % Yield | % Biofilm Inhibition at 500 μM vs PAO1 | % Biofilm Inhibition at 500 μM vs PA14 |
|---|---|---|---|
| 34 R = X = Y = H | 54 | 42 | 31 |
| 35 R = H, X = H, Y = Br | 40 | 46 | 43 |
| 36 R = H, X = Y = Br | 35 | 73 | 69 |
| 37 R = H, X = Y = Cl | 62 | 33 | 38 |
| 38 R = CH$_3$, X = Y = H | 55 | 29 | 34 |
| 39 R = CH$_3$, X = H, Y = Br | 62 | 37 | 21 |
| 40 R = CH$_3$, X = Y = Br | 60 | 73 | 82 |

Figure 19:
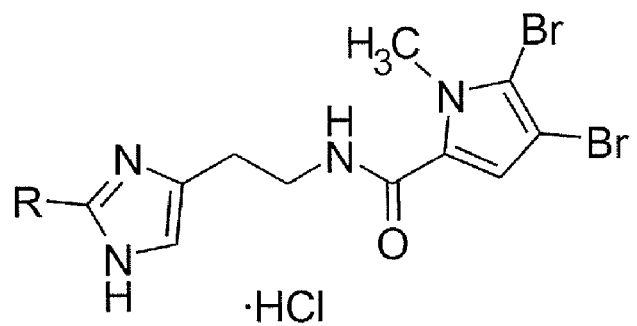
FIG. 19. Direct comparison of an atom-deletion effect in Region C.

Replacement of the 2-AI subunit with a tryptophan abolished all activity at 500 μM, no matter what pyrrole derivative was appended to the tail. Removal of the 2-amino group was not as deleterious, as each compound we initially assayed at 500 μM showed varying degrees of anti-biofilm activity against both PAO1 and PA14. IC$_{50}$ value determination of analogue 40 (IC$_{50}$=277±35 μM PAO1, IC$_{50}$=203±25 μM PA14) for comparison to its 2-AI 2-methylene spacer homologue 27 (PAO1 IC$_{50}$=165±23 μM, PA14 IC$_{50}$=224±22 μM), revealed that in comparison to 27, a substantial drop in activity against PAO1 is noted along with slightly better activity against PA14 (FIG. 19). Subsequent growth curves and colony counts indicated that 40 was not inhibiting biofilm development through microbiocidal activity.

Finally, we inquired how single atom changes within the 2-AI subunit would affect anti-biofilm activity. To this end, we elected to synthesize the 2-thioimidazolone and 2-aminothiazole (2-AT) scaffolds for SAR study. Condensation of an α-amino carbonyl compound with an isocyanate is well known, (A. C. B. Sosa, et al., Org. Lett. 2000, 2, 3443) and provided the basis for the synthesis of the 2-thioimidazolone scaffold 42. Similar to the known route to access 2-AI scaffold 16, Akabori reduction of ornithine methyl ester followed immediately by cyclization with KSCN under pH controlled conditions afforded the 2-thioimidazolone 42. Acylation of the terminal amine was accomplished with conditions adopted from the Region A SAR study to afford 43-49 in modest yields (Scheme 10). All derivatives in this subset were able to inhibit biofilm formation throughout a range of values at 500 µM.

SCHEME 10

Region C SAR synthesis and biological evaluation.

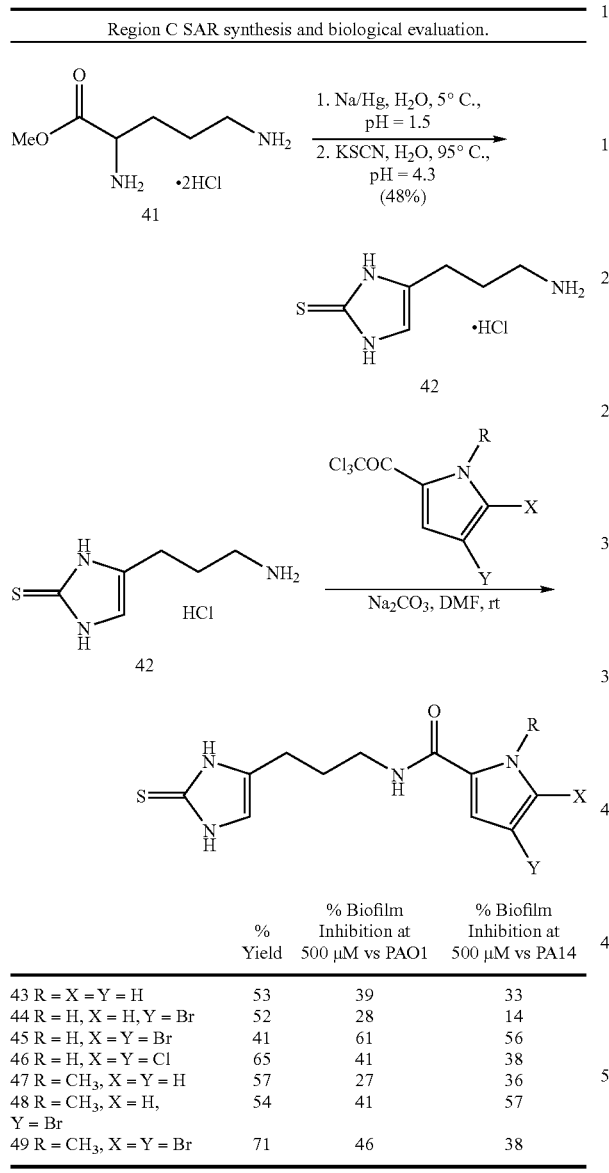

| | % Yield | % Biofilm Inhibition at 500 µM vs PAO1 | % Biofilm Inhibition at 500 µM vs PA14 |
|---|---|---|---|
| 43 R = X = Y = H | 53 | 39 | 33 |
| 44 R = H, X = H, Y = Br | 52 | 28 | 14 |
| 45 R = H, X = Y = Br | 41 | 61 | 56 |
| 46 R = H, X = Y = Cl | 65 | 41 | 38 |
| 47 R = CH$_3$, X = Y = H | 57 | 27 | 36 |
| 48 R = CH$_3$, X = H, Y = Br | 54 | 41 | 57 |
| 49 R = CH$_3$, X = Y = Br | 71 | 46 | 38 |

2-AT's are known to possess biological activity and thus were deemed a logical choice for head group study. J. C. Eriks, et al., *J. Med. Chem.* 1992, 35, 3239. J. L. Kane, et al., *Bioorg. Med. Chem. Lett.* 2003, 13, 4463. To affect the synthesis of the 2-AT scaffold, a new synthetic plan was necessary to selectively install a sulphur atom at the 1-position in the ring (Scheme 11). Synthesis commenced with acyl chloride formation of the known 4-phthalimidobutanoic acid 50. W. J. Kruper, et al., *J. Org. Chem.* 1993, 58, 3869. This was followed by diazomethane homologation and concomitant quench with concentrated HBr, which afforded the α-bromoketone. Cyclization of the α-bromoketone with thiourea under neutral conditions cleanly and regioselectively installed the 2-AT ring (51). J. C. Eriks, et al., *J. Med. Chem.* 1992, 35, 3239. A. Hantzsch, V. Traumann, *Berichte* 1888, 21, 938. Deprotection of the phthlamide protecting group was accomplished with hydrazine in methanol to deliver the 2-AT scaffold. Again, acylation of the terminal amine was accomplished as previously outlined to afford the final target analogues. The 2-AT sub-library was completely inactive at 500 µM as seen with the tryptophan derivatives.

Scheme 11. Region C SAR synthesis:

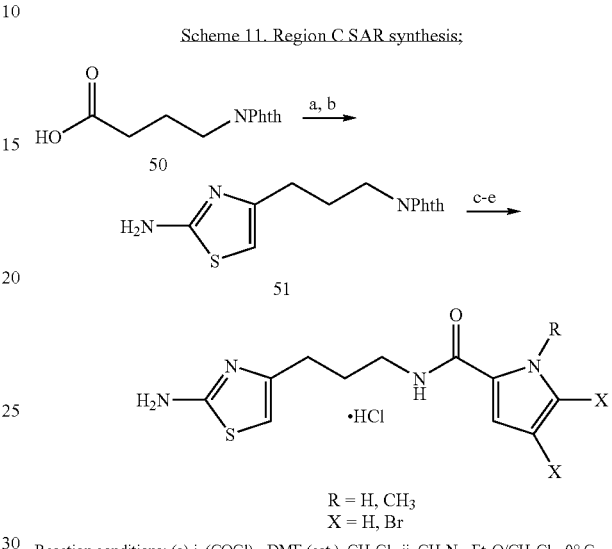

R = H, CH$_3$
X = H, Br

Reaction conditions: (a) i. (COCl)$_2$, DMF (cat.), CH$_2$Cl$_2$ ii. CH$_2$N$_2$, Et$_2$O/CH$_2$Cl$_2$, 0° C. iii. conc. HBr, 84% (b) thiourea, DMF, 0° C. to 25° C., 97% (c) N$_2$H$_4$, MeOH, 25° C. to 55° C., 90% (d) K$_2$CO$_3$, 6/8/12/14, DMF (e) HCl in MeOH.

These single atom replacements concluded the SAR study of Region C. Oxidation of the 2-AI ring in DHS proved detrimental by eliminating nearly all biological activity. In addition, an imidazole-based motif remained important in the ability of these compounds to inhibit the formation of *Pseudomonas* biofilms despite trading out the 2-AI subunit for a variety of functionally unique moieties.

In conclusion, through the generation of a 50-compound library, numerous trends become apparent when the SAR data is reviewed in the context of anti-biofilm activity. First, a 3-methylene linker between the 2-AI head and pyrrole tail elicits maximum biological activity. Second, unsaturation within the linker does not appear to be necessary to augment biological response once the other regions of the oroidin template are fine-tuned for maximum activity. Third, an imidazole or 2-AI head is necessary to maintain activity. Fourth, derivatives that contain di-bromonated N-methyl pyrroles have the tendency to be the most potent analogues within their respective sub-libraries. These trends culminated in the identification of a lead candidate, DHS 23, as a very potent and non-toxic inhibitor of *Pseudomonas* biofilm formation.

Experimental. Stock solutions of all compounds assayed for biological activity were prepared in DMSO and stored at room temperature. The amount of DMSO used in both inhibition and dispersion screens did not exceed 1% (by volume). Preliminary screens at 500 µM were performed in duplicate. IC$_{50}$ dose response assays were preformed in triplicate or more. *P. aeruginosa* strains PAO1 and PA14 were graciously supplied by the Wozniak group at Wake Forest University School of Medicine.

General Static Inhibition Assay Protocol for *Pseudomonas aeruginosa*. An overnight culture of the wild type strain was subculture at an OD$_{600}$ of 0.10 into LBNS along with a predetermined concentration of the small molecule to be tested for biofilm inhibition. Samples were then aliquoted (100 μL) into the wells of a 96-well PVC microtiter plate. The microtiter dishes were covered and sealed before incubation under stationary conditions at 37° C. for 24 hours. After that time, the medium was discarded and the plates thoroughly washed with water. The wells were then inoculated with a 0.1% aqueous solution of crystal violet (100 μL) and allowed to stand at ambient temperature for 30 minutes. Following another thorough washing with water the remaining stain was solubilized with 200 μL of 95% ethanol. Biofilm inhibition was quantitated by measuring the $OD_{540}$ for each well by transferring 125 μL of the ethanol solution into a fresh polystyrene microtiter dish for analysis.

All reagents including anhydrous solvents used for the chemical synthesis of the library were purchased from commercially available sources and used without further purification unless otherwise noted. All reactions were run under either a nitrogen or argon atmosphere. Flash silica gel chromatography was performed with 60 Å mesh standard grade silica gel from Sorbtech. $^1H$ and $^{13}C$ NMR spectra were obtained using Varian 300 MHz or 400 MHz spectrometers. NMR solvents were purchased from Cambridge Isotope Labs and used as is. Chemical shifts are given in parts per million relative to DMSO-$d_6$ (δ 2.50), $CD_3OD$ (δ 3.31) and $CDCl_3$ (δ 7.27) for proton spectra and relative to DMSO-$d_6$ (δ 39.51), $CD_3OD$ (δ 49.00) and $CDCl_3$ (δ 77.21) for carbon spectra with an internal TMS standard. High-resolution mass spectra were obtained at the North Carolina State Mass Spectrometry Laboratory for Biotechnology. FAB experiments were carried with a JOEL HX110HF mass spectrometer while ESI experiments were carried out on Agilent LC-TOF mass spectrometer.

1-(4-bromo-1H-pyrrol-2-yl)-2,2,2-trichloro-ethanone (7). 2-trichloroacetyl pyrrole 6 (5.00 g, 23.3 mmol) was dissolved in anhydrous chloroform (20 mL). The solution was cooled to −10° C. before the drop-wise addition of bromine (1.20 mL, 23.3 mmol) to the flask. Once addition was complete the reaction was allowed to warm to room temperature on its own accord while stirring for an additional 30 minutes. The reaction was poured into water (40 mL) and extracted with chloroform (3×20 mL). The combined organic layers were washed with sat. $NaHCO_3$ (2×30 mL), brine (1×20 mL), dried over anhydrous sodium sulfate, filtered, and evaporated to dryness. Purification of the residue by column chromatography (Hexanes/Diethyl Ether 95:5) yielded the title compound 7 (6.37 g, 93%) as an off-white solid: $^1H$ NMR (300 MHz, DMSO-$d_6$) δ 12.86 (s, 1H), 7.54 (s, 1H), 7.32 (s, 1H); $^{13}C$ NMR (100 MHz, DMSO-$d_6$) δ 171,67, 129.06, 122.01, 121.54, 97.60, 94.56; HRMS (FAB) calcd for $C_6H_3BrCl_3NO$ ($M^+$) 288.8464, found 288.8479.

1-(4-bromo-1-methyl-pyrrol-2-yl)-2,2,2-trichloro-ethanone (13). Using the same general procedure as used for the synthesis of 1-(4-bromo-1H-pyrrol-2 -yl)-2,2,2-trichloro-ethanone 7, 5.00 g of 2-trichloroacetyl-1-methyl pyrrole afforded 5.46 g (81%) of the title compound 13 as a white solid: $^1H$ NMR (300 MHz, DMSO-$d_6$) δ 7.66 (d, 1H, J=1.2 Hz), 7.42 (d, 1H, J=1.8 Hz), 3.91 (s, 3 H); $^{13}C$ NMR (100 MHz, DMSO-$d_6$) δ 171.48, 134.40, 123.62, 121.19, 95.36, 95.12; HRMS (FAB) calcd for $C_7H_6BrCl_3NO$ ($MH^+$) 303.8698, found 303.8678.

2,2,2-trichloro-1-(4,5-dibromo-1H-pyrrol-2-yl)-ethanone (8). 2-trichloroacetyl pyrrole 6 (5.00 g, 23.3 mmol) was dissolved in anhydrous chloroform (20 mL). The solution was cooled to −10° C. before the drop-wise addition of bromine (2.64 mL, 51.3 mmol) to the reaction. Once addition was complete the reaction was allowed to warm to room temperature on its own accord while stifling for an additional 30 minutes. The reaction was poured into water (40 mL) and extracted with chloroform (3×20 mL). The combined organic layers were washed with sat. $NaHCO_3$ (2×30 mL), brine (1×20 mL), and dried over anhydrous sodium sulfate. Filtration and evaporation afforded the crude product which was recrystallized from hexanes to deliver 7.93 g (91%) of the title compound 8 as an off-white solid: $^1H$ NMR (300 MHz, DMSO-$d_6$) δ 13.75 (s, 1H), 7.40 (s, 1H); $^{13}C$ NMR (100 MHz, DMSO-$d_6$) δ 170.94, 123.30, 122.45, 114.62, 100.88, 94.08; HRMS (FAB) calcd for $C_6H_2Br_2Cl_3NO$ ($M^+$) 366.7569, found 366.7556.

2,2,2-trichloro-1-(4,5-dibromo-1-methyl-pyrrol-2-yl)-ethanone (14). Using the same general procedure as used for the synthesis of 2,2,2-trichloro-1-(4,5 -dibromo-1H-pyrrol-2-yl) -ethanone 8, 5.00 g of 2-trichloroacetyl-1-methyl pyrrole 12 gave 8.14 g (96%) of the title compound 14 as white needles. $^1H$ NMR (300 MHz, DMSO-$d_6$) δ 7.60 (s, 1H), 3.96 (s, 3H); $^{13}C$ NMR (100 MHz, DMSO-$d_6$) δ 170.86, 123.81, 122.68, 120.58, 99.58, 94.89, 37.60; HRMS (FAB) calcd for $C_7H_4Br$—$Cl_3NO$ ($M^+$) 380.7725, found 380.7744.

2,2,2-trichloro-1-(4,5-dichloro-1H-pyrrol-2-yl)-ethanone (9). 2-trichloroacetyl pyrrole 6 (5.00 g, 23.5 mmol) was dissolved in anhydrous chloroform (10 mL) and the reaction flask was covered in aluminum foil to exclude light. Sulfuryl chloride (4.20 mL, 51.8 mmol), was then charged in the flask and the reaction was refluxed for 16 h before being cooled to room temperature and poured into cold water (100 mL). The aqueous layer was removed and washed with dichloromethane (2×25 mL). The combined organic layers were then washed with sat. $NaHCO_3$ (3×35 mL), dried over anhydrous sodium sulfate, filtered, and concentrated in vacuo. The residue was purified by column chromatography (Hexanes/Diethyl Ether 95:5) to afford 4.61 g (70%) of the desired compound 9 as a white solid: $^1H$ NMR (300 MHz, DMSO-$d_6$) δ 13.84 (s, 1H), 7.41 (s, 1H); $^{13}C$ NMR (100 MHz, DMSO-$d_6$) δ 171.2, 123.6, 119.9, 119.7, 110.8, 94.8; HRMS (FAB) calcd for $C_6H_2Cl_5NO$ ($M^+$) 278.8579, found 278.8573.

4,5-dibromo-1H-pyrrole-2-carboxylic acid (11). Pyrrole-2-carboxylic acid 10 (1.00 g, 9.00 mmol), was dissolved in anhydrous chloroform (10 mL) and glacial HOAc (2 mL). To the resulting cloudy solution was slowly added bromine (0.971 mL, 18.9 mmol) at room temperature and once addition was complete the reaction was heated to 50° C. for 5 h. After cooling to ambient temperature the reaction was partitioned between water (30 mL) and chloroform (40 mL). The organic layer was rinsed with water (2×30 mL) and 10% $K_2CO_3$ (40 mL). The $K_2CO_3$ extract was then washed with chloroform (2×20 mL) and acidified to pH=3 with an aqueous solution of 4N HCl. The precipitate was collected by vacuum filtration and the filter cake rinsed with water (15 mL) to afford the target compound 11 (2.10 g, 87%) as a white solid: $^1H$ NMR (400 MHz, DMSO-$d_6$) δ 12.80 (bs, 1H), 6.82 (s, 1H); $^{13}C$ NMR (100 MHz, DMSO-$d_6$) δ 160.43, 125.37, 116.73, 106.50, 98.70; HRMS (FAB) calcd for $C_5H_3Br_2NO$ ($M^+$) 266.8531, found 266.8525.

4,5-dibromo-1-methyl-pyrrole-2-carboxylic acid methyl ester. 2,2,2 -trichloro-1-(4,5-dibromo-1-methyl-1H-pyrrol-2-yl)-ethanone 14 (1.00 g, 2.60 mmol), anhydrous potassium carbonate (0.719 g, 5.20 mmol), and anhydrous methanol (20 mL) were charged into a reaction flask. The resulting suspension was stirred for 16 h at room temperature upon which the reaction was quenched with water (10 mL). The methanol was removed under reduced pressure and the residue partitioned between ethyl acetate (100 mL) and water (20 mL). The organic layer was subsequently washed with sat. $NaHCO_3$ (2×30 mL), brine (2×20 mL), dried over anhydrous sodium sulfate, and filtered. Evaporation of the filtrate yielded the title compound (0.710 g, 92%) as a white solid: $^1$H NMR (300 MHz, DMSO-$d_6$) δ 7.05 (s, 1H), 3.90 (s, 3H), 3.76 (s, 3H); $^{13}$C NMR (75 MHz, DMSO-$d_6$) δ 159.38, 123.62, 118.51, 113.93, 98.06, 51.58, 35.78; HRMS (FAB) calcd for $C_7H_7Br_2NO_2$ (M$^+$) 294.8844, found 294.8861.

4,5-dibromo-1-methyl-pyrrole-2-carboxylic acid (15). 4,5-dibromo-1-methyl-1H-pyrrole-2-carboxylic acid methyl ester (0.675 g, 2.27 mmol), lithium hydroxide (0.436 g, 18.19 mmol), methanol (12 mL), tetrahydrofuran (4 mL), and water (4 mL) were stirred for 16 h at ambient temperature. The pH was then adjusted to 7.0 with an aqueous solution of 4N HCl. The organics were removed by rotary evaporation and the resulting residue diluted with water (15 mL). Acidification of the aqueous layer to pH=3 with 4N HCl afforded a white solid which was collected by vacuum filtration. The filter cake was rinsed with water (10 mL) to give the title compound 15 (0.601 g, 94%) as a white solid: $^1$H NMR (400 MHz, DMSO-$d_6$) δ 12.83 (s, 1H), 7.00 (s, 1H), 3.90 (s, 3H); $^{13}$C NMR (100 MHz, DMSO-$d_6$) δ 160.51, 124.74, 118.41, 113.07, 97.72, 35.64; HRMS (FAB) calcd for $C_6H_5Br_2NO_2$ (M$^+$) 280.8687, found 280.8676.

4-(3-amino-propyl)-1H-imidazol-2-ylamine dihydrochloride (16). Prepared as previously reported.[37] $^1$H NMR (300 MHz, DMSO-$d_6$) δ 12.04 (br s, 1H), 8.25 (br s, 2H), 7.41 (s, 2H), 6.65 (s, 1H), 2.75 (t, 2H, J=7.2), 2.52 (m, 2H), 1.85 (tt, 2H, J=7.5, 14.7 Hz); $^{13}$C NMR (100 MHz, DMSO-$d_6$) δ 146.9, 125.4, 108.9, 37.7, 25.5, 21.1; HRMS (FAB) calcd for $C_6H_{12}N_3S$ (MH$^+$) 158.0752, found 158.0743.

1H-pyrrole-2-carboxylic acid [3-(2-amino-1H-imidazol-4-yl)-propyl]-amide hydrochloride (17). 4-(3-amino-propyl)-1H-imidazol-2-ylamine dihydrochloride 16 (0.100 g, 0.458 mmol), 2-trichloroacetyl pyrrole 6 (0.103 g, 0.488 mmol), and anhydrous sodium carbonate (0.172 g, 1.63 mmol), were dissolved in anhydrous N,N-dimethylformamide (5 mL). The reaction was stirred at ambient temperature for 16 h. Evaporation of the reaction under reduced pressure and purification of the residue by column chromatography (CH$_2$Cl$_2$/MeOH sat. NH$_3$ 85:15) afforded the desired compound in its free base form. Addition of a single drop of concentrated hydrochloric acid to a methanol solution (8 mL) and evaporation under reduced pressure yielded 0.078 g (63%) of the title compound 17 as a white solid: $^1$H NMR (300 MHz, DMSO-$d_6$) δ 12.07 (s, 1H), 11.59 (s, 1H), 11.45 (s, 1H), 8.14 (t, 1H, J=5.1 Hz), 7.30 (s, 2H), 6.81 (m, 2H), 6.74 (s, 1H), 6.59 (s, 1H), 6.04 (s, 1H), 3.19 (dt, 2H, J=6.6, 12.6 Hz), 2.42 (t, 2H, J=6.9 Hz), (tt, 2H, J=6.6, 13.8 Hz); $^{13}$C NMR (100 MHz, DMSO-$d_6$) δ 160.74, 146.76, 126.43, 126.40, 121.13, 110.28, 108.65, 108.50, 37.59, 28.14, 21.60; HRMS (ESI) calcd for $C_{11}H_{16}N_5O$ (MH$^+$) 234.1349, found 234.1354.

4-bromo-1H-pyrrole-2-carboxylic acid [3-(2-amino-1H-imidazol-4-yl)-propyl]-amide hydrochloride (18). Using the same general procedure as used for the synthesis of 1H-pyrrole-2-carboxylic acid [3-(2-amino-1H-imidazol-4-yl)-propyl]-amide hydrochloride 17, 0.132 g of 4-(3-amino-propyl)-1H-imidazol-2-ylamine dihydrochloride 16 gave the target compound 18 (0.159 g, 74%) as an off-white solid: $^1$H NMR (300 MHz, DMSO-$d_6$) δ 12.20 (s, 1H), 11.85 (s, 1H), 11.57 (s, 1H), 8.23 (m, 1H), 7.31 (s, 2H), 6.97 (d, 1H, J=1.5 Hz), 6.86 (d, 1H, J=1.5 Hz), 6.61 (s, 1H), 3.21 (m, 2H), 2.44 (t, 2H, J=7.2 Hz), 1.73 (m, 2H); $^{13}$C NMR (75 MHz, DMSO-$d_6$) δ 159.63, 146.68, 126.99, 126.40, 121.06, 111.61, 108.70, 94.90, 37.67, 27.91, 21.56; HRMS (FAB) calcd for $C_{11}H_{15}BrN_5O$ (MH$^+$) 312.0460, found 312.0475.

4,5-dibromo-1H-pyrrole-2-carboxylic acid [3-(2-amino-1H-imidazol-4-yl)-propyl]-amide hydrochloride (19). Using the same general procedure as used for the synthesis of 1H-pyrrole-2-carboxylic acid [3-(2-amino-1H-imidazol-4-yl)-propyl]-amide hydrochloride 17, 0.100 g of 4-(3-amino-propyl)-1H-imidazol-2-ylamine dihydrochloride 16 afforded 0.117 g (59%) of the title compound 19 as an off-white solid: $^1$H NMR (300 MHz, DMSO-$d_6$) δ 8.33 (t, 1H, J=5.4 Hz), 7.07 (s, 2H), 6.95 (s, 1H), 6.56 (s, 1H), 3.22 (dt, 2H, J =6.0, 12.3 Hz), 2.43 (t, 2H, J=7.2 Hz), 1.73 (tt, J=6.9, 13.8 Hz); $^{13}$C NMR (100 MHz, DMSO-$d_6$) δ 158.92, 146.87, 128.31, 126.75, 112.88, 108.82, 104.33, 97.76, 37.74, 27.89, 21.74; HRMS (FAB) calcd for $C_{11}H_{14}Br_2N_5O$ (MH$^+$) 389.9565, found 389.9570.

4,5-dichloro-1H-pyrrole-2-carboxylic acid [3-(2-amino-1H-imidazol-4-yl)-propyl]-amide hydrochloride (20). Using the same general procedure as used for the synthesis of 1H-pyrrole-2-carboxylic acid [3-(2-amino-1H-imidazol-4-yl)-propyl]-amide hydrochloride 17, 0.200 g of 4-(3-amino-propyl)-1H-imidazol-2-ylamine dihydrochloride 16 afforded 0.204 g (65%) of the title compound 20 as a white solid: $^1$H NMR (300 MHz, DMSO-$d_6$) δ 8.32 (t, 1H, J=4.8 Hz), 6.91 (s, 2H), 6.53 (s, 1H), 3.21 (dt, 2H, J=6.6, 12.6 Hz), 2.42 (t, 2H, J=7.2 Hz), 1.72 (tt, 2H, J=7.5, 14.1 Hz); $^{13}$C NMR (75 MHz, DMSO-$d_6$) δ 159.15, 147.11, 127.31, 125.14, 114.75, 109.82, 108.99, 107.77, 37.83, 28.03, 22.04; HRMS (ESI) calcd for $C_{11}H_{14}C_{12}N_5O$ (MH$^+$) 302.0569, found 302.0569.

1-methyl-pyrrole-2-carboxylic acid [3-(2-amino-1H-imidazol-4-yl)-propyl]-amide hydrochloride (21). Using the same general procedure as used for the synthesis of 1H-pyrrole-2-carboxylic acid [3-(2-amino-1H-imidazol-4-yl)-propyl]-amide hydrochloride 17, 0.300 g of 4-(3-amino-propyl)-1H-imidazol-2-ylamine dihydrochloride 16 delivered 0.229 g (58%) of the target compound 21 as a pale yellow solid: $^1$H NMR (300 MHz, DMSO-$d_6$) δ 8.03 (t, 1H, J=5.1 Hz), 6.86 (m, 1H), 6.75 (m, 1H), 6.32 (s, 1H), 5.98 (m, 1H), 5.86 (br s, 2H), 3.82 (s, 3H), 3.17 (dt, 2H, J=6.3, 13.2 Hz), 2.36 (t, 2H, J=7.2 Hz), (tt, 2H, J=7.2, 14.1 Hz); $^{13}$C NMR (75 MHz, DMSO-$d_6$) δ 161.39, 148.11, 129.74, 127.47, 125.72, 112.09, 109.63, 106.53, 38.00, 36.15, 28.65, 23.30; HRMS (ESI) calcd for $C_{12}H_{18}N_5O$ (MH$^+$) 248.1506, found 248.1514.

4-bromo-1-methyl-pyrrole-2-carboxylic acid [3-(2-amino-1H-imidazol-4-yl)-propyl]-amide hydrochloride (22). Using the same general procedure as used for the synthesis of 1H-pyrrole-2-carboxylic acid [3-(2-amino-1H-imidazol-4-yl)-propyl]-amide hydrochloride 17, 0.150 g of 4-(3-amino-propyl)-1H-imidazol-2-ylamine dihydrochloride 16 afforded 0.142 g (56%) of the desired compound 22 as a pale yellow solid: $^1$H NMR (300 MHz, DMSO-$d_6$) δ 8.17 (t, 1H, J=5.7 Hz), 7.08 (d, 1H, J=1.2 Hz), 6.91 (s, 2H), 6.85 (d, 1H, J=1.5 Hz), 6.52 (s, 1H), 3.80 (s, 3H), 3.17 (dt, 2H, J=6.3, 12.9 Hz), 2.41 (t, 2H, J=7.2 Hz), 1.71 (m, 2H); $^{13}$C NMR (100 MHz, DMSO-$d_6$) δ 160.29, 147.23, 127.39, 126.87, 126.43, 113.60, 108.94, 92.89, 37.75, 36.33, 28.02, 22.08; HRMS (ESI) calcd for $C_{12}H_{17}BrN_5O$ (MH$^+$) 326.0610, found 326.0613.

4,5-dibromo-1-methyl-pyrrole-2-carboxylic acid [3-(2-amino-1H-imidazol-4-yl)-propyl]-amide hydrochloride (23). Using the same general procedure as used for the synthesis of 1H-pyrrole-2-carboxylic acid [3-(2-amino-1H-imidazol-4-yl)-propyl]-amide hydrochloride 17, 0.200 g of 4-(3-amino-propyl)-1H-imidazol-2-ylamine dihydrochloride 16 gave 0.258 g (63%) of the title compound 23 as a white solid: $^1$H NMR (300 MHz, DMSO-$d_6$) δ 12.06 (s, 1H), 11.59 (s, 1H), 8.31 (t, 1H, J=5.4 Hz), 7.32 (s, 2H), 7.03 (s, 1H), 6.60 (s, 1H), 3.87 (s, 3H), 3.18 (dt, 2H, J=6.3, 12.3 Hz), 2.45 (t, 2H, J=7.8 Hz), 1.73 (m, 2H); $^{13}$C NMR (75 MHz, DMSO-$d_6$) δ 159.77, 147.30, 127.99, 127.77, 114.00, 110.43, 109.06, 96.86; 37.94, 35.38, 27.96, 22.28; HRMS (FAB) calcd for $C_{12}H_{16}Br_2N_5O$ (MH$^+$) 403.9722. found 403.9728.

oroidin hydrochloride (5). Prepared as previously reported.[37] $^1$H NMR (300 MHz, DMSO-d$_6$) δ 12.78 (s, 1H), 12.54 (s, 1H), 11.89 (s, 1H), 8.55 (t, 1H, J=6.0 Hz), 7.47 (s, 2H), 6.99 (d, 1H, J=3.0 Hz), 6.90 (s, 1H), 6.17 (m, 2H), 3.95 (m, 2H); $^{13}$C NMR (100 MHz, DMSO-d$_6$) δ 158.73, 147.46, 127.99, 126.85, 124.84, 116.15, 112.81, 111.15, 104.74, 97.91, 39.83; HRMS (FAB) calcd for $C_{11}H_{12}Br_2N_5O$ (MH$^+$) 387.9409, found 387.9402.

sventrin hydrochloride (24). Using the same general procedure as used for the synthesis of 1H-pyrrole-2-carboxylic acid [3-(2-amino-1H-imidazol-4-yl)-propyl]-amide hydrochloride 17, 0.050 g of 4-(3-amino-propenyl)-1H-imidazol-2-ylamine dihydrochloride afforded 0.062 g (61%) of sventrin hydrochloride 24 as a pale yellow solid: $^1$H NMR (400 MHz, DMSO-d$_6$) δ 8.49 (t, 1H, J=5.6 Hz), 7.06 (s, 1H), 6.77 (s, 2H), 6.75 (s, 1H), 6.19 (d, 1H, J=15.6 Hz), 6.02 (dt, 1H, J=5.6, 11.2 Hz), 3.94 (m, 2H), 3.89 (s, 3H); $^{13}$C NMR (100 MHz, DMSO-d$_6$) δ 159.57, 147.44, 127.59, 126.75, 124.85, 116.25, 114.17, 111.20, 110.88, 96.98, 35.45; HRMS (ESI) calcd for $C_{12}H_{14}Br_2N_5O$ (MH$^+$) 401.9560, found 401.9560.

4-(2-amino-ethyl)-1H-imidazol-2-ylamine dihydrochloride (26). 1,4-diamino-2-butanone dihydrochloride 25 (0.300 g, 1.71 mmol) and cyanamide (0.753 g, 17.9 mmol) were dissolved in water (10 mL). The pH of the solution was adjusted to pH=4.3 before heating the reaction at 95° C. for 3.5 h while open to the atmosphere. After cooling to ambient temperature ethanol (10 mL) was added to the flask and the solution was evaporated to dryness. Purification of the residue by column chromatography (MeOH sat. with NH$_3$/CH$_2$Cl$_2$ 90:10) yielded the product as its corresponding free base. Addition of methanol (10 mL) and concentrated hydrochloric acid followed by evaporation in vacuo afforded the target compound 26 (0.211 g, 62%) as a yellow solid: $^1$H NMR (300 MHz, DMSO-d$_6$) δ 6.21 (s, 1H), 5.14 (br s, 2H), 2.81 (m, 2H), 2.47 (m, 2H); HRMS (ESI) calcd for $C_5H_{11}N_4$ (MH$^+$) 127.0978, found 127.0977.

4,5-dibromo-1-methyl-pyrrole-2-carboxylic acid [2-(2-amino-1H-imidazol-4-yl)-ethyl]-amide hydrochloride (27). Using the same general procedure as used for the synthesis of 1H-pyrrole-2-carboxylic acid [3-(2-amino-1H-imidazol-4-yl)-propyl]-amide hydrochloride 17, 0.150 g of 4-(2-amino-ethyl)-1H-imidazol-2-ylamine dihydrochloride 26 afforded 0.206 g (64%) of the title compound 27 as an off-white solid: $^1$H NMR (300 MHz, DMSO-d$_6$) δ 8.24 (t, 1H, J=5.1 Hz), 6.95 (s, 1H), 6.20 (s, 1H), 5.02 (s, 2H), 3.87 (s, 3H), 3.31 (m, 2H); $^{13}$C NMR (75 MHz, DMSO-d$_6$) δ 159.54, 149.20, 128.14, 113.86, 113.69, 110.33, 99.14, 96.83, 35.33, 27.45; HRMS (ESI) calcd for $C_{11}H_{14}Br_2N_5O$ (MH$^+$) 389.9559, found 389.9574.

4-(4-amino-butyl)-1H-imidazol-2-ylamine dihydrochloride (29). Using the same general procedure as used for the synthesis of 4-(3-amino-propyl)-1H-imidazol-2-ylamine dihydrochloride 16, 12.5 g of lysine methyl ester dihydrochloride 28 afforded 2.25 g (18%) of the target compound 29 as a yellow solid: $^1$H NMR (300 MHz, DMSO-d$_6$) δ 6.09 (s, 1H), 4.96 (s, 2H), 2.56 (t, 2H, J=6.3 Hz), 2.27 (t, 2H, J=6.9 Hz), 1.35-1.51 (m, 4H); $^{13}$C NMR (100 MHz, DMSO-d$_6$) δ 149.11, 132.29, 110.59, 40.75, 31.41, 26.62, 26.12; HRMS (ESI) calcd for $C_7H_{15}N_4$ (MH$^+$) 155.1291, found 155.1293.

4,5-dibromo-1-methyl-pyrrole-2-carboxylic acid [4-(2-amino-1H-imidazol-4-yl)-butyl]-amide hydrochloride (30). Using the same general procedure as used for the synthesis of 1H-pyrrole-2-carboxylic acid [3-(2-amino-1H-imidazol-4-yl)-propyl]-amide hydrochloride 17, 0.200 g of 4-(4-amino-butyl)-1H-imidazol-2-ylamine dihydrochloride 29 delivered 0.216 g (54%) of the target compound 30 as a pale yellow solid: $^1$H NMR (300 MHz, DMSO-d$_6$) δ 8.20 (t, 1H, J=5.1 Hz), 6.99 (s, 1H), 6.35 (s, 1H), 6.29 (bs, 2H), 3.86 (s, 3H), 3.17 (m, 2H), 2.35 (m, 2H), 1.49 (m, 4H); $^{13}$C NMR (100 MHz, DMSO-d$_6$) δ 159.66, 147.48, 128.39, 128.06, 113.86, 110.37, 109.17, 96.85, 38.23, 35.35, 28.51, 25.48, 24.53; HRMS (ESI) calcd for $C_{13}H_{18}Br_2N_5O$ (MH$^+$) 417.9873, found 417.9870.

2-amino-5-(3-amino-propylidene)-1,5-dihydro-imidazol-4-one dihydrochloride. 4-(3-amino-propyl)-1H-imidazol-2-ylamine 16 (0.200 g, 0.930 mmol) was dissolved in anhydrous dimethyl sulfoxide (6 mL). Bromine (0.047 mL, 0.930 mmol) was added drop-wise and the solution was stirred at room temperature for 1 h. Diethyl ether (7 mL) was added and the organics were then decanted. The residue was purified by column chromatography (MeOH sat. with NH$_3$) to yield the desired product as its free base. Addition of concentrated hydrochloric acid to a methanol solution (8 mL) of the free base followed by evaporation under reduced pressure afforded the target compound ((Z)-isomer exclusively) (0.141 g, 67%) as a tan solid: $^1$H NMR (300 MHz, DMSO-d$_6$) δ 12.10 (br s, 1H), 9.20 (br s, 2H), 8.18 (br s, 2H), 5.92 (t, 1H, J=7.8 Hz), 2.96 (m, 2H), 2.66 (m, 2H); $^{13}$C NMR (100 MHz, DMSO-d$_6$) δ 164.13, 156.63, 130.88, 113.70, 37.57, 24.94; HRMS (FAB) calcd for $C_6H_{10}N_4O$ (MH$^+$) 155.0933, found 155.0943.

dispacamide hydrochloride (31). Using the same general procedure as used for 2-amino-5-(3-amino-propylidene)-1,5-dihydro-imidazol-4-one dihydrochloride, 0.185 g of dihydrooroidin hydrochloride 19 gave 0.120 g (63%) of dispacamide hydrochloride (8:1 Z/E isomer) 31 as a tan solid: $^1$H NMR (300 MHz, CD$_3$OD) (Z isomer) δ 6.79 (s, 1H), 6.14 (t, 1H, J=7.8 Hz), 3.46 (t, 2H, J=6.9 Hz), 2.58 (dt, 2H, J=6.9, 14.7 Hz); $^{13}$C NMR (75 MHz, DMSO-d$_6$) δ 164.32, 162.06, 157.58, 130.90, 128.75, 119.09, 114.51, 106.47, 100.15, 39.11, 28.81; HRMS (ESI) calcd for $C_{11}H_{12}Br_2N_5O_2$ (MH$^+$) 403.9352, found 403.9350.

4,5-dibromo-1-methyl-pyrrole-2-carboxylic acid [3-(2-amino-5-oxo-3,5-dihydro-imidazol-4-ylidene)-propyl]-amide hydrochloride (32). Using the same general procedure as used for 2-amino-5-(3-amino-propylidene)-1,5-dihydro-imidazol-4-one dihydrochloride, 0.100 g of dihydrosventrin hydrochloride 23 gave 0.048 g (47%) of the title compound 32 as a tan solid ((Z)-isomer exclusively). $^1$H NMR (300 MHz, CD$_3$OD) δ 6.84 (s, 1H), 6.16 (t, 1H, J=7.8 Hz), 3.91 (s, 3H), 3.46 (t, 2H, J=6.9 Hz), 2.59 (dt, 2H, J=6.9, 14.7 Hz); $^{13}$C NMR (100 MHz, DMSO-d$_6$) δ 163.80, 163.00, 157.19, 130.63, 129.04, 119.42, 115.92, 112.67, 99.09, 39.06, 36.28, 28.73; HRMS (ESI) calcd for $C_{12}H_{14}Br_2N_5O_2$ (MH$^+$) 417.9509, found 417.9511.

General procedure for the synthesis of tryptophan based Region C SAR analogues: Tryptamine hydrochloride (0.150 g, 0.763 mmol), the desired appropriately substituted trichloroacetyl pyrrole (0.915 mmol), and anhydrous sodium carbonate (0.162 g, 1.53 mmol), were dissolved in anhydrous N,N-dimethylformamide (5 mL). The reaction was stirred at ambient temperature for 8 h upon which it was partitioned between ethyl acetate (75 mL) and water (35 mL). The organic layer was successively washed with water (3×20 mL), an aqueous solution of 1N HCl (2×35 mL), brine (20 mL), dried over anhydrous sodium sulfate, filtered, and concentrated under reduced pressure. Purification of the crude residue by column chromatography (Ethyl Acetate/Hexanes) yielded the final targets in the sub-library.

1H-pyrrole-2-carboxylic acid [2-(1H-indol-3-yl)-ethyl]-amide. white solid (80%): $^1$H NMR (300 MHz, DMSO-d$_6$) δ 11.41 (s, 1H), 10.80 (s, 1H), 8.11 (m, 1H), 7.58 (d, 1H, J=7.5

Hz), 7.33 (d, 1H, J=7.8 Hz), 7.16 (s, 1H), 7.08 (t, 1H, J=6.6 Hz), 6.97 (t, 1H, J=7.2 Hz), 6.83 (s, 1H), 6.74 (s, 1H), 6.06 (s, 1H) 3.47 (dt, 2H, J=7.2, 14.1 Hz), 2.90 (t, 2H, J=7.5 Hz); $^{13}$C NMR (100 MHz, DMSO-d$_6$) δ 160.69, 136.27, 127.31, 126.53, 122.58, 121.13, 120.95, 118.36, 118.25, 112.00, 111.40, 109.66, 108.52, 39.47, 25.59; HRMS (FAB) calcd for C$_{15}$H$_{16}$N$_3$O (MH$^+$) 254.1293, found 254.1281.

4-bromo-1H-pyrrole-2-carboxylic acid [2-(1H-indol-3-yl)-ethyl]-amide. white solid (81%): $^1$H NMR (300 MHz, DMSO-d$_6$) δ 11.81 (s, 1H), 10.81 (s, 1H), 8.23 (t, 1H, J=6.0 Hz), 7.56 (d, 1H, J=7.8 Hz), 7.33 (d, 1H, J=8.1 Hz), 7.16 (s, 1H), 7.06 (t, 1H, J=6.6 Hz), 6.97 (m, 2H), 6.82 (s, 1H), 3.48 (dt, 2H, J=6.9, 13.5 Hz), 2.90 (t, 2H, J=7.8 Hz); $^{13}$C NMR (100 MHz, DMSO-d$_6$) δ 159.59, 136.25, 127.26, 127.14, 122.65, 121.06, 120.95, 118.31, 118.25, 111.84, 111.41, 111.26, 94.12, 25.39; HRMS (FAB) calcd for C$_{15}$H$_{15}$BrN$_3$O (MH$^+$) 332.0398, found 332.0388.

4,5-dibromo-1H-pyrrole-2-carboxylic acid [2-(1H-indol-3-yl)-ethyl]-amide. white solid (60%): $^1$H NMR (300 MHz, DMSO-d$_6$) δ 12.67 (s, 1H), 10.81 (s, 1H), 8.25 (t, 1H, J=5.1 Hz), 7.57 (d, 1H, J=8.1 Hz), 7.33 (d, 1H, J=8.4 Hz), 7.15 (s, 1H), 7.07 (t, 1H, J=6.9 Hz), 6.97 (t, 1H, J=7.2 Hz), 6.90 (d, 1H, J=2.7 Hz), 3.47 (dt, 2H, J=6.6, 13.2 Hz), 2.89 (t, 2H, J=7.2 Hz); $^{13}$C NMR (100 MHz, DMSO-d$_6$) δ 158.87, 136.25, 128.41, 127.25, 122.70. 120.96, 118.29, 118.27, 112.42, 111.76, 111.41, 104.39, 97.79, 39.57, 25.31; HRMS (EST) calcd for C$_{15}$H$_{14}$Br$_2$N$_3$O (MH$^+$) 409.9498, found 409.9501.

4,5-dichloro-1H-pyrrole-2-carboxylic acid [2-(1H-indol-3-yl)-ethyl]-amide. white solid (73%): $^1$H NMR (300 MHz, DMSO-d$_6$) δ 12.71 (s, 1H), 10.81 (s, 1H), 8.27 (m, 1H), 7.56 (d, 1H, J=7.8 Hz), 7.32 (d, 1H, J=8.1 Hz), 7.15 (s, 1H), 7.03 (t, 1H, J=6.9 Hz), 6.96 (t, 1H, J=6.9 Hz), 6.86 (s, 1H), 3.47 (dt, 2H, J=6.3, 13.2 Hz), 2.90 (t, 2H, J=7.5 Hz); $^{13}$C NMR (75 MHz, DMSO-d$_6$) δ 159.63, 136.91, 127.91, 125.80, 123.34, 121.61, 118.94, 118.91, 115.33, 112.41, 112.07, 110.09, 108.54, 25.98; HRMS (FAB) calcd for C$_{15}$H$_{13}$Cl$_2$N$_3$O (M$^+$) 321.0436, found 321.0429.

1-methyl-pyrrole-2-carboxylic acid [2-(1H-indol-3-yl)-ethyl]-amide. white solid (63%): $^1$H NMR (300 MHz, DMSO-d$_6$) δ 10.81 (s, 1H), 8.10 (t, 1H, J=5.4 Hz), 7.57 (d, 1H, J=7.8 Hz), 7.33 (d, 1H, J=8.1 Hz), 7.16 (s, 1H), 7.06 (t, 1H, J=7.2 Hz), 7.00 (t, 1H, J=7.8 Hz) 6.87 (s, 1H), 6.73 (d, 1H, J=2.1 Hz), 6.00 (s, 1H), 3.84 (s, 3H), 3.45 (dt, 2H, J=6.9, 14.1 Hz), 2.89 (t, 2H, J=7.8 Hz); $^{13}$C NMR (75 MHz, DMSO-d$_6$) δ 161.31, 136.23, 127.46, 127.28, 125.78, 122.57, 120.91, 118.32, 118.21, 111.98, 111.94, 111.36, 106.51, 36.16, 25.49; HRMS (FAB) calcd for C$_{16}$H$_{18}$N$_3$O (MH$^+$) 268.1450, found 268.1434.

4-bromo-1-methyl-pyrrole-2-carboxylic acid [2-(1H-indol-3-yl)-ethyl]-amide. white solid (72%): $^1$H NMR (300 MHz, DMSO-d$_6$) δ 10.81 (s, 1H), 8.20 (t, 1H, J=5.4 Hz), 7.57 (d, 1H, J=7.8 Hz), 7.33 (d, 1H, J=8.1 Hz), 7.16 (d, 1H, J=1.8 Hz), 7.07 (m, 2H), 6.97 (t, 1H, J=6.9 Hz), 6.80 (d, 1H, J=1.8 Hz), 3.82 (s, 3H), 3.45 (dt, 2H, J=6.9, 14.1 Hz), 2.89 (t, 2H, J=7.8 Hz); $^{13}$C NMR (75 MHz, DMSO-d$_6$) δ 159.94, 136.04, 127.08, 126.63, 126.42, 122.48, 120.75, 118.12, 118.06, 113.24, 111.69, 111.23, 92.74, 36.31, 25.29; HRMS (FAB) calcd for C$_{16}$H$_{16}$BrN$_3$O (M$^+$) 345.0477, found 345.0483.

4,5-dibromo-1-methyl-pyrrole-2-carboxylic acid [2-(1H-indol-3-yl)-ethyl]-amide. white solid (77%). $^1$H NMR (300 MHz, DMSO-d$_6$) δ 10.81 (s, 1H), 8.32 (t, 1H, J=5.7 Hz), 7.55 (d, 1H, J=7.5 Hz), 7.33 (d, 1H, J=8.1 Hz), 7.16 (s, 1H,) 7.06 (t, 1H, J=7.2 Hz), 7.00 (t, 1H, J=7.5 Hz), 6.95 (s, 1H), 3.88 (s, 3H), 3.45 (dt, 2H, J=6.3, 13.5 Hz), 2.89 (t, 2H, J=7.8 Hz); $^{13}$C NMR (100 MHz, DMSO-d$_6$) δ 159.66, 136.22, 128.15, 127.25, 122.67, 120.91, 118.24, 118.21, 113.78, 111.75, 111.37, 110.31, 96.81, 39.66, 35.32, 25.13; HRMS (EST) calcd for C$_{16}$H$_{16}$Br$_2$N$_3$O (MH$^+$) 423.9654, found 423.9655.

General procedure for the synthesis of imidazole based Region C SAR analogues (34-40): Histamine dihydrochloride 33 (0.100 g, 1.36 mmol), the desired appropriately substituted trichloroacetyl pyrrole (1.43 mmol), and anhydrous sodium carbonate (0.432 g, 4.08 mmol), were dissolved in anhydrous N,N-dimethylformamide (7 mL). The reaction was stirred at ambient temperature for 6 h upon which it was partitioned between ethyl acetate (75 mL) and water (35 mL). The organic layer was successively washed with water (3×20 mL), sat. NaHCO$_3$ (2×35 mL), brine (20 mL), dried over anhydrous sodium sulfate, filtered, and concentrated under reduced pressure. Purification of the crude residue by column chromatography (CH$_2$Cl$_2$/Methanol 85:15) delivered the desired targets in their free base form. Addition of concentrated HCl to a methanolic solution (8 mL) of the free base followed by rotary evaporation afforded the final analogues in this series as their corresponding hydrochloride salts.

1H-pyrrole-2-carboxylic acid [2-(1H-imidazol-4-yl)-ethyl]-amide hydrochloride (34). white solid (54%): $^1$H NMR (400 MHz, DMSO-d$_6$) δ 11.46 (s, 1H), 9.01 (s, 1H), 8.23 (t, 1H, J=5.6 Hz), 7.46 (s, 1H), 6.82 (m, 1H), 6.73 (m, 1H), 6.05 (dd, 1H, J=2.8, 6.0 Hz), 3.50 (dt, 2H, J=6.8, 12.8 Hz), 2.87 (t, 1H, J=6.8 Hz); $^{13}$C NMR (100 MHz, DMSO-d$_6$) δ 161.40, 134.28, 131.82, 126.75, 122.01, 116.71, 110.80, 109.18, 37.98, 25.40; HRMS (FAB) calcd for C$_{10}$H$_{13}$N$_4$O (MH$^+$) 205.1089, found 205.1083.

4-bromo-1H-pyrrole-2-carboxylic acid [2-(1H-imidazol-4-yl)-ethyl]-amide hydrochloride (35). white solid (40%): $^1$H NMR (300 MHz, DMSO-d$_6$) δ 11.80 (s, 1H), 8.18 (t, 1H, J=5.4 Hz), 7.53 (s, 1H), 6.96 (s, 1H), 6.80 (s, 2H), 3.41 (m, 2H), 2.70 (t, 2H, J=7.2 Hz); $^{13}$C NMR (100 MHz, DMSO-d$_6$) δ 159.55, 134.72, 127.06, 121.10, 116.67, 111.28, 94.92, 38.83, 27.18; HRMS (FAB) calcd for C$_{10}$H$_{12}$BrN$_4$O (MH$^+$) 283.0194, found 283.0198.

4,5-dibromo-1H-pyrrole-2-carboxylic acid [2-(1H-imidazol-4-yl)-ethyl]-amide hydrochloride (36). white solid (35%):. $^1$H NMR (300 MHz, DMSO-d$_6$) δ 12.64 (br s, 1H), 8.20 (t, 1H, J=5.7 Hz), 7.59 (s, 1H), 6.89 (s, 1H), 6.83 (s, 1H), 3.41 (dt, 2H, J=7.2, 13.2 Hz), 2.71 (t, 2H, J=7.2 Hz); $^{13}$C NMR (100 MHz, DMSO-d$_6$) δ 158.88, 133.83, 131.81, 128.10, 116.27, 112.97, 104.45, 97.84, 37.82, 25.10; HRMS (FAB) calcd for C$_{10}$H$_{11}$Br$_2$N$_4$O (MH$^+$) 360.9300, found 360.9295.

4,5-dichloro-1H-pyrrole-2-carboxylic acid [2-(1H-imidazol-4-yl)-ethyl]-amide hydrochloride (37). white solid (62%): $^1$H NMR (400 MHz, DMSO-d$_6$) δ 12.82 (s, 1H), 9.02 (s, 1H), 8.56 (t, 1H, J=5.6 Hz), 7.46 (s, 1H), 6.94 (d, 1H, J=2.8 Hz), 3.50 (dt, 2H, J=6.8, 12.8 Hz), 2.89 (t, 2H, J=6.4 Hz); $^{13}$C NMR (100 MHz, DMSO-d$_6$) δ 159.04, 133.53, 130.96, 124.76, 116.10, 114.73, 110.16, 107.95, 37.49, 24.43; HRMS (ESI) calcd for C$_{10}$H$_{11}$Cl$_2$N$_4$O (MH$^+$) 273.0304, found 273.0309.

1-methyl-pyrrole-2-carboxylic acid [2-(1H-imidazol-4-yl)-ethyl]-amide hydrochloride (38). white solid (55%): $^1$H NMR (300 MHz, DMSO-d$_6$) δ 14.60 (bs, 1H), 14.32 (bs, 1H), 9.03 (s, 1H), 8.17 (s, 1H), 7.50 (s, 1H), 6.87 (s, 1H), 6.74 (s, 1H), 5.98 (d, 1H, J=2.7 Hz), 3.80 (s, 3H), 3.48 (m, 2H). 2.88 (m, 2H); $^{13}$C NMR (100 MHz, DMSO-d$_6$) δ 161.32, 134.68, 127.51, 125.75, 116.69. 111.98, 106.57, 38.77, 36.14, 27.17; HRMS (ESI) calcd for C$_{11}$H$_{15}$N$_4$O (MH$^+$) 219.1240, found 219.1245.

4-bromo-1-methyl-pyrrole-2-carboxylic acid [2-(1H-imidazol-4-yl)-ethyl]-amide hydrochloride (39). white solid (54%): $^1$H NMR (300 MHz, DMSO-d$_6$) δ 11.86 (br s, 1H), 8.15 (m, 1H), 7.53 (s, 1H), 7.06 (d, 1H, J=1.5 Hz), 6.79 (m, 2H), 3.81 (s, 3H), 3.38 (m, 2H), 2.69 (t, 1H, J=7.8 Hz); $^{13}$C NMR (75 MHz, DMSO-d$_6$) δ 160.12, 134.66, 126.83, 126.52, 113.36, 92.85, 38.80, 36.29, 27.00; HRMS (ESI) calcd for C$_{11}$H$_{14}$BrN$_4$O (MH$^+$) 297.0345, found 297.0348.

4,5-dibromo-1-methyl-pyrrole-2-carboxylic acid [2-(1H-imidazol-4-yl)-ethyl]-amide hydrochloride (40). white solid (60%): $^1$H NMR (300 MHz, DMSO-d$_6$) δ 11.85 (br s, 1H), 8.26 (t, 1H, J=5.4 Hz), 7.54 (s, 1H), 6.95 (s, 1H), 6.80 (s, 1H), 3.87 (s, 3H), 3.39 (dt, 2H, J=6.9, 13.8 Hz), 2.70 (t, 2H, J=7.2 Hz); $^{13}$C NMR (100 MHz, DMSO-d$_6$) δ 159.72, 133.67, 131.48, 127.78, 116.20, 114.14, 110.62, 96.88, 37.75, 35.33, 24.71; HRMS (FAB) calcd for C$_{11}$H$_{13}$Br$_2$N$_4$O$_2$ (MH$^+$) 374.9456, found 374.9458.

4-(3-amino-propyl)-1,3-dihydro-imidazole-2-thione hydrochloride (42). To an Erlenmeyer flask was prepared a solution of L-ornithine methyl ester hydrochloride (10.50 g, 47.9 mmol) in water (125 mL). The solution was cooled to 5° C. and pH adjusted to a value of 1.5 with concentrated HCl. While being careful to maintain the above stated temperature and pH, 5% Na(Hg) (250 g) was added slowly to the solution over a time period of 35 min. After the addition was complete and bubbling had calmed the Hg was decanted from the solution. The remaining aqueous portion was drained into a separate flask where potassium thiocyanate (14.0 g, 144 mmol) and water (75 mL) was added. The pH of solution was adjusted to a value of 4.30 and the flask was then heated at 95° C. while open to the atmosphere for 1.5 h. After cooling to room temperature, ethanol (75 mL) was added and the reaction was evaporated to dryness. The residue was taken up in methanol and filtered to remove NaCl. After all of the NaCl had been removed the crude residue was purified by column chromatography (CH$_2$Cl/MeOH sat. with NH$_3$ 80:20) to afford the desired compound in its free base form. Addition of concentrated hydrochloric acid to a methanol solution (50 mL) of the free base followed by evaporation to dryness gave 4.51 g (48%) of the title compound 42 as a tan solid: $^1$H NMR (300 MHz, DMSO-d$_6$) δ 11.92 (s, 1H), 11.69 (s, 1H), 7.77 (s, 2H), 6.58 (s, 1H), 2.73 (m, 2H), 2.42 (t, 2H, J=6.6 Hz), 1.76 (tt, 2H, J=7.5, 13.8 Hz); $^{13}$C NMR (100 MHz, DMSO-d$_6$) δ 160.23, 128.03, 111.69, 38.08, 25.75, 21.27; HRMS (FAB) calcd for C$_6$H$_{12}$N$_3$S (MN$^+$) 158.0752, found 158.0743.

General procedure for the synthesis of 2-thioimadazolone Region C SAR analogues (43-49): 4-(3-amino-propyl)-1,3-dihydro-imidazole-2-thione hydrochloride 42 (0.150 g, 0.774 mmol), the desired appropriately substituted trichloroacetyl pyrrole (0.852 mmol), and anhydrous sodium carbonate (0.246 g, 2.32 mmol), were dissolved in anhydrous N,N-dimethylformamide (5 mL). The reaction was stirred at ambient temperature for 12 h upon which it was partitioned between ethyl acetate (75 mL) and water (35 mL). The organic layer was successively washed with water (3×20 mL), a 1N aqueous solution of HCl (2×35 mL), brine (20 mL), dried over anhydrous sodium sulfate, filtered, and concentrated under reduced pressure. Purification of the crude residue by column chromatography (CH$_2$Cl$_2$/Methanol) afforded the final analogues in this series.

1H-pyrrole-2-carboxylic acid [3-(2-thioxo-2,3-dihydro-1H-imidazol-4-yl)-propyl]-amide (43). pale yellow solid (53%): $^1$H NMR (300 MHz, DMSO-d$_6$) δ 11.40 (s, 1H), 8.20 (t, 1H, J=5.7 Hz), 6.97 (s, 1H), 6.82 (m, 1H), 6.75 (m, 1H), 6.06 (dd, 1H, J=2.1, 5.4 Hz), 3.23 (dt, 2H, J=6.6, 12.9 Hz), 2.52 (m, 2H), 1.75 (tt, 2H, J=7.2, 14.7 Hz); $^{13}$C NMR (75 MHz, DMSO-d$_6$) δ 160.80, 160.71, 130.67, 126.31, 121.14, 113.24, 109.77, 108.47, 37.67, 28.32, 22.01; HRMS (FAB) calcd for C$_{11}$H$_{15}$N$_4$OS (MH$^+$) 251.0967, found 251.0961.

4-bromo-1H-pyrrole-2-carboxylic acid [3-(2-thioxo-2,3-dihydro-1H-imidazol-4-yl)-propyl]-amide (44). pale yellow solid (52%): $^1$H NMR (300 MHz, DMSO-d$_6$) δ 11.87 (s, 1H), 11.81 (s, 1H), 11.65 (s, 1H), 8.10 (t, 1H, J=5.1 Hz), 6.96 (s, 1H), 6.83 (s, 1H), 6.57 (s, 1H), 3.18 (dt, 2H, J=6.3, 12.3 Hz), 2.37 (t, 2H, J=7.5 Hz), 1.71 (tt, 2H, J=6.9, 13.8 Hz); $^{13}$C NMR (100 MHz, DMSO-d$_6$) δ 160.35, 160.30, 130.05, 127.63, 121.74, 112.76, 112.04, 95.56, 38.43 28.77, 22.52; HRMS (ESI) calcd for C$_{11}$H$_{14}$BrN$_4$OS (MH$^+$) 329.0066, found 329.0062.

4,5-dibromo-1H-pyrrole-2-carboxylic acid [3-(2-thioxo-2,3-dihydro-1H-imidazol-4-yl)-propyl]-amide (45). white solid (41%): $^1$H NMR (300 MHz, DMSO-d$_6$) δ 12.68 (s, 1H), 11.86 (s, 1H), 11.65 (s, 1H), 8.13 (t, 1H, J=5.1 Hz), 6.91 (d, 1H, J=2.7 Hz), 6.57 (s, 1H), 3.17 (m, 2H), 2.36 (t, 2H, J=6.9 Hz), 1.70 (tt, 2H, J=6.9, 13.8 Hz); $^{13}$C NMR (75 MHz, DMSO-d$_6$) δ 160.04, 158.91, 128.85, 128.02, 112.45, 111.30, 104.43, 97.76, 37.78, 27.95, 21.72; HRMS (ESI) calcd for C$_{11}$H$_{13}$Br$_2$N$_4$OS (MH$^+$) 406.9171, found 406.9174.

4,5-dichloro-1H-pyrrole-2-carboxylic acid [3-(2-thioxo-2,3-dihydro-1H-imidazol-4-yl)-propyl]-amide (46). yellow solid (65%): $^1$H NMR (300 MHz, DMSO-d$_6$) δ 12.71 (s, 1H), 11.86 (s, 1H), 11.65 (s, 1H), 8.15 (m, 1H), 6.86 (s, 1H), 6.56 (s, 1H), 3.17 (m, 2H), 2.36 (t, 2H, J=7.5 Hz), 1.71 (m, 2H); $^{13}$C NMR (100 MHz, DMSO-d$_6$) δ 160.73, 159.70, 129.53, 125.60, 115.40, 111.97, 110.16, 108.55, 38.47, 28.62, 22.40; HRMS (FAB) calcd for C$_{11}$H$_{12}$Cl$_2$N$_4$OS (M$^+$) 318.0109, found 318.0099.

1-methyl-pyrrole-2-carboxylic acid [3-(2-thioxo-2,3-dihydro-1H-imidazol-4-yl)-propyl]-amide (47). pale yellow solid (57%): $^1$H NMR (300 MHz, DMSO-d$_6$) δ 7.99 (m, 1H), 6.99 (s, 1H), 6.86 (s, 1H), 6.74 (m, 1H), 5.98 (m, 1H), 3.20 (dt, 2H, J=6.0, 12.3 Hz), 2.54 (t, 2H, J=7.2 Hz), 1.77 (tt, 2H, J=6.9, 14.1 Hz); $^{13}$C NMR (75 MHz, DMSO-d$_6$) δ 161.38, 160.95, 127.51, 125.64, 115.10, 112.09, 106.50, 97.60, 37.71, 36.11, 28.32, 22.15; HRMS (ESI) calcd for C$_{12}$H$_{17}$N$_4$OS (MH$^+$) 265.1118, found 265.1120.

4-bromo-1-methyl-pyrrole-2-carboxylic acid [3-(2-thioxo-2,3-dihydro-1H-imidazol-4-yl)-propyl]-amide (48). yellow solid (54%): $^1$H NMR (300 MHz, DMSO-d$_6$) δ 11.86 (s, 1H), 11.64 (s, 1H), 8.07 (m, 1H), 7.07 (s, 1H), 6.81 (s, 1H), 6.56 (s, 1H), 3.80 (s, 3H), 3.13 (dt, 2H, J=6.3, 12.9 Hz), 2.36 (t, 2H, J=7.8 Hz), 1.69 (m, 2H); $^{13}$C NMR (75 MHz, DMSO-d$_6$) δ 160.25, 160.00, 128.95, 126.85, 126.45, 113.45, 111.34, 92.87, 37.70, 36.30, 27.96, 21.78; HRMS (ESI) calcd for C$_{12}$H$_{16}$BrN$_4$OS (MH$^+$) 343.0222, found 343.0223.

4,5-dibromo-1-methyl-pyrrole-2-carboxylic acid [3-(2-thioxo-2,3-dihydro-1H-imidazol-4-yl)-propyl]-amide (49). white solid (71%): $^1$H NMR (400 MHz, DMSO-d$_6$) δ 11.85 (s, 1H), 11.64 (s, 1H), 8.19 (t, 1H, J=5.2 Hz), 6.97 (s, 1H), 6.55 (s, 1H), 3.86 (s, 3H), 3.15 (dt, 2H, J=6.4, 12.4 Hz), 2.36 (t, 2H, J=7.2 Hz), 1.70 (tt, 2H, J=7.2, 14.0 Hz); $^{13}$C NMR (75 MHz, DMSO-d$_6$) δ 160.00, 159.76, 128.89, 128.10, 113.84, 111.33, 110.42, 96.84, 37.86, 35.35, 27.85, 21.77; HRMS (ESI) calcd for C$_{12}$H$_{15}$Br$_2$N$_4$OS (MH$^+$) 420.9328, found 420.9327.

1-bromo-5-phthalimido-2-pentanone. 4-phthalimidobutanoic acid 50 (4.64 g, 19.9 mmol) was dissolved in CH$_2$Cl$_2$ (100 mL) at 0° C. and a catalytic amount of DMF was added. To this solution was added oxalyl chloride (5.2 mL, 59.6 mmol) drop-wise and the solution was then warned to room temperature. After 1 h, the solvent and excess oxalyl chloride were removed under reduced pressure. The resulting solid was dissolved into CH$_2$Cl$_2$ (10 mL) and added slowly to a 0° C. solution of CH$_2$N$_2$ (~60 mmol generated from Diazald® diazomethane precursor/KOH) in Et$_2$O (170 mL). This solution was stirred at 0° C. for 1.5 h at which time the reaction was quenched with the drop-wise addition of 48% HBr (7.0 mL). The reaction mixture was diluted with CH$_2$Cl$_2$ (50 mL)

and immediately washed with sat. NaHCO$_3$, brine, dried (MgSO$_4$), filtered and concentrated. The resulting white solid was filtered and washed with Et$_2$O (100 mL) to obtain the title compound (4.77 g, 84%) as a fine white powder: $^1$H NMR (300 MHz, DMSO-d$_6$) δ 7.85 (m, 4H), 4.32 (s, 2H), 3.57 (t, 2H, J=6.9 Hz), 2.65 (t, 2H, J=6.9 Hz), 1.82 (quint., 2H, J=6.9 Hz); $^{13}$C NMR (75 MHz, DMSO-d$_6$) δ 200.94, 168.05, 134.34, 131.68, 123.01, 36.94, 36.64, 36.37, 22.30; HRMS (ESI) calcd for C$_{13}$H$_{13}$BrNO$_3$ (MH$^+$) 310.0073, found 310.0072.

2-amino-4-(3-phthalimidopropyl)thiazole (51). 1-bromo-5-phthalimido-2-pentanone (0.500 g, 1.61 mmol) was dissolved in DMF (3.5 mL) at 0° C. and thiourea (0.135 g, 1.77 mmol) was added drop-wise as a solution in DMF (0.50 mL). The solution was allowed to warm to room temperature and stirring was continued for 2 h at which time the DMF was removed under reduced pressure and the resulting slurry was made alkaline with 10% K$_2$CO$_3$ (100 ML). The aqueous solution was then extracted with EtOAc (3×40 mL) and the organic layer was washed with brine (50 mL), dried (Na$_2$SO$_4$), filtered and concentrated to obtain 51 (448 mg, 97%) as a fine white powder in its freebase form: $^1$H NMR (300 MHz, DMSO-d$_6$) δ 7.85 (m, 4H), 6.78 (s, 2H), 6.13 (s, 1H), 3.56 (t, 2H, J=6.9 Hz), 2.42 (t, 2H, J=7.5 Hz), 1.88 (quint., 2H, J=7.5 Hz); $^{13}$C NMR (75 MHz, DMSO-d$_6$) δ 168.01, 167.87, 151.20, 134.25, 131.61, 122.89, 100.17, 37.27, 28.70, 27.09; HRMS (ESI) calcd for C$_{14}$H$_{14}$N$_3$O$_2$S (MH$^+$) 288.0801, found 288.0799.

2-amino-4-(3-aminopropyl)thiazole dihydrochloride. 2-amino-4-(3-phthalimidopropyl)thiazole (51) (0.300 g, 1.04 mmol) was dissolved in MeOH (4.5 mL) and N$_2$H$_4$ (0.10 mL, 3.20 mmol) was added drop-wise to the stirring solution. The solution was stirred at room temperature for 1 h, warmed to 55° C. for 0.5 h and then cooled to room temperature. The slurry was filtered and the filtrate concentrated under reduced pressure. The resulting residue was purified by flash column chromatography (50-100% MeOH/CH$_2$Cl$_2$; followed by 5-7% TEA/MeOH) to obtain the corresponding freebase (0.148 g, 90%) as a fine white powder. Addition of concentrated HCl to a cold methanolic solution (8 mL) of the freebase followed by evaporation under reduced pressure delivered the title compound as its dihydrochloride salt. $^1$H NMR (300 MHz, DMSO-d$_6$) δ 9.07 (bs, 2H), 8.06 (bs, 3H), 6.57 (s, 1H), 2.78 (m, 2H), 2.62 (t, 2H, J=7.2 Hz), 1.87 (quint., 2H, J=7.2 Hz); $^{13}$C NMR (75 MHz, DMSO-d$_6$) δ 169.90, 139.21, 102.13, 37.68, 25.10, 24.47; HRMS (ESI) calcd for C$_6$H$_{12}$N$_3$S (MH$^+$) 158.0746, found 158.0745.

General procedure for the synthesis of 2-AT Region C SAR analogues: 2-amino-4-(3-aminopropyl)thiazole (0.200 mmol), the appropriately substituted trichloroacetyl pyrrole (0.210 mmol) and anhydrous potassium carbonate (0.300 mmol) were dissolved in anhydrous N,N-dimethylformamide (1.5 mL) and allowed to stir for 16 h at room temperature. The mixture was then concentrated under reduced pressure and the resulting residue was dissolved in EtOAc (40 mL) and washed with H$_2$O (3×20 mL) and brine (20 mL), dried (Na$_2$SO$_4$), filtered and concentrated. The crude residue was purified by flash column chromatography (30-100% EtOAc/Hexanes; followed by 5-10% MeOH/EtOAc) to obtain pure product. Addition of concentrated HCl to a methanolic solution (5 mL) of the freebase followed by concentration under reduced pressure afforded the requisite analogues for this series as their hydrochloride salts.

1H-pyrrole-2-carboxylic acid [3-(2-amino-thiazol-4-yl)-propyl]-amide hydrochloride. tan solid (64%): $^1$H NMR (300 MHz, DMSO-d$_6$) 11.51 (s, 1H), 9.26 (s, 2H), 8.21 (s, 1H), 6.84 (s, 1H), 6.79 (s, 1H), 6.59 (s, 1H), 6.07 (d, 1H, J=2.7 Hz), 3.24 (q, 2H, J=5.7 Hz), 2.57 (t, 2H, J=7.2 Hz), 1.79 (quint., 2H, J=7.2 Hz); $^{13}$C NMR (75 MHz, DMSO-d$_6$) δ 169.90, 160.68, 139.79, 126.28, 121.02, 110.02, 108.34, 101.61, 37.49, 27.59, 24.93; HRMS (ESI) calcd for C$_{11}$H$_{15}$N$_4$OS (MH$^+$) 251.0961, found 251.0960.

4,5-dibromo-1H-pyrrole-2-carboxylic acid [3-(2-amino-thiazol-4-yl)-propyl]-amide hydrochloride. tan solid (56%): $^1$H NMR (400 MHz, DMSO-d$_6$) 12.76 (s, 1H), 9.19 (s, 2H), 8.36 (t, 1H, J=5.6 Hz), 6.96 (d, 1H, J=2.0 Hz), 6.58 (s, 1H), 3.23 (q, 2H, J=7.2 Hz), 2.56 (t, 2H, J=7.2 Hz), 1.78 (quint., 2H, J=7.2 Hz); $^{13}$C NMR (75 MHz, DMSO-d$_6$) δ 169.91, 158.87, 139.93, 128.23, 112.81, 104.20, 101.70, 97.76, 37.67, 27.35, 25.00; HRMS (ESI) calcd for C$_{11}$H$_{13}$Br$_2$N$_4$OS (MH$^+$) 406.9171, found 406.9165.

1-methyl-pyrrole-2-carboxylic acid [3-(2-amino-thiazol-4-yl)-propyl]-amide hydrochloride. tan solid (56%): $^1$H NMR (300 MHz, DMSO-d$_6$) 9.19 (br s, 2H), 8.08 (m, 2H), 6.88 (t, 1H, J=2.1 Hz), 6.78 (dd, 1H, J=3.9 & 2.1 Hz), 6.57 (s, 1H), 5.99 (dd, 1H, J=3.9 & 2.7 Hz), 3.82 (s, 3H), 3.20 (q, 2H, J=7.2 Hz), 2.55 (t, 2H, J=7.2 Hz), 1.78 (quint, 2H, J=7.2 Hz); $^{13}$C NMR (75 MHz, DMSO-d$_6$) δ 169.83, 161.37, 139.93, 127.40, 125.54, 112.04, 106.40, 101.54, 37.44, 35.94, 27.52 24.98; HRMS (ESI) calcd for C$_{12}$H$_{17}$N$_4$OS (MH$^+$) 265.1118, found 265.1117.

4,5-dibromo-1-methyl-pyrrole-2-carboxylic acid [3-(2-amino-thiazol-4-yl)-propyl]-amide hydrochloride. tan solid (62%): $^1$H NMR (400 MHz, DMSO-d$_6$) 9.02 (br s, 2H), 8.29 (n, 1H), 7.02 (s, 1H), 6.55 (s, 1H), 3.87 (s, 3H), 3.19 (q, 2H, J=6.8 Hz), 2.53 (m, 2H), 1.77 (t, 2H, J=6.8 Hz); $^{13}$C NMR (75 MHz, DMSO-d$_6$) δ 169.92, 159.83, 140.23, 128.03, 114.03, 110.40, 101.71, 96.86, 37.78, 35.34, 27.31, 25.14; HRMS (ESI) calcd for C$_{12}$H$_{15}$Br$_2$N$_4$OS (MH$^+$) 420.9328, found 420.9321.

EXAMPLE 6

Figure 20:
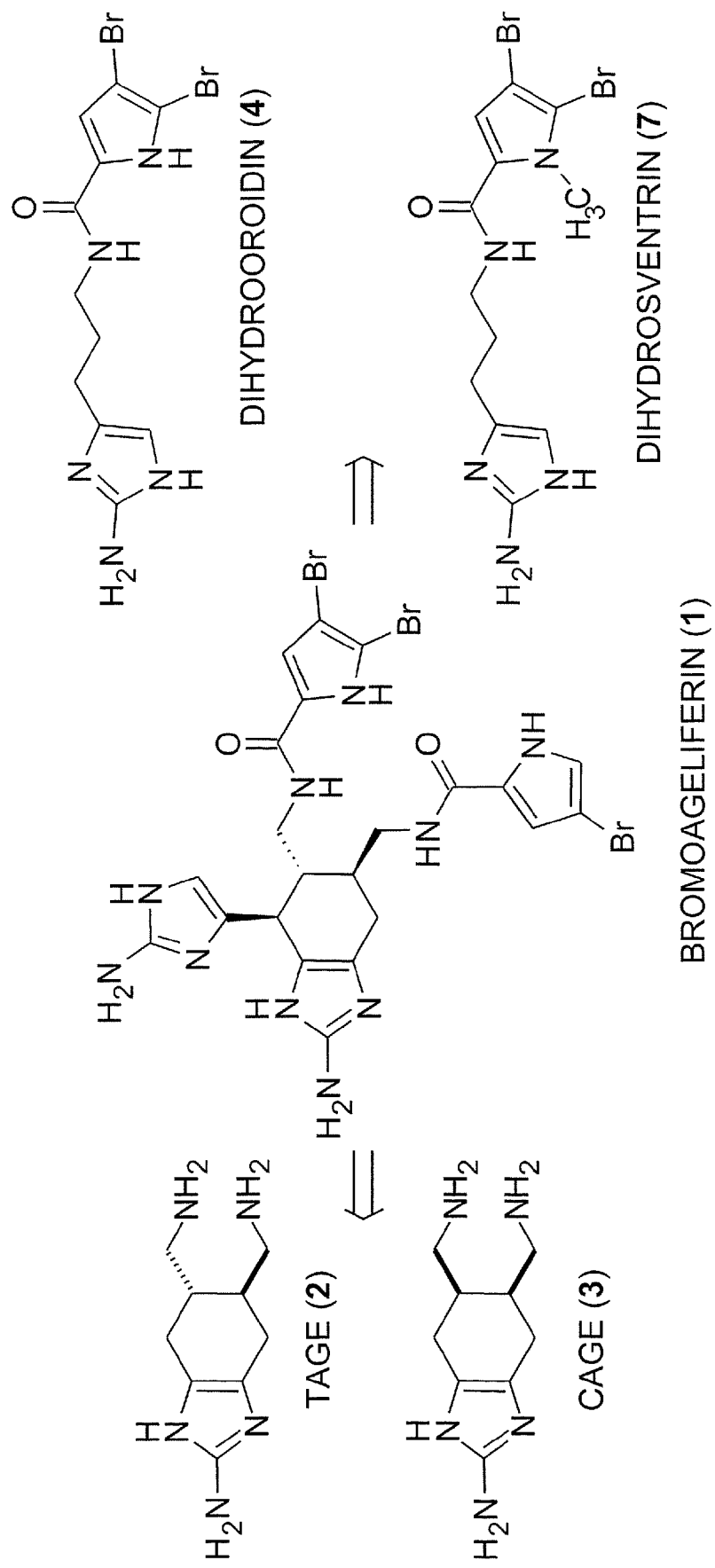
FIG. 20. Natural product derivatives as anti-biofilm molecules, including dihydrosventrin (DHS).

Inhibition and dispersion of proteobacterial biofilms with dihydrooroidin derivatives. A dihydrooroidin library was assembled as described above by solution-based synthetic methods, and each member of the library was fully characterized ($^1$H NMR, $^{13}$C NMR, HRMS). The analogue library was subsequently screened in a 96-well format using a crystal violet reporter assay to assess each analogue's ability to inhibit the formation of P. aerutginosa biofilms. From this initial screen, the derivative dihydrosventrin (DHS) (FIG. 20) was discovered to be the most potent member of the library and was further evaluated.

Follow-up dose response experiments revealed that DHS had IC$_{50}$ values of 51 μM against PAO1 and 111 μM against PA14 (Table 5), indicating that DHS was approximately 2-fold more active than both TAGE and CAGE. It is noteworthy that DHS displayed much greater activity than both oroidin 5 (IC$_{50}$=190 μM PAO1, IC$_{50}$=166 μM PA14) and its unsaturated parent sventrin 6 (IC$_{50}$=75 μM PAO1, IC$_{50}$=115 μM PA14). Dihydroorodin 4 showed only marginal activity (<70%) at 500 μM. Comparison of both growth curves and colony counts for PAO1 and PA14 grown in the absence or presence of DHS (7), oroidin (5), and sventrin (6) indicated that the inhibition of biofilm formation was not due to a bactericidal effect (not shown).

Given that DHS displayed exceptional activity in inhibiting the formation of PAO1 and PA14 biofilms, it was determined whether it would also inhibit the formation of a mucoid variant of P. aeruginosa. After a CF patient is colonized by P. aeruginosa, the bacterium undergoes a phenotypic shift from a non-mucoid to a mucoid form. J. Govan and V. Deretic, Microbiol. Rev. 1996, 60, (3), 539-74. D. Ramsey and D.

Wozniak, *Mol. Microbial* 2005, 56, (2), 309-22. Numerous studies have correlated the appearance of mucoid *P. aeruginosa* with a decline in the pulmonary clinical status of CF patients. J. Govan and V. Deretic, *Microbiol. Rev.* 1996, 60, (3), 539-74. R. Fick, et al., *Semin. Respir. Infect.* 1992, 7, (3), 168-78. R. Doggett et al., *Lancet* 1971, 1, (7692), 236-7. PDO300 (K. Mathee, et al., *Microbiology* 1999, 145 (Pt 6), 1349-57.) was employed to assay if DHS would inhibit the formation of mucoid biofilms. PDO300 is a well-characterized mucoid strain of *P. aeruginosa* that is genotypically identical to PAO1 except for the mucA mutation that converts the bacterium to the mucoid phenotype. K. Mathee et al., *Microbiology* 1999, 145 (Pt 6), 1349-57. It was determined that DHS has an $IC_{50}$ of 115 µM against PDO300 (Table 5). Growth curves again indicated that DHS lacked significant bactericidal activity against PDO300.

TABLE 5

$IC_{50}$ Values for DHS Across Selected Proteobacteria[a]

| Proteobacterial Strain | $IC_{50}$ value for DHS (µM) |
|---|---|
| *P. aeruginosa* (PAO1) | 51 |
| *P. aeruginosa* (PA14) | 111 |
| *P. aeruginosa* (PDO300) | 115 |
| *A. baumannii* (Actb) | 110 |
| *B. bronchiseptica* (RB50) | 238 |

[a]All assays performed in triplicate.

The ability of DHS to inhibit the formation of *Acinetobacter baumannii* biofilms was also assessed. *A. baumannii* is an opportunistic γ-proteobacterium that has become a severe threat over the last decade due to its multi-drug resistance. M. Falagas and E. Karveli, *Clin. Microbiol. Infect.* 2007, 13, (2), 117-119. Approximately 25% of all hospital swabs are positive for *A. baumannii*. D. Forster and F. Daschner, *Eur. J. Clin. Microbiol. Infect. Dis.* 1998, 17, (2), 73-77. *A. baumannii* survives for weeks on dry surfaces due to its ability to form robust biofilms. A. Tomaras, et al., *Microbiology-Sgm* 2003, 149, 3473-3484. Clearly, this is a serious impediment to control strategies, and small molecules that inhibit *A. baumannii* biofilms may be particularly valuable for *A. baumannii* remediation efforts. There are currently no known small molecules documented that inhibit *A. baumannii* biofilm formation. DHS was slightly more potent against *A. baumannii* as it was against PA14, revealing an $IC_{50}$ value of 110 µM (Table 5). Both growth curves and colony counts of *A. baumannii* grown in the absence or presence of DHS indicated this compound has no microbiocidal effects.

It was next determined if DHS had the ability to inhibit the formation of biofilms across bacterial order. The *Bordetella bronchiseptica* strain RB50, a β-proteobacterium, was chosen for evaluation. Bacteria of the genus *Bordetellae* are frequently isolated from mammalian respiratory tracts. P. Cotter and J. Miller, *Mol. Microbiol.* 1997, 24, (4), 671-685. *B. bronchiseptica* shares many of the same virulence factors as *Bordetella pertussis*, a β-proteobacterium that causes whooping cough and is responsible for 300,000 fatalities per year. N. Crowcroft and J. Britto, *Brit. Med. J.* 2002, 324, (7353), 1537-1538. DHS was found to have an $IC_{50}$ of 238 µM against RB50 (Table 5).

Figure 21:
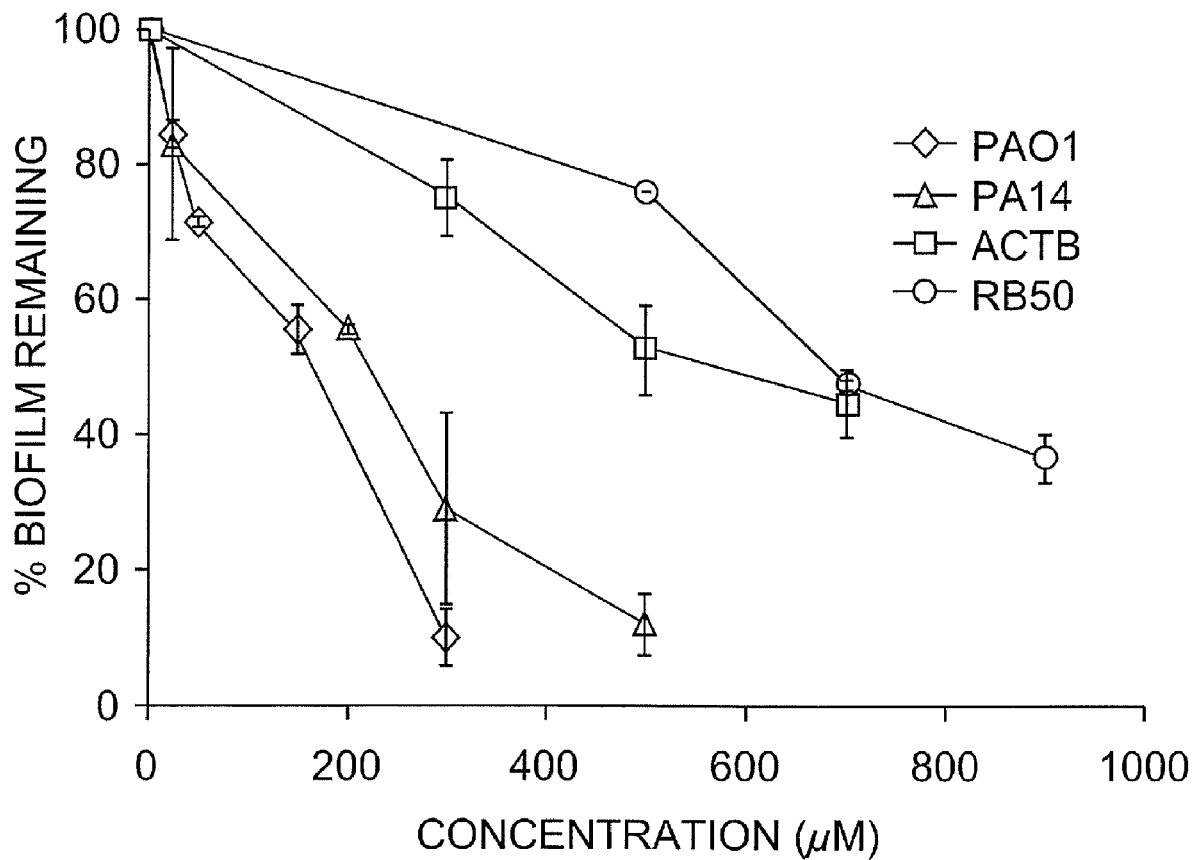
FIG. 21. Dispersion of Proteobacterial Biofilms with DHS (7).

From a clinical perspective, the ability to disperse an established biofilm can be an important consideration, because a physician is typically faced with treating an established or chronic biofilm infection. DHS was assessed for its ability to disperse existing biofilms of *P. aeruginosa*, *A. baumannii*, and *B. bronchiseptica*. Each bacterial strain was allowed to form biofilms for 24 hours in the absence of compound. At the end of 24 hours, the media and planktonic bacteria were removed and the remaining biofilm was treated either with media alone or media containing DHS. DHS was able to successfully disperse each biofilm throughout a range of concentrations (FIG. 21).

In conclusion, a simple derivative of a marine alkaloid has been identified that is active in inhibiting and dispersing proteobacterial biofilms. DHS inhibits and disperses the formation of bacterial biofilms across bacterial order. Given this activity, DHS and related compounds are useful for the development of therapeutics directed toward controlling and eliminating biofilm infections.

The foregoing is illustrative of the present invention, and is not to be construed as limiting thereof. The invention is defined by the following claims, with equivalents of the claims to be included therein.

That which is claimed is:

1. A compound of Formula (X)(I)(a)(1):

(X)(I)(a)(1)

[chemical structure: $H_2N$-imidazole-$(CH_2)_n$-C(=O)-NH-$R^6$]

wherein:
n is 2, 3 or 4, saturated or unsaturated; and
$R^6$ is selected from the group consisting of H, alkyl, alkenyl and alkynyl;
or a pharmaceutically acceptable salt or prodrug thereof.

2. The compound of claim 1, wherein $R^6$ is an alkyl having from 5 to 20 carbon atoms.

3. The compound of claim 1, wherein n is 3.

4. The compound of claim 1, wherein said compound represented by Formula (X)(I)(a)(1) is a compound of Formula (X)(I)(a)(1)(A):

(X)(I)(a)(1)(A)

[chemical structure]

or a pharmaceutically acceptable salt or prodrug thereof.

5. A composition comprising the compound of claim 1 in a pharmaceutically acceptable carrier.

6. A composition comprising a compound of Formula (X)(I)(a)(1):

(X)(I)(a)(1)

[chemical structure]

wherein:
n is 2, 3 or 4, saturated or unsaturated; and
$R^6$ is selected from the group consisting of H, alkyl, alkenyl and alkynyl;
or a pharmaceutically acceptable salt or prodrug thereof;
covalently coupled to a substrate.

7. The composition of claim 6, wherein said substrate comprises a polymeric material.

8. The composition of claim 6, wherein said substrate comprises a solid support.

9. The composition of claim 6, wherein said substrate is selected from the group consisting of a drainpipe, glaze ceramic, porcelain, glass, metal, wood, chrome, plastic, vinyl, and formica.

10. The composition of claim 6, wherein the substrate is selected from the group consisting of shower curtains or liners, upholstery, laundry, and carpeting.

11. The composition of claim 6, wherein said substrate is a ship hull or portion thereof.

12. The composition of claim 6, wherein the substrate is a food contact surface.

13. The compound of claim 2, wherein $R^6$ is a branched alkyl having from 5 to 20 carbon atoms.

14. The composition of claim 6, wherein $R^6$ is an alkyl having from 5 to 20 carbon atoms.

15. The composition of claim 6, wherein n is 3.

* * * * *

UNITED STATES PATENT AND TRADEMARK OFFICE
CERTIFICATE OF CORRECTION

| | |
|---|---|
| PATENT NO. | : 7,906,544 B2 |
| APPLICATION NO. | : 12/020112 |
| DATED | : March 15, 2011 |
| INVENTOR(S) | : Melander et al. |

Page 1 of 1

It is certified that error appears in the above-identified patent and that said Letters Patent is hereby corrected as shown below:

In the Specifications:

Column 61, Line 3: Please correct "$(MH)^{30}$" to read -- $(MH)^+$ --

Column 62, Line 38: Please correct "$(MH)^-$" to read -- $(MH)^+$ --

Column 76, Line 20: Please correct "$C_7H_4Br—Cl_3NO$" to read -- $C_7H_4Br_2Cl_3NO$ --

Column 78, Line 25: Please correct "$C_{11}H_{14}C_{12}N_5O$" to read -- $C_{11}H_{14}Cl_2N_5O$ --

Column 83, Line 41: Please correct "$(MN)^{+}$" to read -- $(MH)^+$ --

Signed and Sealed this
Sixteenth Day of August, 2011

David J. Kappos
*Director of the United States Patent and Trademark Office*